US008476271B2

(12) United States Patent
Tsuno et al.

(10) Patent No.: US 8,476,271 B2
(45) Date of Patent: Jul. 2, 2013

(54) SUBSTITUTED-QUINOXALINE-TYPE BRIDGED-PIPERIDINE COMPOUNDS AS ORL-1 MODULATORS

(75) Inventors: Naoki Tsuno, Toyonaka (JP); Jiangchao Yao, Monmouth Junction, NJ (US)

(73) Assignees: Purdue Pharma, L.P., Stamford, CT (US); Shionogi & Co., Ltd. (JP)

( * ) Notice: Subject to any disclaimer, the term of this patent is extended or adjusted under 35 U.S.C. 154(b) by 0 days.

(21) Appl. No.: 13/010,632

(22) Filed: Jan. 20, 2011

(65) Prior Publication Data

US 2011/0178090 A1  Jul. 21, 2011

Related U.S. Application Data

(63) Continuation of application No. PCT/IB2009/006356, filed on Jul. 20, 2009.

(60) Provisional application No. 61/082,482, filed on Jul. 21, 2008.

(51) Int. Cl.
*A61K 31/495* (2006.01)

(52) U.S. Cl.
USPC .......................... 514/249; 544/355

(58) Field of Classification Search
USPC .......................... 514/249; 544/355
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes |
| 3,916,899 | A | 11/1975 | Theeuwes |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,225,402 | A | 7/1993 | Ogawa et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis |
| 6,423,716 | B1 | 7/2002 | Matsuno et al. |
| 6,635,653 | B2 | 10/2003 | Goehring et al. |
| 6,930,104 | B2 | 8/2005 | Kakihana et al. |
| 7,276,518 | B2 | 10/2007 | Sundermann et al. |
| 7,282,563 | B2 | 10/2007 | Evans et al. |
| 7,288,560 | B2 | 10/2007 | Hinze et al. |
| 7,300,947 | B2 | 11/2007 | Hashimoto et al. |
| 7,566,728 | B2 | 7/2009 | Teshima et al. |
| 8,003,669 | B2 | 8/2011 | Teshima et al. |
| 2003/0236282 | A1 | 12/2003 | Hurnaus et al. |
| 2004/0176361 | A1 | 9/2004 | Fujio et al. |
| 2005/0070528 | A1 | 3/2005 | Den Hartog et al. |
| 2005/0215546 | A1 | 9/2005 | Hurnaus et al. |
| 2005/0228023 | A1 | 10/2005 | Zaveri et al. |
| 2005/0256000 | A1 | 11/2005 | Schaper et al. |
| 2007/0249604 | A1 | 10/2007 | Ho et al. |
| 2008/0200490 | A1 | 8/2008 | Hashizume et al. |
| 2009/0275555 | A1 | 11/2009 | Ronzoni et al. |
| 2010/0120841 | A1 | 5/2010 | Nakano et al. |
| 2010/0216726 | A1 | 8/2010 | Fuchino et al. |
| 2011/0166167 | A1 | 7/2011 | Neelamkavil et al. |

FOREIGN PATENT DOCUMENTS

| EP | 0990653 | 4/2000 |
| EP | 1491212 A1 | 12/2004 |
| JP | 10-291368 | 11/1998 |
| KR | 2001/0023535 | 3/2001 |
| WO | WO 95/02405 | 1/1995 |
| WO | WO 99/46260 | 9/1999 |
| WO | WO 99/50254 | 10/1999 |
| WO | WO 00/06545 | 2/2000 |
| WO | WO 00/08013 | 2/2000 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Bartho et al., "Involvement of Substituted-Quinoxaline-Type Bridged-Piperidine Compound Inflammation," Naunyn-Schmiedeberg's Archives of Pharmacol. 342:666-670 (1990).

(Continued)

*Primary Examiner* — Douglas M Willis
(74) *Attorney, Agent, or Firm* — Dechert LLP

(57) ABSTRACT

Compounds of Formula (I):

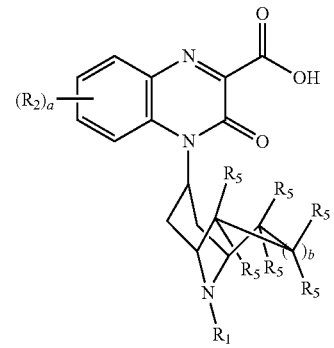

where $R_1$, $R_2$, $R_5$, a, and b are disclosed herein, and pharmaceutically acceptable derivatives thereof (a "Substituted-Quinoxaline-Type Bridged-Piperidine Compound"), compositions comprising an effective amount of a Substituted-Quinoxaline-Type Bridged-Piperidine Compound, and methods to treat or prevent a condition, such as pain, comprising administering to an animal in need thereof an effective amount of a Substituted-Quinoxaline-Type Bridged-Piperidine Compound.

51 Claims, No Drawings

FOREIGN PATENT DOCUMENTS

| WO | WO 01/39723 | | 6/2001 |
|---|---|---|---|
| WO | WO 01/39775 | | 6/2001 |
| WO | WO 01/90102 | | 11/2001 |
| WO | WO 01/07050 | | 12/2001 |
| WO | WO 02/085291 | | 10/2002 |
| WO | WO 02/085354 | | 10/2002 |
| WO | WO 02/085355 | | 10/2002 |
| WO | WO 02/085357 | | 10/2002 |
| WO | WO 02/085361 | | 10/2002 |
| WO | WO 03/062234 | | 7/2003 |
| WO | WO 2004/034983 | | 4/2004 |
| WO | WO 2005/028451 | | 3/2005 |
| WO | WO 2005/028466 | | 3/2005 |
| WO | WO 2005/075459 | | 8/2005 |
| WO | WO 2007/053435 | | 5/2007 |
| WO | WO 2007/142585 | | 12/2007 |
| WO | WO 2008/000818 A1 | | 1/2008 |
| WO | WO 2008/089201 | | 7/2008 |
| WO | WO 2009/027820 | | 3/2009 |
| WO | WO 2010/010458 | * | 1/2010 |

OTHER PUBLICATIONS

Berdini et al., "A Modified Palladium Catalyzed Reductive Amination Procedure," Tetrahedron 58:5669-5674 (2002).

Bingham et al., "Over one hundred solvates of sulfathiazole," Chem. Comm., pp. 603-604 (2001).

Buchwald et al., "Long-term, Continuous Intravenous Heparin Administration by an Implantable Infusion Pump in Ambulatory Patients with Recurrent Venous Thrombosis," Surgery 88:507-516 (1980).

Bundgaard, "Design of Prodrugs," Elsevier, Amsterdam (1985).

Bundgaard et al., "Glycolamide Esters as Biolabile Prodrugs of Carboxylic Acid Agents: Synthesis, Stability, Bioconversion, and Physicochemical Properties," J. Pharmaceut. Sci. 77(4):285-298 (1988).

Bundgaard, "Design and Application of Prodrugs," in a Textbook of Drug Design and Development, Krogsgaard-Larsen and Bundgaard, eds., Harwood Academic Publishers, Chapter 5, pp. 113-191 (1991).

Bundgaard, "(C) Means to Enhance Penetration (1) Prodrugs as a means to improve the delivery of peptide drugs," Advanced Drug Delivery Revs. 8:1-38 (1992).

Caira et al., "Preparation and Crystal Characterization of a Polymorph, a Monohydrate, and an Ethyl Acetate Solvate of the Antifungal Fluconazole," J. Pharmaceut. Sci. 93(3):601-611 (2004).

Carroll et al., "N-Substituted 4-beta-Methyl-5-(3-hydroxyphenyl)-7-alpha-amidomorphans are Potent, Selective Kappa Opioid Receptor Antagonists" J. Med. Chem. 49:1781-1791 (2006).

D'Amour et al., "A Method for Determining Loss of Pain Sensation," J. Pharmacol. Exp. Ther. 72:74-79 (1941).

During et al., "Controlled Release of Dopamine from a Polymeric Brain Implant: In Vivo Characterization," Ann. Neurol. 25:351-356 (1989).

Filer, "The Preparation and Characterization of Tritiated Neurochemicals," Isotopes in the Physical and Biomedical Sciences, vol. 1, Labeled Compounds (Part A), Buncel et al, eds., Chapter 6, pp. 155-192 (1987).

Goodson, "Dental Applications," in Medical Applications of Controlled Release, vol. 2, Applications and Evaluation, Langer and Wise, eds., CRC Press, Chapter 6, pp. 115-138 (1984).

Grupp et al., "Protection against Hypoxia-reoxygenation in the Absence of Poly (ADP-ribose) Synthetase in Isolated Working Hearts," J. Mol. Cell Cardiol. 31:297-303 (1999).

Hall, "Synthesis and Polymerization of 3-Azabicyclo-[4.3.1]decan-4-one and 7,7-Dimethyl-2-azabicyclo[4.1.1]octan-3-one," J. Org. Chem. 28:3213-3214 (1963).

Handbook of Pharmaceutical Excipients, American Pharmaceutical Association (1986).

Hanson, "Analgesic, Antipyretic and Anti-Inflammatory Drugs," Remington: The Science and Practice of Pharmacy, vol. II 1196-1221 (Gennaro, ed. 19$^{th}$ Ed. 1995).

Hargreaves et al., "A New and Sensitive Method for Measuring Thermal Nociception in Cutaneous Hyperalgesia," Pain 32(1):77-88 (1988).

Hey et al., "The Guinea Pig Model for Assessing Cardiotoxic Proclivities of Second Generation Antihistamines," Arzneim.-Forsch./Drug Res. 46(8):834-837 (1996).

Howard et al., "Intracerebral Drug Delivery in Rats With Lesion-Induced Memory Deficits," J. Neurosurg. 71:105-112 (1989).

Insel, "Analgesic-Antipyretic and Anti-inflammatory Agents and Drugs Employed in the Treatment of Gout," in Goodman & Gilman's The Pharmacological Basis of Therapeutics pp. 617-657 (Goodman et al., eds., 9$^{th}$ Ed., McGraw-Hill, New York 1996).

International Search Report and Written Opinion of the International Searching Authority for PCT/IB2008/002291 dated Feb. 6, 2009.

International Search Report and Written Opinion of the International Searching Authority for PCT/IB2009/006356 dated Oct. 8, 2009.

Kakeya et al., "Studies on Prodrugs of Cephalosporins. I. Synthesis and Biological Properties of Glycyloxygenzoyloxymethyl and Glycylaminobenzoyloxymethyl Esters of 7β-(2-Aminothiazol-4-yl)-(Z)-2-methoxyiminoacetamido]-3-methyl-3-cephem-4-carboxylic Acid," Chem. Pharm. Bull. 32(2):692-698 (1984).

Kim, "An Experimental Model for Peripheral Neuropathy Produced by Segmental Spinal Nerve Ligation in the Rat," Pain 50(3):355-363 (1992).

Langer et al., "Chemical and Physical Structure of Polymers as Carriers for Controlled Release of Bioactive Agents: A Review," J. Macramol. Sci. Rev. Macromol. Chem. C23(1):61-126 (1983).

Langer, "New Methods of Drug Delivery," Science 249:1527-1533 (1990).

Levy et al., "Inhibition of Calcification of Bioprosthetic Heart Valves by Local Controlled-Release Diphosphonate," Science 228:190-192 (1985).

Lieberman et al., Pharmaceutical Dosage Forms: Disperse Systems, 2$^{nd}$ Ed., Marcel Dekker, Inc. (1996 & 1998).

Lieberman et al., Pharmaceutical Dosage Forms: Tablets, 2$^{nd}$ Ed., Marcel Dekker, Inc., New York (1989 & 1990).

Milligan, "Principles: Extending then utility of [$^{35}$S]GTPγS binding assays," TIPS 14:87-90 (2003).

Momose et al., "Bicyclo[3.3.1]nonanes as Synthetic Intermediates. I. Improved Synthetic Methods for Bicyclo[3.3.1]nonan-3-one," Chem. Pharm. Bull. 26(1):288-295 (1978).

Olofson et al., "Value of the Vinyloxycarbonyl Unit in Hydroxyl Protection: Application to the Synthesis of Nalorphin," Tetrahedron Lett. 18:1571-1574 (1977).

Narita et al., "Identification of the G-protein coupled ORL1 receptor in the mouse spinal cord by [$^{35}$S]-GTPγS binding and immunohistochemistry," Brit. J. Pharmacol. 128:1300-1306 (1999).

Olofson et al., "A New Reagent for the Selective, High-Yield N-Dealkylation of Tertiary Amines: Improved Syntheses of Naltrexone and Nalbuphine," J. Org. Chem. 49(11):2081-2082 (1984).

Peters et al., "3,7-disubstituted bicyclo[3.3.1]nonanes—III: Synthesis and conformation of bicyclo[3.3.1]nonane-3α,7α-dicarboxylic acid, its dimethyl ester and some other 3,7-disubstituted bicyclo[3.3.1]nonanes; adamantane as an integrated holding system," Tetrahedron, 31(18):2273-2281 (1975).

Porter, "The Zinin Reduction of Nitroarenes," Org. Reactions 20:455-481 (1973).

Radebough et al., "Preformulation," pp. 1447-1676 in Remington's Pharmaceutical Sciences vol. 2 (Gennaro, ed., 19$^{th}$ Ed., Mack Publishing, Easton, PA, 1995).

Robinson, "Coating of Pharmaceutical Dosage Forms," in Osol, ed., Remington's Pharmaceutical Sciences, 16$^{th}$ Ed., Mack Publishing, Easton, PA, Ch. 89, pp. 1553-1593 (1980).

Ross et al., Pharmacodynamics: Mechanisms of Drug Action and the Relationship Between Drug Concentration and Effect, Chapter 2 in Goodman & Gilman's The Pharmacological Basis of Therapeutics 31-32 (Hardman et al., eds., 10$^{th}$ Ed. 2001).

Rylander, "Hydrogenation of Nitro Compounds," in Hydrogenation Methods pp. 104-116 (Academic Press, London) (1985).

Sato et al., "Psychotropic Agents. 3. 4-(4-Substituted piperidinyl)-1-(4-fluorophenyl)-1-butanones with Potent Neuroleptic Activity," J. Med. Chem. 21(11):1116-1120 (1978).

Saudek et al., "A Preliminary Trial of the Programmable Implantable Medication System for Insulin Delivery," New Engl. J. Med. 321:574-579 (1989).

Sefton, "Implantable Pumps," CRC Crit. Rev. Biomed. Eng. 14(3):201-240 (1987).

Seltzer et al., "A Novel Behavioral Model of Neuropathic Pain Disorders Produced in Rats by Partial Sciatic Nerve Injury," Pain 43:205-218 (1990).

Shimohigashi et al., "Sensitivity of opioid receptor-like receptor ORL1 for chemical modification on nociceptin, a naturally occurring nociceptive peptide," J. Biol. Chem. 271(39):23642-23645 (1996).

Shioiri et al., "Diphenylphosphoryl azide a new convenient reagent for a modified Curtius rearrangement and for peptide synthesis," J. Amer. Chem. Soc. 94:6202-6205 (1972).

Smolen et al., "Drug Product Design and Performance," Controlled Drug Bioavailability vol. 1, John Wiley & Sons, New York (Smolen and Ball, eds.) (1984).

Stein, "Unilateral Inflammation of the Hindpaw in Rats as a Model of Prolonged Noxious Stimulation: Alterations in Behavior and Nociceptive Thresholds," Pharmacol. Biochem. Behavior 31:451-455 (1988).

Tortolani et al., "A Convenient Synthesis to N-Aryl-Substituted 4-Piperidones," Org. Lett. 1(8):1261-1262 (1999).

Treat et al., "Liposome encapsulated doxorubicin—preliminary results of phase I and phase II trials" Liposomes in the Therapy of Infectious Disease and Cancer, pp. 317-327 and 353-365 (1989).

Van Tonder et al., "Preparation and Physicochemical Characterization of 5 Niclosamide Solvates and 1 Hemisolvate," AAPS Pharm. Sci. Tech. 5(1):Article 12, pp. 1-10 (2004).

Widder et al., eds., "Drug and Enzyme Targeting, Part A," vol. 112 in Methods in Enzymology, Academic Press (1985).

Zhou et al., "Properties of HERG Channels Stably Expressed in HEK 293 Cells Studied at Physiological Temperature," Biophysical J. 74:230-241 (1998).

* cited by examiner

SUBSTITUTED-QUINOXALINE-TYPE BRIDGED-PIPERIDINE COMPOUNDS AS ORL-1 MODULATORS

This application is a continuation of PCT application serial no. PCT/IB2009/006356, filed Jul. 20, 2009, which claims the benefit under 35 U.S.C. §119(e) of provisional application No. 61/082,482, filed Jul. 21, 2008, the contents of all of which are incorporated herein by reference.

1. FIELD OF THE INVENTION

The invention relates to Substituted-Quinoxaline-Type Bridged-Piperidine Compounds, compositions comprising an effective amount of a Substituted-Quinoxaline-Type Bridged-Piperidine Compound and methods to treat or prevent a condition, such as pain, comprising administering to an animal in need thereof an effective amount of a Substituted-Quinoxaline-Type Bridged-Piperidine Compound.

2. BACKGROUND OF THE INVENTION

Chronic pain is a major contributor to disability and is the cause of much suffering. The successful treatment of severe and chronic pain is a primary goal of the physician, with opioid analgesics being preferred drugs for doing so.

Until recently, there was evidence of three major classes of opioid receptors in the central nervous system (CNS), with each class having subtype receptors. These receptor classes are known as μ, κ and δ. As opiates have a high affinity for these receptors while not being endogenous to the body, research followed in order to identify and isolate the endogenous ligands to these receptors. These ligands were identified as enkephalins, endorphins and dynorphins.

Recent experimentation has led to the identification of a cDNA encoding an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for μ, κ and δ receptors had low affinity for the ORL-1 receptor. This characteristic, along with the fact that an endogenous ligand had not yet been discovered, led to the term "orphan receptor".

Subsequent research led to the isolation and structure of the endogenous ligand of the ORL-1 receptor (i.e., nociceptin). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication No. WO 99/46260 A1 describes quinoxalinone derivatives as inhibitors of protein kinase C.

International PCT Publication No. WO 99/50254 A1 describes quinoxalinone derivatives as serine protease inhibitors.

International PCT Publication No. WO 01/90102 A2 describes 6-heterocyclyl-3-oxo-3,4-dihydro-quinoxalines for use as herbicides.

International PCT Publication No. WO 2003/062234 A1 describes quinoxaline derivatives for use in remedying diseases in which poly(ADP-ribose) polymerase (PARP) participates.

U.S. published patent application No. US 2005/0256000 by Schaper et al. describes quinoxaline-2-one derivatives for use as safeners for plants.

International PCT Publication No. WO 2005/028451 A1 describes tetrahydroquinoxaline derivatives for use as M2 acetylcholine receptor agonists.

International PCT Publication No. WO 2009/027820 A2 describes substituted-quinoxaline-type piperidine compounds for use in treating or preventing, e.g., pain.

Citation of any reference in Section 2 of this application is not to be construed as an admission that such reference is prior art to the present application.

3. SUMMARY OF THE INVENTION

It is an object of the invention to provide new compounds that exhibit affinity for the ORL-1 receptor.

In certain embodiments of the invention, such new compounds exhibit agonist activity at the ORL-1 receptor.

In certain embodiments of the invention, such new compounds exhibit partial agonist activity at the ORL-1 receptor.

In certain other embodiments of the invention, such new compounds exhibit antagonist activity at the ORL-1 receptor.

In certain embodiments of the invention, such new compounds exhibit affinity for the ORL-1 receptor, and also for one or more of the μ, κ or δ receptors. In a particular embodiment, a new compound of the invention exhibits affinity for both the ORL-1 receptor and the μ receptor. In another embodiment, a new compound of the invention acts as an ORL-1 receptor agonist and as a μ receptor agonist. In another embodiment, a new compound of the invention acts as an ORL-1 receptor partial agonist and as a μ receptor agonist. In another embodiment, a new compound of the invention acts as an ORL-1 receptor partial agonist and as a μ receptor antagonist. In another embodiment, a new compound of the invention acts as an ORL-1 receptor antagonist and as μ receptor agonist.

Certain new compounds of the invention can be used to treat an animal suffering from chronic or acute pain.

It is a further object of the invention to provide methods of treating chronic or acute pain in an animal by administering one or more Substituted-Quinoxaline-Type Bridged-Piperidine Compounds of the invention to an animal in need of such treatment. In certain embodiments, such new Substituted-Quinoxaline-Type Bridged-Piperidine Compounds effectively treat chronic or acute pain in the animal, while producing fewer or reduced side effects compared to previously available compounds. For example, Substituted Quinoxaline-Type Bridged-Piperidine Compounds 358, 361, and 362 have surprisingly and desirably reduced abnormal behavioral side effects, such as reduced sedation, hyperactivity and/or hypo-activity. Additionally and surprisingly, Substituted Quinoxaline-Type Bridged-Piperidine Compound 362 has reduced cardiovascular side effects. These side effects were determined using known methods: an in vitro hERG (human ether a-go-go gene) assay as disclosed in Z. Zhou et al., "Properties of HERG Channels Stably Expressed in HEK 293 Cells Studied at Physiological Temperature," *Biophysical J.* 74:230-241 (1998); and APD (action potential duration) in guinea pig purkinje fibers as disclosed in J. A. Hey, "The Guinea Pig Model for Assessing Cardiotoxic Proclivities of Second Generation Antihistamines," *Arzneimittelforschung* 46(8):834-837 (1996).

The invention encompasses compounds of Formula (I):

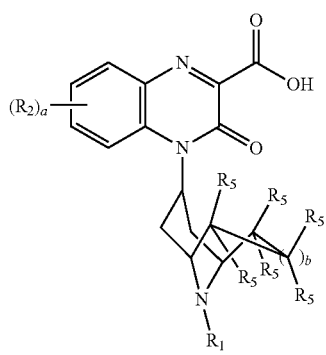

(I)

or a pharmaceutically acceptable derivative thereof wherein:

each $R_2$ is independently selected from -halo;

a is an integer selected from 0, 1 or 2;

b is an integer selected from 0 or 1;

each $R_5$ is independently selected from —H, —OH, —($C_1$-$C_3$)alkyl, —C(halo)$_3$, or -halo;

$R_1$ is —($C_9$-$C_{14}$)cycloalkyl or —($C_9$-$C_{14}$)bicycloalkyl; and each halo is independently selected from —F, —Cl, —Br, or —I.

The invention also encompasses compounds of Formula (I'):

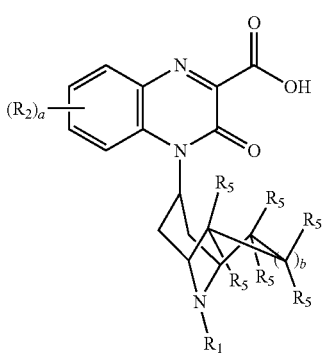

(I')

or a pharmaceutically acceptable derivative thereof wherein:

each $R_2$ is independently selected from -halo;

a is an integer selected from 0, 1 or 2;

b is an integer selected from 0 or 1;

each $R_5$ is independently selected from —H, —OH, —($C_1$-$C_3$)alkyl, —C(halo)$_3$, or -halo;

$R_1$ is —($C_9$-$C_{14}$)cycloalkyl or —($C_9$-$C_{14}$)bicycloalkyl, each of which is substituted with 1, 2 or 3 independently selected $R_3$ groups;

each $R_3$ is independently selected from —($C_1$-$C_4$)alkyl, —($C_2$-$C_6$)alkenyl, —($C_2$-$C_6$)alkynyl, or —($C_3$-$C_6$)cycloalkyl.

The invention also encompasses compounds of Formula (II):

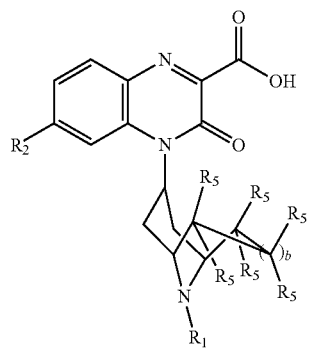

(II)

or a pharmaceutically acceptable derivative thereof where $R_1$, $R_5$, and b are defined above for the Substituted-Quinoxaline-Type Bridged-Piperidine Compounds of Formulae (I) or (I') and $R_2$ is —H or -halo.

A compound of Formula (I), Formula (I') or Formula (II) or a pharmaceutically acceptable derivative thereof (a "Substituted-Quinoxaline-Type Bridged-Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Substituted-Quinoxaline-Type Bridged-Piperidine Compound is useful for treating and/or preventing pain, anxiety, cough, diarrhea, high blood pressure, epilepsy, anorexia/cachexia, urinary incontinence, drug abuse, a memory disorder, obesity, constipation, depression, dementia, or Parkinsonism (each being a "Condition") in an animal.

The invention also relates to compositions comprising an effective amount of a Substituted-Quinoxaline-Type Bridged-Piperidine Compound and a pharmaceutically acceptable carrier or excipient. The compositions are useful for treating or preventing a Condition in an animal.

The invention further relates to methods for treating a Condition, comprising administering to an animal in need thereof an effective amount of a Substituted-Quinoxaline-Type Bridged-Piperidine Compound.

The invention further relates to methods for preventing a Condition, comprising administering to an animal in need thereof an effective amount of a Substituted-Quinoxaline-Type Bridged-Piperidine Compound.

The invention further relates to the use of a Substituted-Quinoxaline-Type Bridged-Piperidine Compound, e.g., of Formulas (I), (I') and/or (II), for the manufacture of a medicament useful for treating a Condition.

The invention further relates to the use of a Substituted-Quinoxaline-Type Bridged-Piperidine Compound, e.g., of Formulas (I), (I') and/or (II), for the manufacture of a medicament useful for preventing a Condition.

The invention still further relates to methods for inhibiting ORL-1 receptor function in a cell, comprising contacting a cell capable of expressing the ORL-1 receptor with an ORL-1 receptor function inhibiting amount of a Substituted-Quinoxaline-Type Bridged-Piperidine Compound.

The invention still further relates to methods for activating ORL-1 receptor function in a cell, comprising contacting a cell capable of expressing the ORL-1 receptor with an ORL-1 receptor function activating amount of a Substituted-Quinoxaline-Type Bridged-Piperidine Compound.

The invention still further relates to methods for preparing Substituted-Quinoxaline-Type Bridged-Piperidine Compounds and/or pharmaceutically acceptable derivatives thereof. Such methods are illustrated in the synthetic Schemes and Examples herein.

The invention still further relates to methods for preparing a composition, comprising the step of admixing a Substituted-Quinoxaline-Type Bridged-Piperidine Compound and a pharmaceutically acceptable carrier or excipient.

The invention still further relates to a kit comprising a container containing an effective amount of a Substituted-Quinoxaline-Type Bridged-Piperidine Compound.

The invention also provides novel intermediates for use in making the Substituted-Quinoxaline-Type Bridged-Piperidine Compounds.

The invention can be understood more fully by reference to the following detailed description and illustrative examples, which are intended to exemplify non-limiting embodiments of the invention. Other objects and advantages of the invention will become apparent from the following detailed description thereof.

4. DETAILED DESCRIPTION OF THE INVENTION

4.1 Substituted-Quinoxaline-Type Bridged-Piperidine Compounds of Formula (I)

As stated above, the invention encompasses Substituted-Quinoxaline-Type Bridged-Piperidine Compounds of Formula (I):

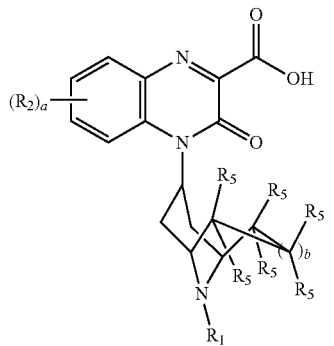

(I)

or a pharmaceutically acceptable derivative thereof where $R_1$, $R_2$, $R_5$, a, and b are defined above for the Substituted-Quinoxaline-Type Bridged-Piperidine Compounds of Formula (I).

In one embodiment, $R_1$ is —$(C_9$-$C_{14})$cycloalkyl.
In another embodiment, $R_1$ is —$(C_{11}$-$C_{14})$cycloalkyl.
In another embodiment, $R_1$ is —$(C_{11})$cycloalkyl.
In another embodiment, $R_1$ is —$(C_{12})$cycloalkyl.
In another embodiment, $R_1$ is —$(C_{13})$cycloalkyl.
In another embodiment, $R_1$ is —$(C_{14})$cycloalkyl.
In another embodiment, $R_1$ is —$(C_{10}$-$C_{14})$bicycloalkyl.
In another embodiment, $R_1$ is -indanyl, -1,2,3,4-tetrahydronaphthalenyl, -5,6,7,8-tetrahydronaphthalenyl, -perhydronaphthalenyl, bicyclo[3.3.1]nonyl, bicyclo[4.2.1]nonyl, bicyclo[3.3.2]decyl, bicyclo[4.2.2]decyl, bicyclo[4.3.1]decyl, bicyclo[3.3.3]undecyl, bicyclo[4.3.2]undecyl, or bicyclo[4.3.3]dodecyl.
In another embodiment, $R_1$ is bicyclo[3.3.1]nonyl.
In another embodiment, $R_1$ is bicyclo[3.3.1]nonyl, with the proviso that the ring system to which $R_1$ is attached is not 9-azabicyclo[3.3.1]nonan-1-yl.
In another embodiment, $R_1$ is 2-bicyclo[3.3.1]nonyl, or 3-bicyclo[3.3.1]nonyl.
In another embodiment, $R_1$ is not 9-bicyclo[3.3.1]nonyl.
In another embodiment, $R_1$ is not 1-bicyclo[3.3.1]nonyl.
In another embodiment, $R_1$ is —$(C_{11}$-$C_{14})$cycloalkyl or —$(C_{10}$-$C_{14})$bicycloalkyl.
In another embodiment, $R_1$ is 1-bicyclo[3.3.1]nonyl, 2-bicyclo[3.3.1]nonyl, 3-bicyclo[3.3.1]nonyl, or —$(C_{10}$-$C_{14})$bicycloalkyl.
In another embodiment, $R_1$ is 1-bicyclo[3.3.1]nonyl, 2-bicyclo[3.3.1]nonyl, 3-bicyclo[3.3.1]nonyl, or —$(C_{11}$-$C_{14})$cycloalkyl.
In another embodiment, $R_1$ is —$(C_{11}$-$C_{14})$cycloalkyl, 1-bicyclo[3.3.1]nonyl, 2-bicyclo[3.3.1]nonyl, 3-bicyclo[3.3.1]nonyl, or —$(C_{10}$-$C_{14})$bicycloalkyl.
In another embodiment, each $R_5$ is independently selected from —H, —$(C_1$-$C_3)$alkyl, —C(halo)$_3$, or -halo.
In another embodiment, each $R_5$ is independently selected from —H, —$CH_3$, —$CF_3$, or —F.
In another embodiment, each $R_5$ is —H, i.e., the Substituted-Quinoxaline-Type Bridged-Piperidine Compound is a compound of Formula (IA):

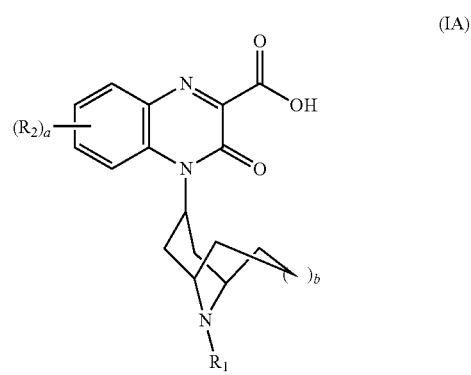

(IA)

or a pharmaceutically acceptable derivative thereof where $R_1$, $R_2$, a, and b are defined above for the Substituted-Quinoxaline-Type Bridged-Piperidine Compounds of Formula (I).

In another embodiment, a is an integer selected from 0 or 1.
In another embodiment, $R_2$ is -halo.
In another embodiment, $R_2$ is —F.
In another embodiment, a is 0.
In another embodiment, the 3-oxo-3,4-dihydroquinoxaline-2-carboxylic acid portion of the Substituted-Quinoxaline-Type Bridged-Piperidine Compound is in the endo- or exo-conformation with respect to the bridge of the bridged piperidine.
In another embodiment, the 3-oxo-3,4-dihydroquinoxaline-2-carboxylic acid portion of the Substituted-Quinoxaline-Type Bridged-Piperidine Compound is in the endo-conformation with respect to the bridge of the bridged piperidine.

In another embodiment, the 3-oxo-3,4-dihydroquinoxaline-2-carboxylic acid portion of the Substituted-Quinoxaline-Type Bridged-Piperidine Compound is in the exo-conformation with respect to the bridge of the bridged piperidine.

In another embodiment, $R_1$ is —$(C_9$-$C_{12})$cycloalkyl or —$(C_9$-$C_{12})$bicycloalkyl.

In another embodiment, $R_1$ is —$(C_9$-$C_{12})$bicycloalkyl.

In another embodiment, $R_1$ is in the endo- or exo-conformation with respect to the bridge of the bridged piperidine.

In another embodiment, $R_1$ is in the endo-conformation with respect to the bridge of the bridged piperidine.

In another embodiment, $R_1$ is in the exo-conformation with respect to the bridge of the bridged piperidine.

In another embodiment, $R_1$ is:

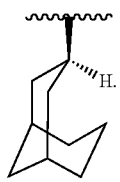

In another embodiment, $R_1$ is —$(C_9$-$C_{12})$cycloalkyl.

In another embodiment, $R_1$ is -cycloundecyl.

In another embodiment, b is 0, e.g., for a Substituted-Quinoxaline-Type Bridged-Piperidine Compound where each $R_5$ is —H, the bridged piperidine is:

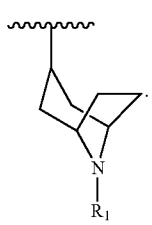

In another embodiment, b is 1, e.g., for a Substituted-Quinoxaline-Type Bridged-Piperidine Compound where each $R_5$ is —H, the bridged piperidine is:

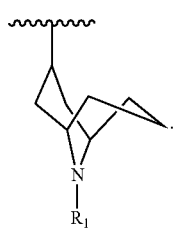

In another embodiment, the Substituted-Quinoxaline-Type Bridged-Piperidine Compound of Formula (IA) is a Substituted-Quinoxaline-Type Bridged-Piperidine Compound of Formula (IB):

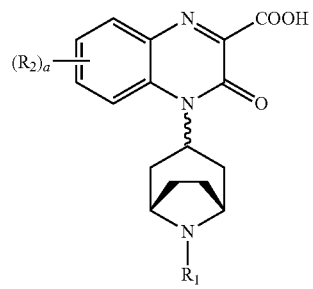

wherein $R_1$, $R_2$, and a are as defined above for the Substituted-Quinoxaline-Type Bridged-Piperidine Compounds of Formula (I).

In another embodiment, the Substituted-Quinoxaline-Type Bridged-Piperidine Compound of Formula (IA) is a Substituted-Quinoxaline-Type Bridged-Piperidine Compound of Formula (IB1):

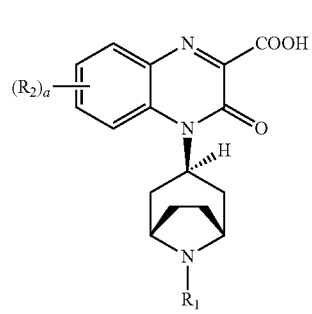

i.e., a Substituted-Quinoxaline-Type Bridged-Piperidine Compound of Formula (IB) wherein the 6-membered, nitrogen-containing ring that is fused to the benzo is in the endo-conformation with respect to the (—$CH_2$—$CH_2$—) bridge of the bridged piperidine.

In another embodiment, the Substituted-Quinoxaline-Type Bridged-Piperidine Compound of Formula (IA) is a Substituted-Quinoxaline-Type Bridged-Piperidine Compound of Formula (IB2):

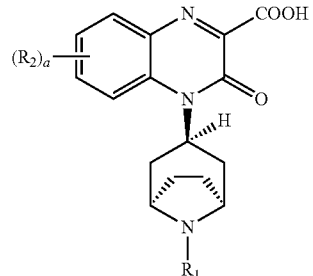

i.e., a Substituted-Quinoxaline-Type Bridged-Piperidine Compound of Formula (IB) wherein the 6-membered, nitrogen-containing ring that is fused to the benzo is in the exo-conformation with respect to the (—$CH_2$—$CH_2$—) bridge of the bridged piperidine.

In another embodiment, the Substituted-Quinoxaline-Type Bridged-Piperidine Compound of Formula (IA) is a Substituted-Quinoxaline-Type Bridged-Piperidine Compound of Formula (IC):

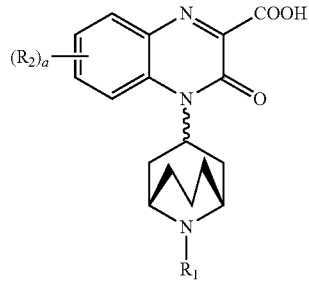

(IC)

wherein $R_1$, $R_2$, and a are as defined above for the Substituted-Quinoxaline-Type Bridged-Piperidine Compounds of Formula (I).

In another embodiment, the Substituted-Quinoxaline-Type Bridged-Piperidine Compound of Formula (IA) is a Substituted-Quinoxaline-Type Bridged-Piperidine Compound of Formula (IC1):

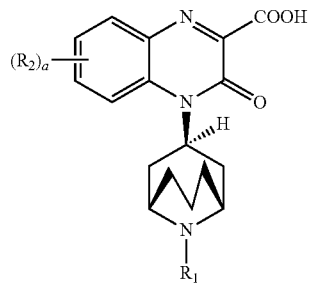

(IC1)

i.e., a Substituted-Quinoxaline-Type Bridged-Piperidine Compound of Formula (IC) wherein the 6-membered, nitrogen-containing ring that is fused to the benzo is in the endo-conformation with respect to the (—CH$_2$—CH$_2$—CH$_2$—) bridge of the bridged piperidine.

In another embodiment, the Substituted-Quinoxaline-Type Bridged-Piperidine Compound of Formula (IA) is a Substituted-Quinoxaline-Type Bridged-Piperidine Compound of Formula (IC2):

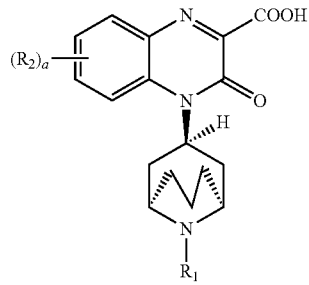

(IC2)

i.e., a Substituted-Quinoxaline-Type Bridged-Piperidine Compound of Formula (IC) wherein the 6-membered, nitrogen-containing ring that is fused to the benzo is in the exo-conformation with respect to the (—CH$_2$—CH$_2$—CH$_2$—) bridge of the bridged piperidine.

In another embodiment, the Substituted-Quinoxaline-Type Bridged-Piperidine Compound is:

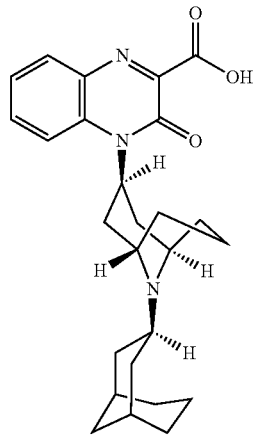

or a pharmaceutically acceptable derivative thereof.

In another embodiment, the Substituted-Quinoxaline-Type Bridged-Piperidine Compound is:

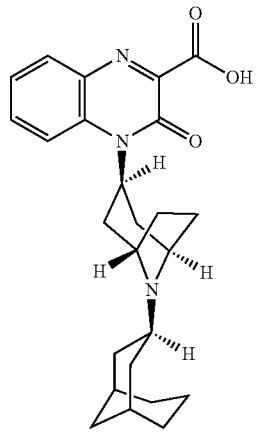

or a pharmaceutically acceptable derivative thereof.

In another embodiment, the Substituted-Quinoxaline-Type Bridged-Piperidine Compound is:

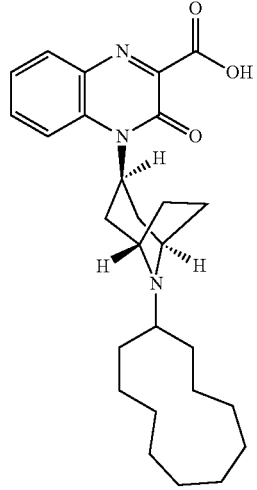 [SMILES: O=C(O)c1nc2ccccc2n([C@H]2C[C@H]3CC[C@@H](C2)N3C2CCCCCCCCCC2)c1=O]

or a pharmaceutically acceptable derivative thereof.

In another embodiment, the pharmaceutically acceptable derivative is a hydrate.

In another embodiment, the pharmaceutically acceptable derivative is a pharmaceutically acceptable salt.

In another embodiment, the pharmaceutically acceptable salt is a p-toluenesulfonic acid salt, a sulfate salt, a phosphoric acid salt, or a hydrochloride salt.

In another embodiment, the pharmaceutically acceptable salt is a p-toluenesulfonic acid salt, a sulfate salt, or a phosphoric acid salt.

In another embodiment, the pharmaceutically acceptable salt is a p-toluenesulfonic acid salt.

In another embodiment, the Substituted-Quinoxaline-Type Bridged-Piperidine Compound is not:

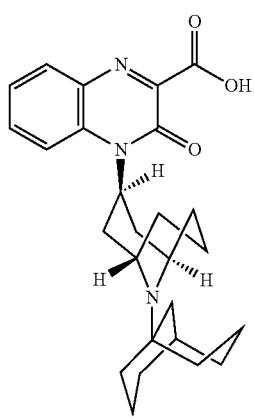 [SMILES: O=C(O)c1nc2ccccc2n([C@H]2C[C@H]3CCC[C@@H](C2)N3C23CCCC(CCC2)C3)c1=O]

or a pharmaceutically acceptable derivative thereof.

In another embodiment, the Substituted-Quinoxaline-Type Bridged-Piperidine Compound is not:

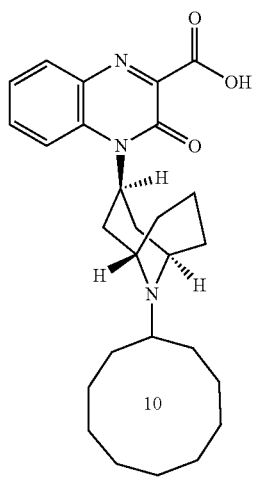 [SMILES: O=C(O)c1nc2ccccc2n([C@H]2C[C@H]3CCC[C@@H](C2)N3C2CCCCCCCCC2)c1=O]

or a pharmaceutically acceptable derivative thereof.

In another embodiment, the Substituted-Quinoxaline-Type Bridged-Piperidine Compound is not:

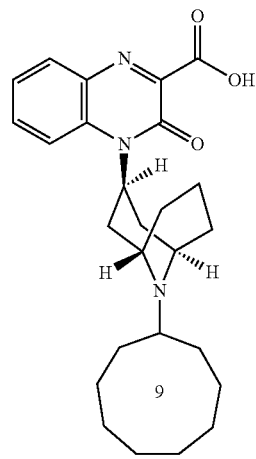 [SMILES: O=C(O)c1nc2ccccc2n([C@H]2C[C@H]3CCC[C@@H](C2)N3C2CCCCCCCC2)c1=O]

or a pharmaceutically acceptable derivative thereof.

In another embodiment, the Substituted-Quinoxaline-Type Bridged-Piperidine Compound is not:

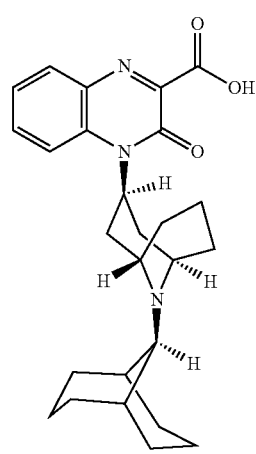 [SMILES: O=C(O)c1nc2ccccc2n([C@H]2C[C@H]3CCC[C@@H](C2)N3[C@H]2CC3CCCC2CCC3)c1=O]

or a pharmaceutically acceptable derivative thereof.

In another embodiment, the Substituted-Quinoxaline-Type Bridged-Piperidine Compound is not:

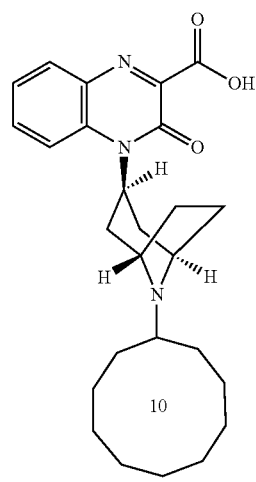 [SMILES: O=C(O)c1nc2ccccc2n([C@H]2C[C@H]3CC[C@@H](C2)N3C2CCCCCCCCC2)c1=O]

or a pharmaceutically acceptable derivative thereof.

In another embodiment, the Substituted-Quinoxaline-Type Bridged-Piperidine Compound is not:

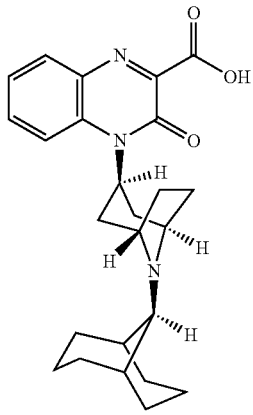

or a pharmaceutically acceptable derivative thereof.

In another embodiment, the Substituted-Quinoxaline-Type Bridged-Piperidine Compound is not:

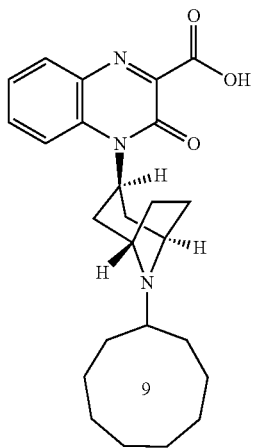 [SMILES: O=C(O)c1nc2ccccc2n([C@H]2C[C@H]3CC[C@@H](C2)N3C2CCCCCCCC2)c1=O]

or a pharmaceutically acceptable derivative thereof.

In another embodiment, the Substituted-Quinoxaline-Type Bridged-Piperidine Compound is not 4-(9-(bicyclo[3.3.1]nonan-1-yl)-9-azabicyclo[3.3.1]nonan-3-yl)-3-oxo-3,4-dihydroquinoxaline-2-carboxylic acid or 4-(9-cyclodecyl-9-azabicyclo[3.3.1]nonan-3-yl)-3-oxo-3,4-dihydroquinoxaline-2-carboxylic acid or 4-(9-cyclononyl-9-azabicyclo[3.3.1]nonan-3-yl)-3-oxo-3,4-dihydroquinoxaline-2-carboxylic acid or 4-(9-(bicyclo[3.3.1]nonan-9-yl)-9-azabicyclo[3.3.1]nonan-3-yl)-3-oxo-3,4-dihydroquinoxaline-2-carboxylic acid or 4-(8-cyclodecyl-8-azabicyclo[3.2.1]octan-3-yl)-3-oxo-3,4-dihydroquinoxaline-2-carboxylic acid or 4-(8-bicyclo[3.3.1]nonan-9-yl)-8-azabicyclo[3.2.1]octan-3-yl)-3-oxo-3,4-dihydroquinoxaline-2-carboxylic acid or 4-(8-cyclononyl-8-azabicyclo[3.2.1]octan-3-yl)-3-oxo-3,4-dihydroquinoxaline-2-carboxylic acid.

In another embodiment, the Substituted-Quinoxaline-Type Bridged-Piperidine Compound is not 4-((endo)-9-(bicyclo[3.3.1]nonan-1-yl)-9-azabicyclo[3.3.1]nonan-3-yl)-3-oxo-3,4-dihydroquinoxaline-2-carboxylic acid or 4-((endo)-9-cyclodecyl-9-azabicyclo[3.3.1]nonan-3-yl)-3-oxo-3,4-dihydroquinoxaline-2-carboxylic acid or 4-((endo)-9-cyclononyl-9-azabicyclo[3.3.1]nonan-3-yl)-3-oxo-3,4-dihydroquinoxaline-2-carboxylic acid or 4-((endo)-9-((exo)-bicyclo[3.3.1]nonan-9-yl)-9-azabicyclo[3.3.1]nonan-3-yl)-3-oxo-3,4-dihydroquinoxaline-2-carboxylic acid or 4-((endo)-8-cyclodecyl-8-azabicyclo[3.2.1]octan-3-yl)-3-oxo-3,4-dihydroquinoxaline-2-carboxylic acid or 4-((endo)-8-((exo)-bicyclo[3.3.1]nonan-9-yl)-8-azabicyclo[3.2.1]octan-3-yl)-3-oxo-3,4-dihydroquinoxaline-2-carboxylic acid or 4-((endo)-8-cyclononyl-8-azabicyclo[3.2.1]octan-3-yl)-3-oxo-3,4-dihydroquinoxaline-2-carboxylic acid.

4.2 Substituted-Quinoxaline-Type Bridged-Piperidine Compounds of Formula (I')

As stated above, the invention encompasses Substituted-Quinoxaline-Type Bridged-Piperidine Compounds of Formula (I'):

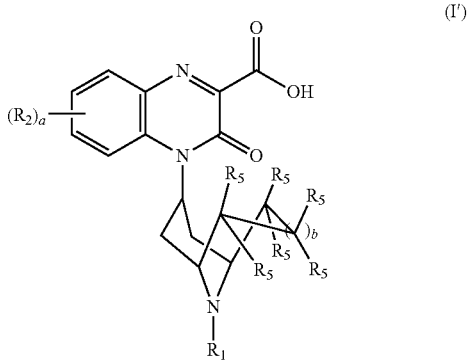

(I')

or a pharmaceutically acceptable derivative thereof where $R_1$, $R_2$, $R_5$, a, and b are defined above for the Substituted-Quinoxaline-Type Bridged-Piperidine Compounds of Formula (I').

In one embodiment, each $R_5$ is independently selected from —H, —($C_1$-$C_3$)alkyl, —C(halo)$_3$, or -halo.

In another embodiment, each $R_5$ is independently selected from —H, —$CH_3$, —$CF_3$, or —F.

In another embodiment, each $R_5$ is —H, i.e., the Substituted-Quinoxaline-Type Bridged-Piperidine Compound is a compound of Formula (I'A):

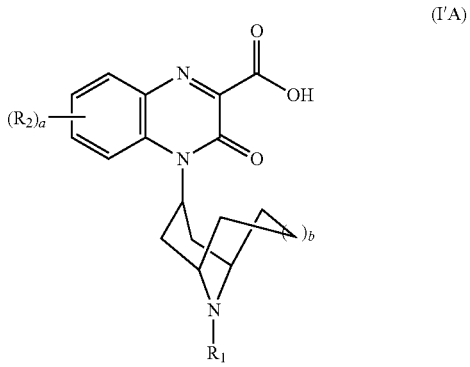

(I'A)

or a pharmaceutically acceptable derivative thereof where $R_1$, $R_2$, a, and b are defined above for the Substituted-Quinoxaline-Type Bridged-Piperidine Compounds of Formula (I').

In another embodiment, a is an integer selected from 0 or 1.

In another embodiment, $R_2$ is -halo.

In another embodiment, $R_2$ is —F.

In another embodiment, a is 0.

In another embodiment, the 3-oxo-3,4-dihydroquinoxaline-2-carboxylic acid portion of the Substituted-Quinoxaline-Type Bridged-Piperidine Compound is in the endo- or exo-conformation with respect to the bridge of the bridged piperidine.

In another embodiment, the 3-oxo-3,4-dihydroquinoxaline-2-carboxylic acid portion of the Substituted-Quinoxaline-Type Bridged-Piperidine Compound is in the endo-conformation with respect to the bridge of the bridged piperidine.

In another embodiment, the 3-oxo-3,4-dihydroquinoxaline-2-carboxylic acid portion of the Substituted-Quinoxaline-Type Bridged-Piperidine Compound is in the exo-conformation with respect to the bridge of the bridged piperidine.

In another embodiment, $R_1$ is —$(C_9-C_{12})$cycloalkyl or —$(C_9-C_{12})$bicycloalkyl.

In another embodiment, $R_1$ is —$(C_9-C_{12})$bicycloalkyl.

In another embodiment, $R_1$ is bicyclo[3.3.1]nonyl.

In another embodiment, $R_1$ is 1-bicyclo[3.3.1]nonyl, 2-bicyclo[3.3.1]nonyl, or 3-bicyclo[3.3.1]nonyl.

In another embodiment, $R_1$ is in the endo- or exo-conformation with respect to the bridge of the bridged piperidine.

In another embodiment, $R_1$ is in the endo-conformation with respect to the bridge of the bridged piperidine.

In another embodiment, $R_1$ is in the exo-conformation with respect to the bridge of the bridged piperidine.

In another embodiment, there are three independently-selected $R_3$ groups.

In another embodiment, there are two independently-selected $R_3$ groups.

In another embodiment, there is one $R_3$ group.

In another embodiment, each $R_3$ group is methyl.

In another embodiment, there are three $R_3$ groups and each $R_3$ group is independently selected from —$(C_1-C_4)$alkyl, —$(C_2-C_6)$alkenyl, —$(C_2-C_6)$alkynyl, and —$(C_3-C_6)$cycloalkyl.

In another embodiment, there are two $R_3$ groups and each $R_3$ group is independently selected from —$(C_1-C_4)$alkyl, —$(C_2-C_6)$alkenyl, —$(C_2-C_6)$alkynyl, and —$(C_3-C_6)$cycloalkyl.

In another embodiment, there is one $R_3$ group which is —$(C_1-C_4)$alkyl, —$(C_2-C_6)$alkenyl, —$(C_2-C_6)$alkynyl, or —$(C_3-C_6)$cycloalkyl.

In another embodiment, there are three $R_3$ groups and each $R_3$ group is independently selected from —$(C_1-C_4)$alkyl, —$(C_2-C_6)$alkenyl, and —$(C_2-C_6)$alkynyl.

In another embodiment, there are two $R_3$ groups and each $R_3$ group is independently selected from —$(C_1-C_4)$alkyl, —$(C_2-C_6)$alkenyl, and —$(C_2-C_6)$alkynyl.

In another embodiment, there is one $R_3$ group which is —$(C_1-C_4)$alkyl, —$(C_2-C_6)$alkenyl, or —$(C_2-C_6)$alkynyl.

In another embodiment, there are three $R_3$ groups and each $R_3$ group is independently selected from —$(C_1-C_4)$alkyl and —$(C_3-C_6)$cycloalkyl.

In another embodiment, there are two $R_3$ groups and each $R_3$ group is independently selected from —$(C_1-C_4)$alkyl and —$(C_3-C_6)$cycloalkyl.

In another embodiment, there is one $R_3$ group which is —$(C_1-C_4)$alkyl or —$(C_3-C_6)$cycloalkyl.

In another embodiment, there are three $R_3$ groups and each $R_3$ group is independently selected from -methyl, -ethyl, -n-propyl, -iso-propyl, -n-butyl, -sec-butyl, -iso-butyl, -tert-butyl, -cyclopropyl, -cyclobutyl, -cyclopentyl, and -cyclohexyl.

In another embodiment, there are three $R_3$ groups and each $R_3$ group is independently selected from -methyl, -ethyl, -n-propyl, -iso-propyl, -n-butyl, -iso-butyl, -tert-butyl, -cyclopropyl, -cyclobutyl, -cyclopentyl, and -cyclohexyl.

In another embodiment, there are three $R_3$ groups and each $R_3$ group is independently selected from -methyl, -ethyl, -n-propyl, -iso-propyl, -iso-butyl, -tert-butyl, -cyclobutyl, -cyclopentyl, and -cyclohexyl.

In another embodiment, there are three $R_3$ groups and each $R_3$ group is independently selected from -methyl, -ethyl, -tert-butyl, -cyclobutyl, -cyclopentyl, and -cyclohexyl.

In another embodiment, there are three $R_3$ groups and each $R_3$ group is independently selected from -methyl, -ethyl, -n-propyl, -iso-propyl, -n-butyl, -sec-butyl, -iso-butyl, and -tert-butyl.

In another embodiment, there are three $R_3$ groups and each $R_3$ group is independently selected from -methyl, -ethyl, -n-propyl, -iso-propyl, -n-butyl, -iso-butyl, and -tert-butyl.

In another embodiment, there are three $R_3$ groups and each $R_3$ group is independently selected from -methyl, -ethyl, -iso-propyl, -iso-butyl, and -tert-butyl.

In another embodiment, there are three $R_3$ groups and each $R_3$ group is independently selected from -methyl and -ethyl In another embodiment, there are three $R_3$ groups each of which is -methyl.

In another embodiment, there are three $R_3$ groups and each $R_3$ group is independently selected from -cyclopropyl, -cyclobutyl, -cyclopentyl, and -cyclohexyl.

In another embodiment, there are three $R_3$ groups and each $R_3$ group is independently selected from -cyclobutyl, -cyclopentyl, and -cyclohexyl.

In another embodiment, there are two $R_3$ groups and each $R_3$ group is independently selected from -methyl, -ethyl, -n-propyl, -iso-propyl, -n-butyl, -sec-butyl, -iso-butyl, -tert-butyl, -cyclopropyl, -cyclobutyl, -cyclopentyl, and -cyclohexyl.

In another embodiment, there are two $R_3$ groups and each $R_3$ group is independently selected from -methyl, -ethyl, -n-propyl, -iso-propyl, -n-butyl, -iso-butyl, -tert-butyl, -cyclopropyl, -cyclobutyl, -cyclopentyl, and -cyclohexyl.

In another embodiment, there are two $R_3$ groups and each $R_3$ group is independently selected from -methyl, -ethyl, -n-propyl, -iso-propyl, -iso-butyl, -tert-butyl, -cyclobutyl, -cyclopentyl, and -cyclohexyl.

In another embodiment, there are two $R_3$ groups and each $R_3$ group is independently selected from -methyl, -ethyl, -tert-butyl, -cyclobutyl, -cyclopentyl, and -cyclohexyl.

In another embodiment, there are two $R_3$ groups and each $R_3$ group is independently selected from -methyl, -ethyl, -n-propyl, -iso-propyl, -n-butyl, -sec-butyl, -iso-butyl, and -tert-butyl.

In another embodiment, there are two $R_3$ groups and each $R_3$ group is independently selected from -methyl, -ethyl, -n-propyl, -iso-propyl, -n-butyl, -iso-butyl, and -tert-butyl.

In another embodiment, there are two $R_3$ groups and each $R_3$ group is independently selected from -methyl, -ethyl, -iso-propyl, -iso-butyl, and -tert-butyl.

In another embodiment, there are two $R_3$ groups and each $R_3$ group is independently selected from -methyl and -ethyl In another embodiment, there are two $R_3$ groups each of which is -methyl.

In another embodiment, there are two $R_3$ groups and each $R_3$ group is independently selected from -cyclopropyl, -cyclobutyl, -cyclopentyl, and -cyclohexyl.

In another embodiment, there are two $R_3$ groups and each $R_3$ group is independently selected from -cyclobutyl, -cyclopentyl, and -cyclohexyl.

In another embodiment, there is one R$_3$ group which is -methyl, -ethyl, -n-propyl, -iso-propyl, -n-butyl, -sec-butyl, -iso-butyl, -tert-butyl, -cyclopropyl, -cyclobutyl, -cyclopentyl, or -cyclohexyl.

In another embodiment, there is one R$_3$ group which is -methyl, -ethyl, -n-propyl, -iso-propyl, -n-butyl, -iso-butyl, -tert-butyl, -cyclopropyl, -cyclobutyl, -cyclopentyl, or -cyclohexyl.

In another embodiment, there is one R$_3$ group which is -methyl, -ethyl, -n-propyl, -iso-propyl, -iso-butyl, -tert-butyl, -cyclobutyl, -cyclopentyl, or -cyclohexyl.

In another embodiment, there is one R$_3$ group which is -methyl, -ethyl, -tert-butyl, -cyclobutyl, -cyclopentyl, or -cyclohexyl.

In another embodiment, there is one R$_3$ group which is -methyl, -ethyl, -n-propyl, -iso-propyl, -n-butyl, -sec-butyl, -iso-butyl, or -tert-butyl.

In another embodiment, there is one R$_3$ group which is -methyl, -ethyl, -n-propyl, -iso-propyl, -n-butyl, -iso-butyl, or -tert-butyl.

In another embodiment, there is one R$_3$ group which is -methyl, -ethyl, -iso-propyl, -iso-butyl, or -tert-butyl.

In another embodiment, there is one R$_3$ group which is -cyclopropyl, -cyclobutyl, -cyclopentyl, or -cyclohexyl.

In another embodiment, there is one R$_3$ group which is -cyclobutyl, -cyclopentyl, or -cyclohexyl.

In another embodiment, there is one R$_3$ group which is -ethyl.

In another embodiment, there is one R$_3$ group which is -methyl.

In another embodiment, the carbon atom of the R$_1$ group which is attached to the nitrogen atom of the bridged piperidine is unsubstituted by a R$_3$ group.

In another embodiment, R$_1$ and R$_3$ together are:

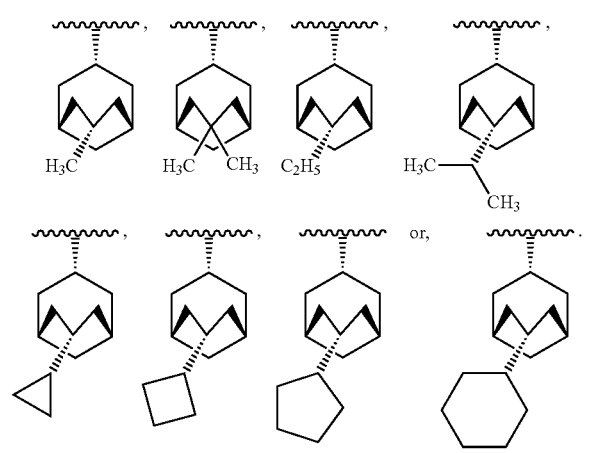

In another embodiment, R$_1$ and R$_3$ together are:

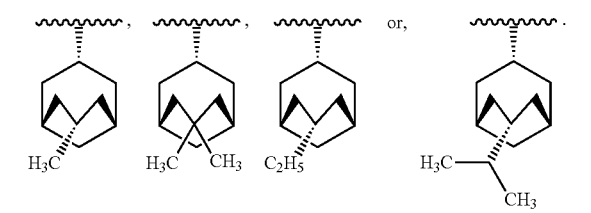

In another embodiment, R$_1$ and R$_3$ together are:

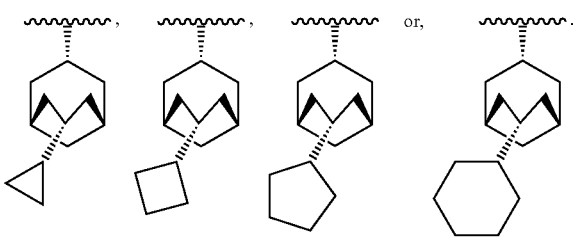

In another embodiment, R$_1$ and R$_3$ together are:

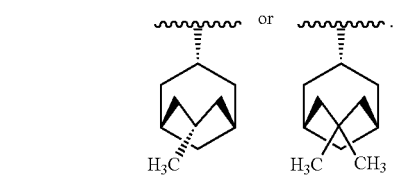

In another embodiment, R$_1$ and R$_3$ together are:

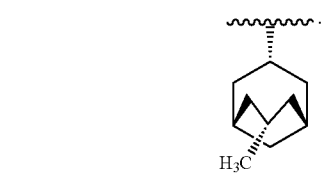

In another embodiment, R$_1$ is —(C$_9$-C$_{12}$)cycloalkyl.

In another embodiment, R$_1$ is -cycloundecyl.

In another embodiment, b is 0, e.g., for a Substituted-Quinoxaline-Type Bridged-Piperidine Compound where each R$_5$ is —H, the bridged piperidine is:

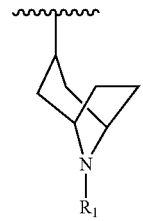

In another embodiment, b is 1, e.g., for a Substituted-Quinoxaline-Type Bridged-Piperidine Compound where each R$_5$ is —H, the bridged piperidine is:

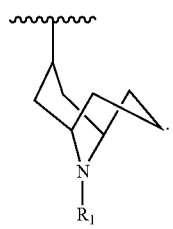

In another embodiment, the Substituted-Quinoxaline-Type Bridged-Piperidine Compound of Formula (I'A) is a Substituted-Quinoxaline-Type Bridged-Piperidine Compound of Formula (I'B):

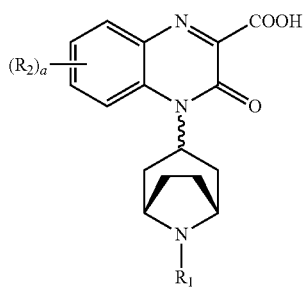

(I'B)

wherein $R_1$, $R_2$, and a are as defined above for the Substituted-Quinoxaline-Type Bridged-Piperidine Compounds of Formula (I').

In another embodiment, the Substituted-Quinoxaline-Type Bridged-Piperidine Compound of Formula (I'A) is a Substituted-Quinoxaline-Type Bridged-Piperidine Compound of Formula (I'B1):

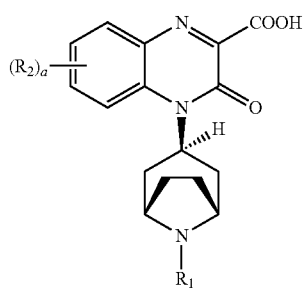

(I'B1)

i.e., a Substituted-Quinoxaline-Type Bridged-Piperidine Compound of Formula (I'B) wherein the 6-membered, nitrogen-containing ring that is fused to the benzo is in the endo-conformation with respect to the (—$CH_2$—$CH_2$—) bridge of the bridged piperidine.

In another embodiment, the Substituted-Quinoxaline-Type Bridged-Piperidine Compound of Formula (I'A) is a Substituted-Quinoxaline-Type Bridged-Piperidine Compound of Formula (I'B2):

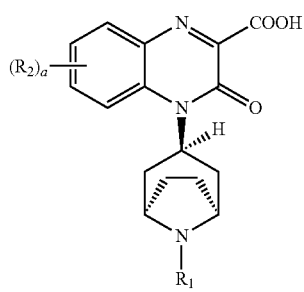

(I'B2)

i.e., a Substituted-Quinoxaline-Type Bridged-Piperidine Compound of Formula (I'B) wherein the 6-membered, nitrogen-containing ring that is fused to the benzo is in the exo-conformation with respect to the (—$CH_2$—$CH_2$—) bridge of the bridged piperidine.

In another embodiment, the Substituted-Quinoxaline-Type Bridged-Piperidine Compound of Formula (I'A) is a Substituted-Quinoxaline-Type Bridged-Piperidine Compound of Formula (I'C):

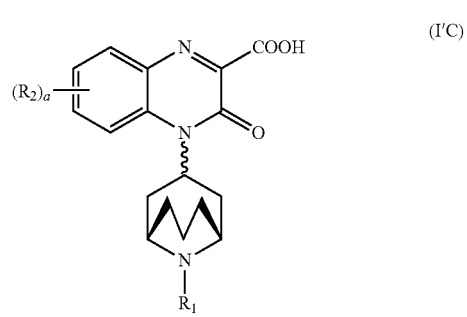

(I'C)

wherein $R_1$, $R_2$, and a are as defined above for the Substituted-Quinoxaline-Type Bridged-Piperidine Compounds of Formula (I').

In another embodiment, the Substituted-Quinoxaline-Type Bridged-Piperidine Compound of Formula (I'A) is a Substituted-Quinoxaline-Type Bridged-Piperidine Compound of Formula (I'C1):

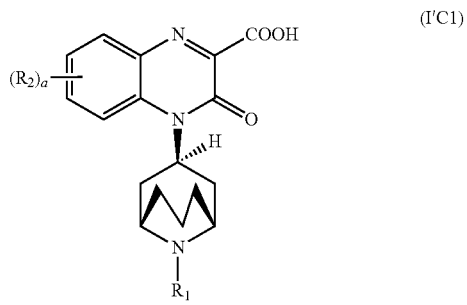

(I'C1)

i.e., a Substituted-Quinoxaline-Type Bridged-Piperidine Compound of Formula (I'C) wherein the 6-membered, nitrogen-containing ring that is fused to the benzo is in the endo-conformation with respect to the (—$CH_2$—$CH_2$—$CH_2$—) bridge of the bridged piperidine.

In another embodiment, the Substituted-Quinoxaline-Type Bridged-Piperidine Compound of Formula (I'A) is a Substituted-Quinoxaline-Type Bridged-Piperidine Compound of Formula (I'C2):

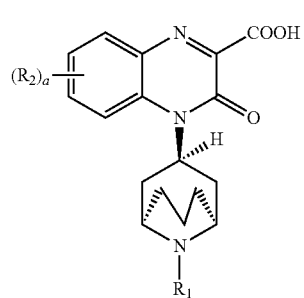

(I'C2)

i.e., a Substituted-Quinoxaline-Type Bridged-Piperidine Compound of Formula (I'C) wherein the 6-membered, nitrogen-containing ring that is fused to the benzo is in the exo-conformation with respect to the ($-CH_2-CH_2-CH_2-$) bridge of the bridged piperidine.

In another embodiment, the Substituted-Quinoxaline-Type Bridged-Piperidine Compound is:

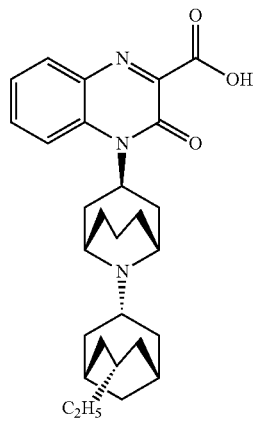 [SMILES: CC[C@@H]1C[C@@H]2C[C@H](C1)C[C@@H](N1[C@@H]3CCC[C@H]1C[C@@H](n1c(=O)c(C(=O)O)nc4ccccc41)C3)C2]

or a pharmaceutically acceptable derivative thereof.

In another embodiment, the Substituted-Quinoxaline-Type Bridged-Piperidine Compound is:

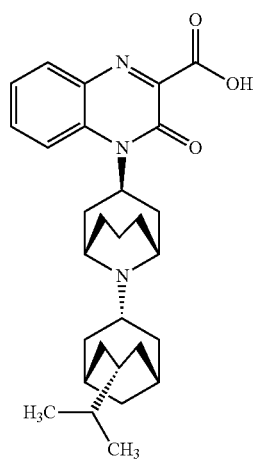 [SMILES: CC(C)[C@H]1C[C@H]2C[C@@H](C1)C[C@H](N1[C@@H]3CCC[C@H]1C[C@@H](n1c(=O)c(C(=O)O)nc4ccccc41)C3)C2]

or a pharmaceutically acceptable derivative thereof.

In another embodiment, the Substituted-Quinoxaline-Type Bridged-Piperidine Compound is:

or a pharmaceutically acceptable derivative thereof.

In another embodiment, the Substituted-Quinoxaline-Type Bridged-Piperidine Compound is:

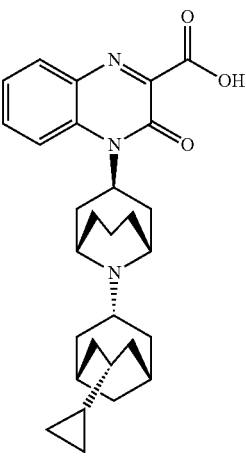 [SMILES: O=C(O)c1nc2ccccc2n([C@H]2C[C@H]3CCC[C@@H](C2)N3[C@@H]2C[C@@H]3C[C@@H](C[C@@H](C4CC4)C3)C2)c1=O]

or a pharmaceutically acceptable derivative thereof.

In another embodiment, the Substituted-Quinoxaline-Type Bridged-Piperidine Compound is:

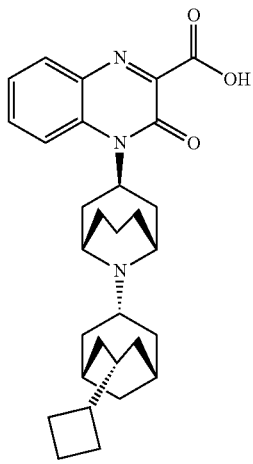 [SMILES: O=C(O)c1nc2ccccc2n([C@H]2C[C@H]3CCC[C@@H](C2)N3[C@@H]2C[C@@H]3C[C@@H](C[C@@H](C4CCC4)C3)C2)c1=O]

or a pharmaceutically acceptable derivative thereof.

In another embodiment, the Substituted-Quinoxaline-Type Bridged-Piperidine Compound is:

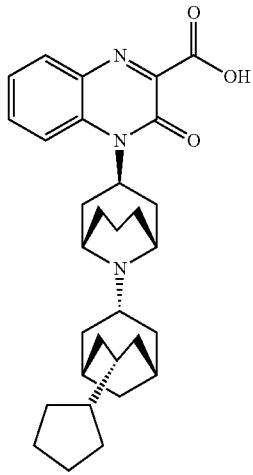 [SMILES: O=C(O)c1nc2ccccc2n([C@H]2C[C@H]3CCC[C@@H](C2)N3[C@@H]2C[C@@H]3C[C@@H](C[C@@H](C4CCCC4)C3)C2)c1=O]

or a pharmaceutically acceptable derivative thereof.

In another embodiment, the Substituted-Quinoxaline-Type Bridged-Piperidine Compound is:

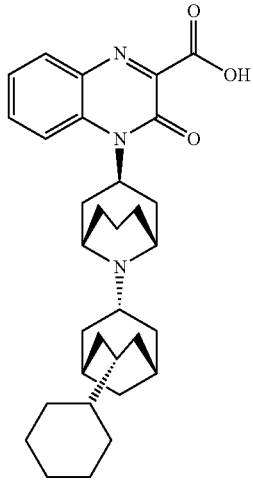 [SMILES: O=C(O)c1nc2ccccc2n([C@H]2C[C@H]3CCC[C@@H](C2)N3[C@@H]2C[C@@H]3C[C@@H](C[C@@H](C4CCCCC4)C3)C2)c1=O]

or a pharmaceutically acceptable derivative thereof.

In another embodiment, the pharmaceutically acceptable derivative is a hydrate.

In another embodiment, the pharmaceutically acceptable derivative is a pharmaceutically acceptable salt.

In another embodiment, the pharmaceutically acceptable salt is a p-toluenesulfonic acid salt, a sulfate salt, a phosphoric acid salt, or a hydrochloride salt.

In another embodiment, the pharmaceutically acceptable salt is a p-toluenesulfonic acid salt, a sulfate salt, or a phosphoric acid salt.

In another embodiment, the pharmaceutically acceptable salt is a p-toluenesulfonic acid salt.

4.3 Substituted-Quinoxaline-Type Bridged-Piperidine Compounds of Formula (II)

As stated above, the invention encompasses Substituted-Quinoxaline-Type Bridged-Piperidine Compounds of Formula (II):

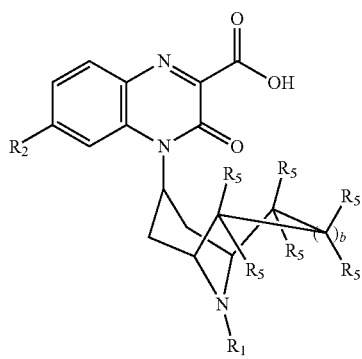

(II)

or a pharmaceutically acceptable derivative thereof where $R_1$, $R_5$, and b are defined above for the Substituted-Quinoxaline-Type Bridged-Piperidine Compounds of Formulae (I) or (I') and $R_2$ is —H or -halo.

In one embodiment, each $R_5$ is independently selected from —H, —($C_1$-$C_3$)alkyl, —C(halo)$_3$, or -halo.

In another embodiment, each $R_5$ is independently selected from —H, —$CH_3$, —$CF_3$, or —F.

In another embodiment, each $R_5$ is —H, i.e., the Substituted-Quinoxaline-Type Bridged-Piperidine Compound is a compound of Formula (IIA):

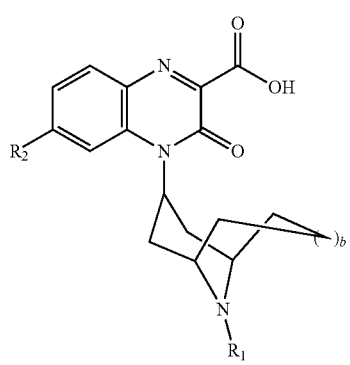

(IIA)

or a pharmaceutically acceptable derivative thereof where $R_1$, $R_2$, and b are defined above for the Substituted-Quinoxaline-Type Bridged-Piperidine Compounds of Formula (II).

In another embodiment, $R_2$ is -halo.

In another embodiment, $R_2$ is —F.

In another embodiment, the 3-oxo-3,4-dihydroquinoxaline-2-carboxylic acid portion of the Substituted-Quinoxaline-Type Bridged-Piperidine Compound is in the endo- or exo-conformation with respect to the bridge of the bridged piperidine.

In another embodiment, the 3-oxo-3,4-dihydroquinoxaline-2-carboxylic acid portion of the Substituted-Quinoxaline-Type Bridged-Piperidine Compound is in the endo-conformation with respect to the bridge of the bridged piperidine.

In another embodiment, the 3-oxo-3,4-dihydroquinoxaline-2-carboxylic acid portion of the Substituted-Quinoxaline-Type Bridged-Piperidine Compound is in the exo-conformation with respect to the bridge of the bridged piperidine.

In another embodiment, $R_1$ is —($C_9$-$C_{12}$)cycloalkyl or —($C_9$-$C_{12}$)bicycloalkyl.

In another embodiment, $R_1$ is —($C_9$-$C_{12}$)bicycloalkyl.

In another embodiment, $R_1$ is bicyclo[3.3.1]nonyl.

In another embodiment, $R_1$ is 1-bicyclo[3.3.1]nonyl, 2-bicyclo[3.3.1]nonyl, or 3-bicyclo[3.3.1]nonyl.

In another embodiment, $R_1$ is not 9-bicyclo[3.3.1]nonyl.

In another embodiment, $R_1$ is in the endo- or exo-conformation with respect to the bridge of the bridged piperidine.

In another embodiment, $R_1$ is in the endo-conformation with respect to the bridge of the bridged piperidine.

In another embodiment, $R_1$ is in the exo-conformation with respect to the bridge of the bridged piperidine.

In another embodiment, $R_1$ is:

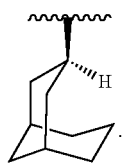

In another embodiment, $R_1$ is —($C_9$-$C_{12}$)cycloalkyl.

In another embodiment, $R_1$ is -cycloundecyl.

In another embodiment, b is 0, e.g., for a Substituted-Quinoxaline-Type Bridged-Piperidine Compound where each $R_5$ is —H, the bridged piperidine is:

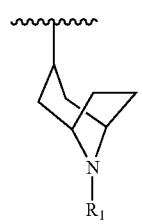

In another embodiment, b is 1, e.g., for a Substituted-Quinoxaline-Type Bridged-Piperidine Compound where each $R_5$ is —H, the bridged piperidine is:

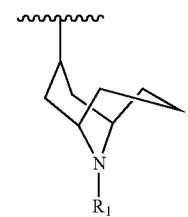

In another embodiment, the Substituted-Quinoxaline-Type Bridged-Piperidine Compound of Formula (IIA) is a Substituted-Quinoxaline-Type Bridged-Piperidine Compound of Formula (IIB):

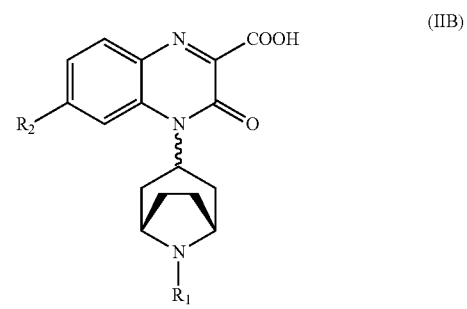

wherein $R_1$ and $R_2$ are as defined above for the Substituted-Quinoxaline-Type Bridged-Piperidine Compounds of Formula (II).

In another embodiment, the Substituted-Quinoxaline-Type Bridged-Piperidine Compound of Formula (IIA) is a Substituted-Quinoxaline-Type Bridged-Piperidine Compound of Formula (IIB1):

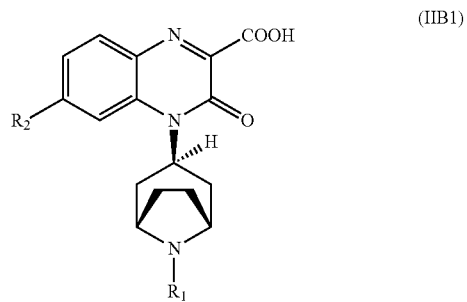

i.e., a Substituted-Quinoxaline-Type Bridged-Piperidine Compound of Formula (JIB) wherein the 6-membered, nitrogen-containing ring that is fused to the benzo is in the endo-conformation with respect to the (—$CH_2$—$CH_2$—) bridge of the bridged piperidine.

In another embodiment, the Substituted-Quinoxaline-Type Bridged-Piperidine Compound of Formula (IIA) is a Substituted-Quinoxaline-Type Bridged-Piperidine Compound of Formula (IIB2):

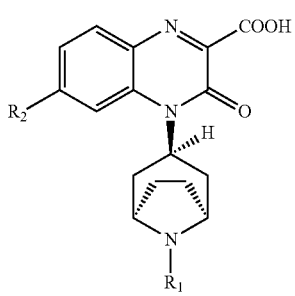

(IIB2)

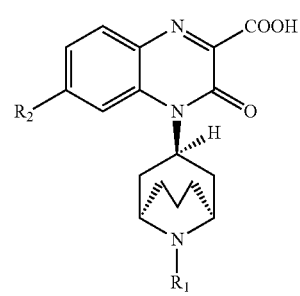

(IIC2)

i.e., a Substituted-Quinoxaline-Type Bridged-Piperidine Compound of Formula (IIB) wherein the 6-membered, nitrogen-containing ring that is fused to the benzo is in the exo-conformation with respect to the (—$CH_2$—$CH_2$—) bridge of the bridged piperidine.

In another embodiment, the Substituted-Quinoxaline-Type Bridged-Piperidine Compound of Formula (IIA) is a Substituted-Quinoxaline-Type Bridged-Piperidine Compound of Formula (IIC):

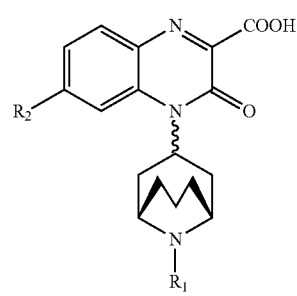

(IIC)

wherein $R_1$ and $R_2$ are as defined above for the Substituted-Quinoxaline-Type Bridged-Piperidine Compounds of Formula (II).

In another embodiment, the Substituted-Quinoxaline-Type Bridged-Piperidine Compound of Formula (IIA) is a Substituted-Quinoxaline-Type Bridged-Piperidine Compound of Formula (IIC1):

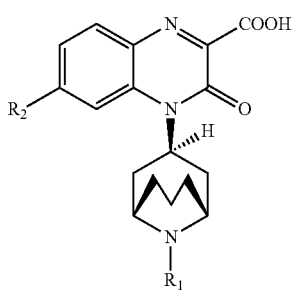

(IIC1)

i.e., a Substituted-Quinoxaline-Type Bridged-Piperidine Compound of Formula (IIC) wherein the 6-membered, nitrogen-containing ring that is fused to the benzo is in the endo-conformation with respect to the (—$CH_2$—$CH_2$—$CH_2$—) bridge of the bridged piperidine.

In another embodiment, the Substituted-Quinoxaline-Type Bridged-Piperidine Compound of Formula (IIA) is a Substituted-Quinoxaline-Type Bridged-Piperidine Compound of Formula (IIC2):

i.e., a Substituted-Quinoxaline-Type Bridged-Piperidine Compound of Formula (IIC) wherein the 6-membered, nitrogen-containing ring that is fused to the benzo is in the exo-conformation with respect to the (—$CH_2$—$CH_2$—$CH_2$—) bridge of the bridged piperidine.

In another embodiment, the pharmaceutically acceptable derivative is a hydrate.

In another embodiment, the pharmaceutically acceptable derivative is a pharmaceutically acceptable salt.

In another embodiment, the pharmaceutically acceptable salt is a p-toluenesulfonic acid salt, a sulfate salt, a phosphoric acid salt, or a hydrochloride salt.

In another embodiment, the pharmaceutically acceptable salt is a p-toluenesulfonic acid salt, a sulfate salt, or a phosphoric acid salt.

In another embodiment, the pharmaceutically acceptable salt is a p-toluenesulfonic acid salt.

As used in connection with the Substituted-Quinoxaline-Type Bridged-Piperidine Compounds herein, the terms used herein having following meaning:

"—$(C_1$-$C_4)$alkyl" means a straight chain or branched non-cyclic hydrocarbon having from 1 to 4 carbon atoms. Representative straight chain —$(C_1$-$C_4)$alkyls include -methyl, -ethyl, -n-propyl, and -n-butyl. Representative branched —$(C_1$-$C_4)$alkyls include -iso-propyl, -sec-butyl, -iso-butyl, and -tert-butyl.

"—$(C_1$-$C_3)$alkyl" means a straight chain or branched non-cyclic hydrocarbon having from 1 to 3 carbon atoms. Representative straight chain —$(C_1$-$C_3)$alkyls include -methyl, -ethyl, and -n-propyl. Representative branched —$(C_1$-$C_3)$ alkyls include -iso-propyl.

"—$(C_2$-$C_6)$alkenyl" means a straight chain or branched non-cyclic hydrocarbon having from 2 to 6 carbon atoms and including at least one carbon-carbon double bond. Representative straight chain and branched $(C_2$-$C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—$(C_2$-$C_6)$alkynyl" means a straight chain or branched non-cyclic hydrocarbon having from 2 to 6 carbon atoms and including at least one carbon-carbon triple bond. Representative straight chain and branched $(C_2$-$C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_9$-$C_{14})$cycloalkyl" means a saturated monocyclic hydrocarbon having from 9 to 14 carbon atoms. Representative $(C_9$-$C_{14})$cycloalkyls are -cyclononyl, -cyclodecyl, -cycloundecyl, -cyclododecyl, -cyclotridecyl, and -cyclotetradecyl.

"—$(C_{11}$-$C_{14})$cycloalkyl" means a saturated monocyclic hydrocarbon having from 11 to 14 carbon atoms. Representative (C₁₁-C₁₄)cycloalkyls are -cycloundecyl, -cyclododecyl, -cyclotridecyl, and -cyclotetradecyl.

"—(C₉-C₁₂)cycloalkyl" means a saturated monocyclic hydrocarbon having from 9 to 12 carbon atoms. Representative (C₉-C₁₂)cycloalkyls are -cyclononyl, -cyclodecyl, -cycloundecyl, and -cyclododecyl.

"—(C₃-C₆)cycloalkyl" means a saturated monocyclic hydrocarbon having from 3 to 6 carbon atoms. Representative (C₃-C₆)cycloalkyls include -cyclopropyl, -cyclobutyl, -cyclopentyl, and -cyclohexyl.

"—(C₉-C₁₄)bicycloalkyl" means a bi-cyclic hydrocarbon ring system having from 9 to 14 carbon atoms and at least one saturated cyclic alkyl ring. Representative —(C₉-C₁₄)bicycloalkyls include -indanyl, -bicyclo[3.3.1]nonyl, such as -1-bicyclo[3.3.1]nonyl, -2-bicyclo[3.3.1]nonyl, -3-bicyclo[3.3.1]nonyl and -9-bicyclo[3.3.1]nonyl, -bicyclo[4.2.1]nonyl, -1,2,3,4-tetrahydronaphthalenyl, -5,6,7,8-tetrahydronaphthalenyl, -perhydronaphthalenyl, -bicyclo[3.3.2]decyl, -bicyclo[4.2.2]decyl, -bicyclo[4.3.1]decyl, -bicyclo[3.3.3]undecyl, -bicyclo[4.3.2]undecyl, -bicyclo[6.2.1]undecyl, -bicyclo[4.3.3]dodecyl, -bicyclo[6.3.1]dodecyl, -bicyclo[6.3.1]dodeca-8,10-dienyl, -bicyclo[7.3.1]tridecyl, -bicyclo[7.2.2]tridecyl, -bicyclo[7.2.2]trideca-1(11), 9-dienyl, -bicyclo[9.1.1]tridecyl, -bicyclo[8.2.1]tridecyl, -bicyclo[7.3.2]tetradecyl, -bicyclo[8.3.1]tetradecyl, and the like.

"—(C₉-C₁₂)bicycloalkyl" means a bi-cyclic hydrocarbon ring system having from 9 to 12 carbon atoms and at least one saturated cyclic alkyl ring. Representative —(C₉-C₁₂)bicycloalkyls include -indanyl, -bicyclo[3.3.1]nonyl, such as -1-bicyclo[3.3.1]nonyl, -2-bicyclo[3.3.1]nonyl, -3-bicyclo[3.3.1]nonyl and -9-bicyclo[3.3.1]nonyl, -bicyclo[4.2.1]nonyl, -1,2,3,4-tetrahydronaphthalenyl, -5,6,7,8-tetrahydronaphthalenyl, -perhydronaphthalenyl, -bicyclo[3.3.2]decyl, -bicyclo[4.2.2]decyl, -bicyclo[4.3.1]decyl, -bicyclo[3.3.3]undecyl, -bicyclo[4.3.2]undecyl, -bicyclo[6.2.1]undecyl, -bicyclo[4.3.3]dodecyl, -bicyclo[6.3.1]dodecyl, -bicyclo[6.3.1]dodeca-8,10-dienyl, and the like.

"—(C₁₀-C₁₄)bicycloalkyl" means a bi-cyclic hydrocarbon ring system having from 10 to 14 carbon atoms and at least one saturated cyclic alkyl ring. Representative —(C₁₀-C₁₄)bicycloalkyls include -1,2,3,4-tetrahydronaphthalenyl, -5,6,7,8-tetrahydronaphthalenyl, -perhydronaphthalenyl, -bicyclo[3.3.2]decyl, -bicyclo[4.2.2]decyl, -bicyclo[4.3.1]decyl, -bicyclo[3.3.3]undecyl, -bicyclo[4.3.2]undecyl, -bicyclo[6.2.1]undecyl, -bicyclo[4.3.3]dodecyl, -bicyclo[6.3.1]dodecyl, -bicyclo[6.3.1]dodeca-8,10-dienyl, -bicyclo[7.3.1]tridecyl, -bicyclo[7.2.2]tridecyl, -bicyclo[7.2.2]trideca-1(11), 9-dienyl, -bicyclo[9.1.1]tridecyl, -bicyclo[8.2.1]tridecyl, -bicyclo[7.3.2]tetradecyl, -bicyclo[8.3.1]tetradecyl, and the like.

"—C(halo)₃" means a methyl group where each of the hydrogens of the methyl group has been replaced with a halogen. Representative —C(halo)₃ groups include —CF₃, —CCl₃, —CBr₃, and —CI₃.

"-Halogen" or "-halo" means —F, —Cl, —Br, or —I.

"Oxo", "=O", and the like as used herein mean an oxygen atom doubly bonded to carbon or another element.

"(C₂-C₃)bridge" as used herein means a hydrocarbon chain containing 2 or 3 carbon atoms joining the carbon atoms at positions 2 and 6 of the piperidine ring; for simplicity in some chemical structures herein A and B are illustrated as substituents of the piperidine ring with the understanding that A-B together form the (C₂-C₃)bridge. Exemplary compounds of the invention include those with an unsubstituted (C₂)bridge, i.e., —CH₂—CH₂—, joining positions 2 and 6 of the piperidine ring (A-B together form an unsubstituted (C₂)bridge) and an unsubstituted (C₃)bridge, i.e., —CH₂—CH₂—CH₂—, joining positions 2 and 6 of the piperidine ring (A-B together form an unsubstituted (C₃)bridge). Examples of compounds where A-B can together form a (C₂-C₃)bridge include compounds comprising the following ring systems: 8-aza-bicyclo[3.2.1]octane and 9-aza-bicyclo[3.3.1]nonane.

In compounds of the invention comprising bicyclo[3.3.1]nonyl as R₁, the bicyclo[3.3.1]nonyl can be attached to the nitrogen atom of the bridged piperidine in the following ways:

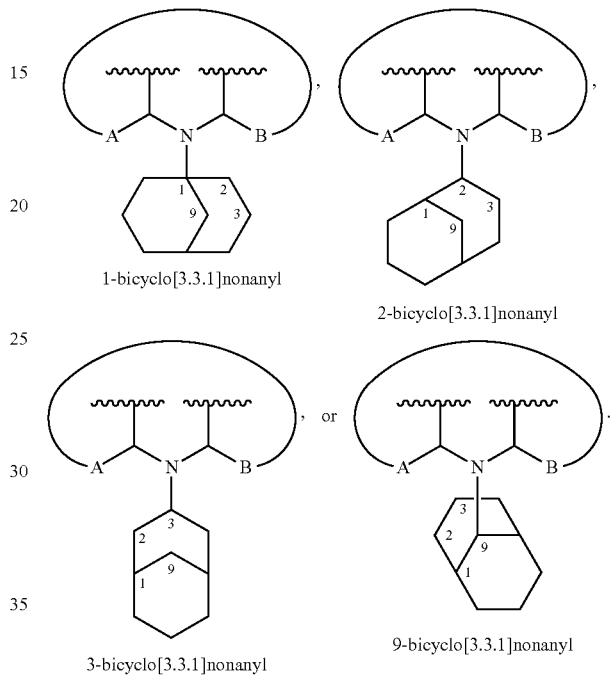

1-bicyclo[3.3.1]nonanyl 2-bicyclo[3.3.1]nonanyl 3-bicyclo[3.3.1]nonanyl 9-bicyclo[3.3.1]nonanyl In compounds of the invention, the exemplary endo bridge

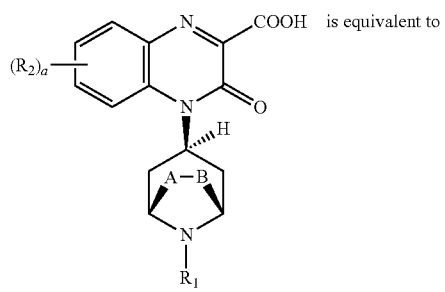

is equivalent to

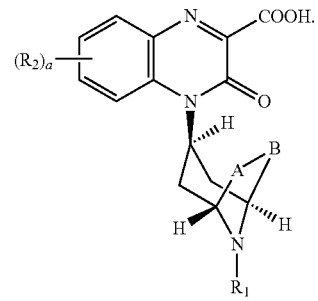

In such endo-compounds, the 3-oxo-3,4-dihydroquinoxaline-2-carboxylic acid portion of the compound, i.e.:

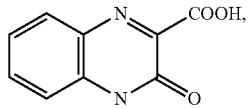 [SMILES: O=C(O)c1nc2ccccc2[nH]c1=O]

is in the endo-conformation with respect to the bridge of the bridged piperidine.

In compounds of the invention, the exemplary exo bridge

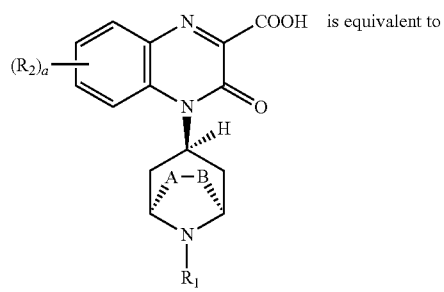

In such exo-compounds, the 3-oxo-3,4-dihydroquinoxaline-2-carboxylic acid portion of the compound is in the exo-conformation with respect to the bridge of the bridged piperidine.

In compounds of the invention where the —$R_1$ group comprises a bicyclic group, that bicyclic group can have two orientations. For example, for a —$R_1$ group that is a —$(C_9$-$C_{14})$bicycloalkyl, e.g., bicyclo[3.3.1]nonyl, attached directly to the piperidine ring nitrogen, the following orientations are possible:

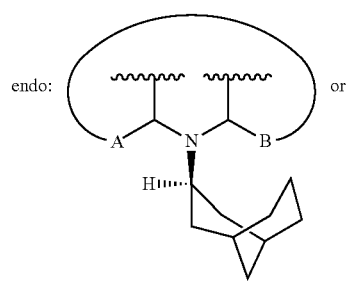

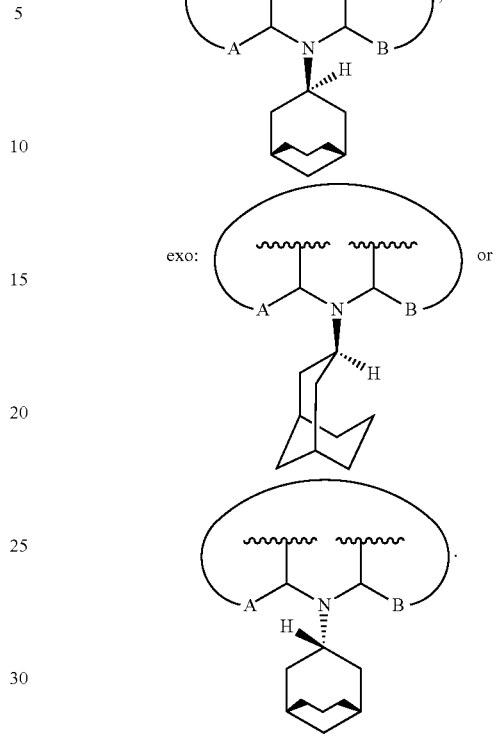

In such endo-compounds, the —$R_1$ group of the compound is in the endo-conformation with respect to the bridge of the bridged piperidine. In such exo-compounds, the —$R_1$ group of the compound is in the exo-conformation with respect to the bridge of the bridged piperidine.

When a first group is "substituted with one or more" second groups, one or more hydrogen atoms of the first group is replaced with a corresponding number of second groups. When the number of second groups is two or greater, each second group can be the same or different.

In one embodiment, a first group is substituted with up to three second groups.

In another embodiment, a first group is substituted with one or two second groups.

In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The phrase "pharmaceutically acceptable derivative", as used herein, includes any pharmaceutically acceptable salt, solvate, prodrug, radiolabeled, stereoisomer, enantiomer, diastereomer, other stereoisomeric form, racemic mixture, geometric isomer, and/or tautomer, e.g., of a Substituted-Quinoxaline-Type Bridged-Piperidine Compound of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a Substituted-Quinoxaline-Type Bridged-Piperidine Compound of the invention. In another embodiment, the pharmaceutically acceptable derivative is a pharmaceutically acceptable salt, e.g., of a Substituted-Quinoxaline-Type Bridged-Piperidine Compound of the invention.

The phrase "pharmaceutically acceptable salt", as used herein, is any pharmaceutically acceptable salt that can be prepared from a Substituted-Quinoxaline-Type Bridged-Piperidine Compound including a salt formed from an acid and a basic functional group, such as a nitrogen group, of a Substituted-Quinoxaline-Type Bridged-Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Substituted-Quinoxaline-Type Bridged-Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl, N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a Substituted-Quinoxaline-Type Bridged-Piperidine Compound can be prepared by reaction of the compounds with the appropriate acid via a variety of known methods.

The invention disclosed herein is also meant to encompass all solvates of the Substituted-Quinoxaline-Type Bridged-Piperidine Compounds. "Solvates" are known in the art and are considered to be a combination, physical association and/or solvation of a Substituted-Quinoxaline-Type Bridged-Piperidine Compound with a solvent molecule, e.g., a disolvate, monosolvate or hemisolvate when the solvent molecule: Substituted-Quinoxaline-Type Bridged-Piperidine Compound molecule ratio is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate", as used herein, encompasses both solution-phase and isolatable solvates. A Substituted-Quinoxaline-Type Bridged-Piperidine Compound of the invention can be present as a solvated form with a pharmaceutically acceptable solvent, such as water, methanol, ethanol, and the like, and it is intended that the invention include both solvated and unsolvated Substituted-Quinoxaline-Type Bridged-Piperidine Compound forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process involves dissolving the Substituted-Quinoxaline-Type Bridged-Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the Substituted-Quinoxaline-Type Bridged-Piperidine Compounds. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Substituted-Quinoxaline-Type Bridged-Piperidine Compound of Formula (I), Formula (I') or Formula (II) which is readily convertible in vivo, e.g., by being metabolized, into the required Substituted-Quinoxaline-Type Bridged-Piperidine Compound of Formula (I), Formula (I') or Formula (II). Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a Substituted-Quinoxaline-Type Bridged-Piperidine Compound can be replaced by an isotope of the hydrogen, carbon or other atoms. Such a "radiolabeled", "radiolabeled form", and the like of a Substituted-Quinoxaline-Type Bridged-Piperidine Compound, each of which is encompassed by the invention, is useful as a research and/or diagnostic tool in metabolism pharmacokinetic studies and in binding assays. Examples of isotopes that can be incorporated into a Substituted-Quinoxaline-Type Bridged-Piperidine Compound of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of Formula I can be prepared by introducing tritium into the particular compound of Formula I, for example, by catalytic dehalogenation with tritium. This method can include reacting a suitably halogen-substituted precursor of a compound of Formula (I), Formula (I') or Formula (II) with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol.* 1, *Labeled Compounds (Part A)*, Chapter 6 (1987). $^{14}$C-labeled compounds can be prepared by employing starting materials having a $^{14}$C carbon.

A Substituted-Quinoxaline-Type Bridged-Piperidine Compound can contain one or more asymmetric centers and can thus give rise to enantiomers, diastereomers, and other stereoisomeric forms. The invention is also meant to encompass all such possible forms as well as their racemic and resolved forms or any mixture thereof. When a Substituted-Quinoxaline-Type Bridged-Piperidine Compound contains an olefinic double bond or other center of geometric asymmetry, and unless specified otherwise, it is intended to include all "geometric isomers", e.g., both E and Z geometric isomers. All "tautomers", e.g., ketone-enol, amide-imidic acid, lactam-lactim, enamine-imine, amine-imine, and enamine-enimine tautomers, are intended to be encompassed by the invention as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a Substituted-Quinoxaline-Type Bridged-Piperidine Compound can be obtained by known techniques such as chiral chromatography or formation of diastereomeric salts from an optically active acid or base.

The phrase "effective amount", when used in connection with a Substituted-Quinoxaline-Type Bridged-Piperidine Compound, means an amount effective for: (a) treating or preventing a Condition; (b) detectably inhibiting ORL-1 receptor function in a cell; or (c) detectably activating ORL-1 receptor function in a cell.

The phrase "effective amount", when used in connection with a second therapeutic agent means an amount for providing the therapeutic effect of the therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compounds that binds to a receptor but produces no regulatory effect, but rather blocks binding of another agent to the receptor is defined as an "antagonist". (See Ross and Kenakin, *Pharmacodynamics: Mechanisms of Drug Action and the Relationship Between Drug Concentration and Effect*, Chapter 2 in *Goodman & Gilman's The Pharmacological Basis of Therapeutics* 31-32 (J. G. Hardman, L. E. Limbird and A. Goodman-Gilman eds., 10$^{th}$ Ed. 2001).

The term "MeOH" means methanol, i.e., methyl alcohol.

The term "EtOH" means ethanol, i.e., ethyl alcohol.

The term "Et$_2$O" means diethyl ether, i.e., ethoxyethane.

The term "THF" means tetrahydrofuran.

The term "DMF" means N,N-dimethylformamide.

The term "DCM" means methylene chloride, i.e., dichloromethane or CH$_2$Cl$_2$.

The term "DCE" means dichloroethane, i.e., 1,1-dichloroethane.

The term "EtOAc" means ethyl acetate.

The term "MeCN" means acetonitrile.

The term "DME" means dimethoxyethane, i.e., 1,2-dimethoxyethane.

The term "DMSO" means dimethylsulfoxide, i.e., methylsulfinylmethane.

The term "AcOH" means acetic acid.

The term "TEA" means triethylamine.

The term "NaH" means sodium hydride.

The term "TsOH" means p-toluene sulfonic acid, i.e., toluene-4-sulfonic acid.

The term "DPPA" means diphenyl phosphorazidate, i.e., diphenyl phosphoryl azide.

The term "TFA" means trifluoroacetic acid, i.e., 2,2,2-trifluoroacetic acid.

The term "TFAA" means trifluoroacetic anhydride, i.e., 2,2,2-trifluoroacetic anhydride.

The term "Bn" means benzyl, i.e.

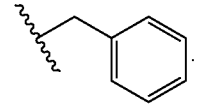

The term "BOC" means tert-butyloxycarbonyl, i.e.

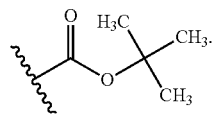

The term "CBZ" means benzyloxycarbonyl, i.e.

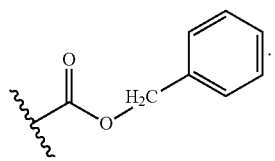 [SMILES: *C(=O)OCc1ccccc1]

The term "IBD" means inflammatory-bowel disease.

The term "IBS" means irritable-bowel syndrome.

The term "ALS" means amyotrophic lateral sclerosis.

The phrases "treatment of", "treating", and the like include the amelioration or cessation of a Condition or a symptom thereof. In one embodiment, treating includes inhibiting, for example, decreasing the overall frequency of episodes of a Condition or a symptom thereof.

The phrases "prevention of", "preventing", and the like include the avoidance of the onset of a Condition or a symptom thereof.

A "disorder" includes, but is not limited to, the Conditions defined above.

4.5 Methods for Making the Substituted-Quinoxaline-Type Bridged-Piperidine Compounds The invention relates to methods for preparing Substituted-Quinoxaline-Type Bridged-Piperidine Compounds and/or pharmaceutically acceptable derivatives thereof, such as illustrated in the synthetic Schemes below. The Substituted-Quinoxaline-Type Bridged-Piperidine Compounds can be made using conventional organic synthesis, in view of the present disclosure, and including the following illustrative methods shown in the schemes below where $R_1$, $R_2$ and a are defined above, A and B are as defined in connection with a $(C_2-C_3)$bridge, L is a halogen leaving group such as Br or I, L' is F or Cl, and R is $-(C_1-C_4)$alkyl or $-CF_3$.

Scheme A

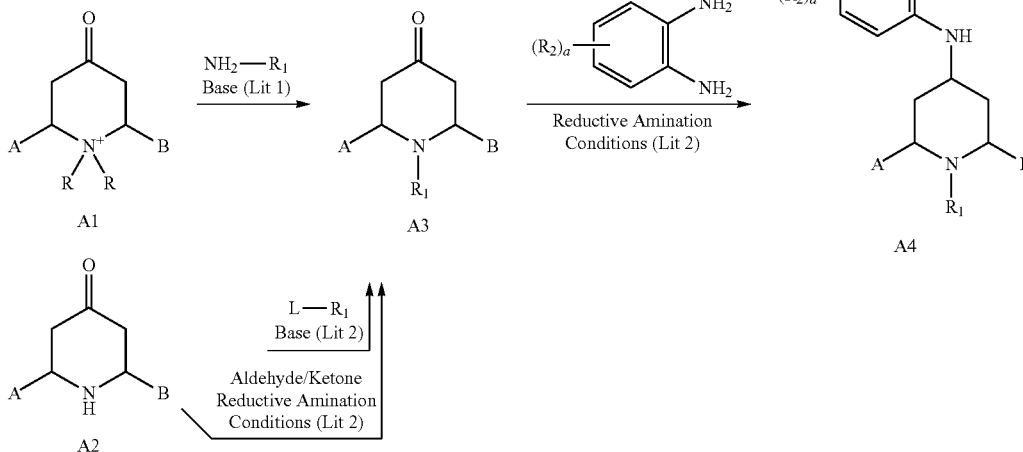

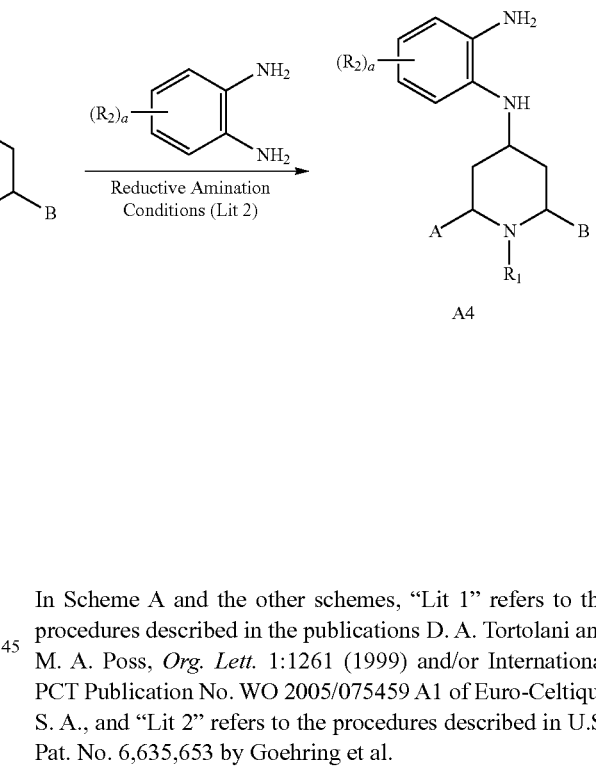

In Scheme A and the other schemes, "Lit 1" refers to the procedures described in the publications D. A. Tortolani and M. A. Poss, *Org. Lett.* 1:1261 (1999) and/or International PCT Publication No. WO 2005/075459 A1 of Euro-Celtique S. A., and "Lit 2" refers to the procedures described in U.S. Pat. No. 6,635,653 by Goehring et al.

Compounds of formula A1 and A2 are commercially available or can be prepared by methods known to the art.

A piperidinium salt of structure A1 can be reacted with a primary amine in a suitable solvent such as EtOH under reflux conditions in the presence of a base such as $K_2CO_3$ as described in reference "Lit 1" to provide the 1-(substituted) Bridged-Piperidine-4-one compound A3. As described in reference "Lit 2," compound A3 can also be prepared by alkylation of a Bridged-Piperidine-4-one of structure A2 with an alkyl bromide or alkyl iodide in a suitable solvent such as DMF, MeCN or DMSO in the presence of an inorganic base such as $K_2CO_3$ or an organic base such as diisopropylethylamine. As described in reference "Lit 2," compound A3 can also be prepared by reductive amination of compound A2 with an aldehyde or ketone using either sodium triacetoxyborohydride or sodium cyanoborohydride in a suitable solvent such as DCM or MeOH, respectively. Compound A3 can then be reductively aminated with a substituted or unsubstituted 1,2-phenylenediamine using sodium triacetoxyborohydride or sodium cyanoborohydride in a suitable solvent such as DCM or MeOH, respectively, to provide compound M, as described in reference "Lit 2."

conditions, such as MeOH or EtOH at a temperature from about 0° C. to about 25° C. Upon completion of hydrolysis, the reaction mixture is neutralized, e.g., with dilute HCl, to provide compound F2.

Scheme F

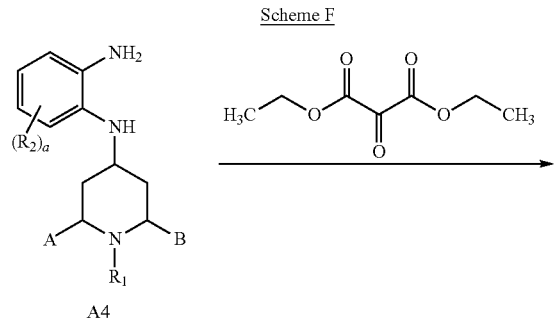

A4

Scheme H

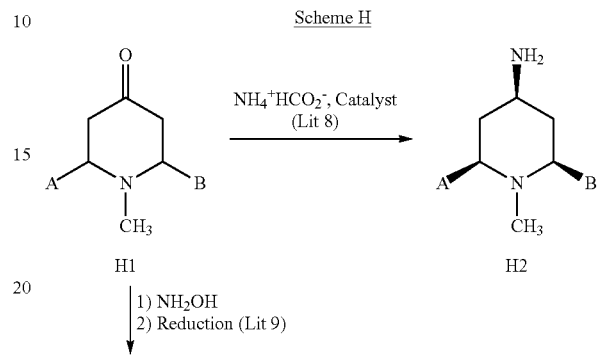

H1    H2

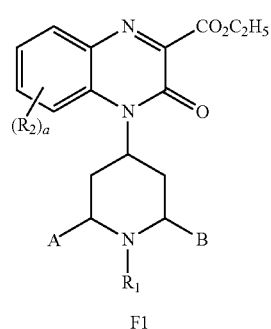

F1

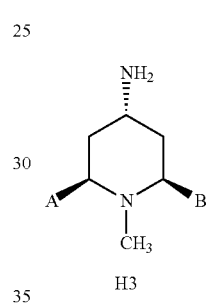

H3

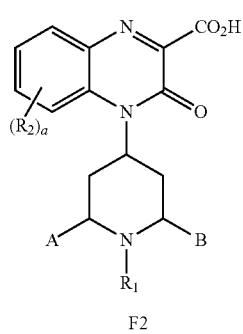

F2

Compound A4 and diethyl 2-oxomalonate can be dissolved in a solvent with a high boiling point, such as toluene or xylene, and heated under reflux conditions with azeotropic removal of water to provide compound F1. Compound F1 can be hydrolyzed to the carboxylic acid F2 by treatment with a base, such as aqueous NaOH, in a solvent under appropriate In Scheme H and the other schemes, "Lit 8" refers to "A Modified Palladium Catalyzed Reductive Amination Procedure," Berdini et al., *Tetrahedron*, 58:5669-5674 (2002) and "Lit 9" refers to "Molecular Features Associated with Polyamine Modulation of NMDA Receptors," A. H. Lewin et al., *J. Med. Chem.* 41:988-995 (1998).

The compound of formula H1, wherein substituent groups A and B together form a bridge, e.g., a two carbon bridge, is commercially available or can be prepared by methods known to the art.

When substituent groups A and B together form a bridge, e.g., a two carbon bridge, compound H1 can be converted to compound H2, the "endo" isomer, under reductive amination conditions using, e.g., ammonium formate and a noble metal catalyst, e.g., palladium on carbon, in a solvent such as EtOH or MeOH as described in reference "Lit 8." Similarly, where substituent groups A and B together form a bridge, e.g., a two carbon bridge, compound H1 can be reacted with aqueous hydroxylamine in a solvent such as hexanes to form an intermediate hydroxylamine, which can be converted to its oxime by dehydration in a solvent with a high boiling point such as toluene, under Dean-stark conditions. The oxime intermediate can be converted to compound H3, the "exo" isomer, by reduction using, e.g., sodium in propanol as described in reference "Lit 9."

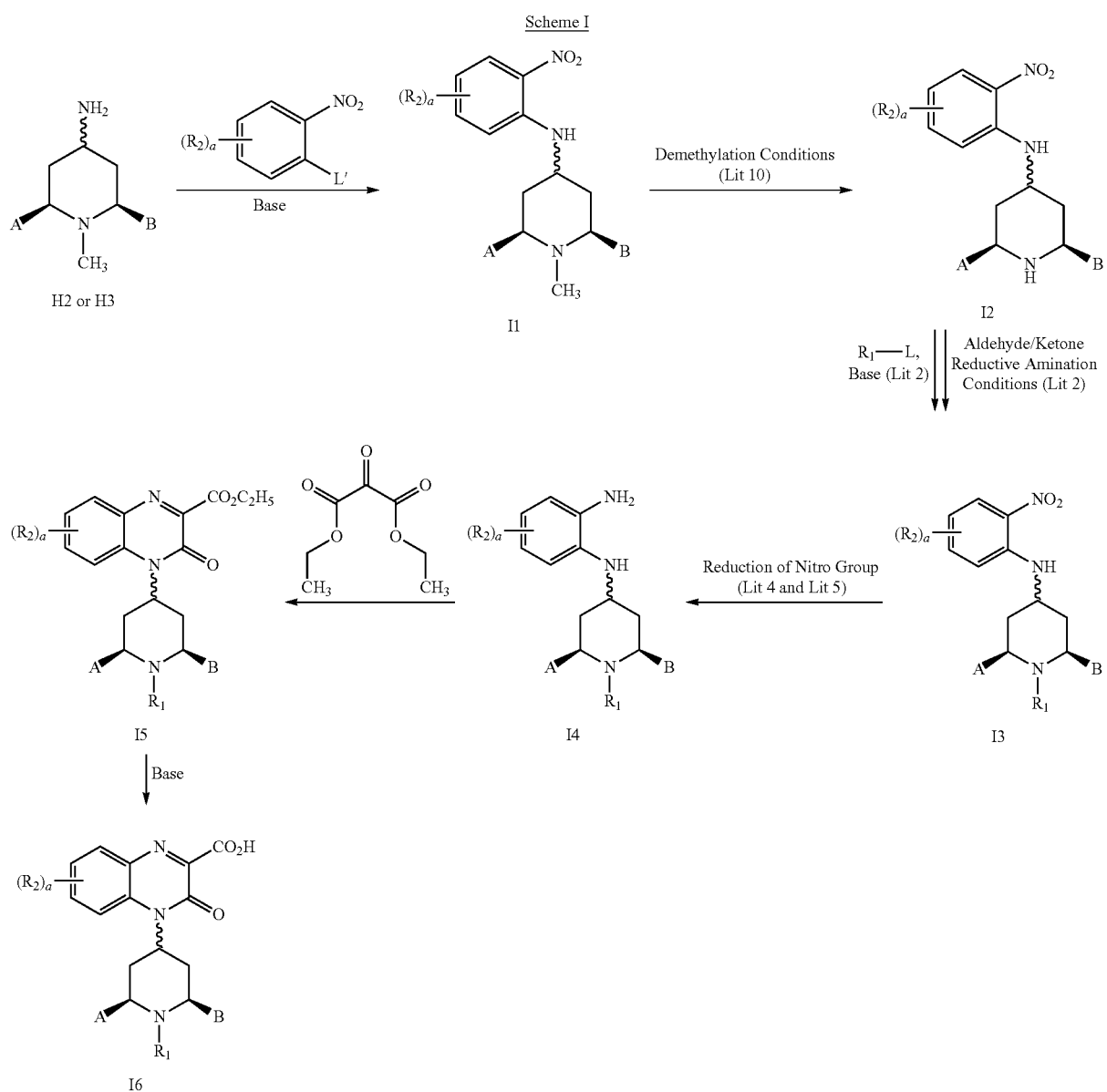

In Scheme I and the other schemes, "Lit 4" refers to the reference P. N. Rylander, *Hydrogenation Methods*, Academic Press, 104-116 (1985), which provides a review of the methods available for the reduction of nitro groups, "Lit 5" refers to the Zinin reduction procedures described in the reference Porter, *Organic Reactions*, 20:455-481 (1973), and "Lit 10" refers to the procedures described by R. A. Olofson et al, in *J. Org. Chem.*, 49:2081-2082 (1984) and to R. A. Olofson et al, in *Tetrahedron Let.*, 18:1571 (1977).

Substituted-Quinoxaline-Type Bridged-Piperidine Compounds such as I6 where substituent groups A and B together form a bridge, e.g., a two carbon bridge, can be prepared as described in Scheme I. Compound H2 (the "endo" isomer) or H3 (the "exo" isomer) (where substituent groups A and B together form a bridge, e.g., a two carbon bridge) can be converted to compound I1 by reaction with a substituted or unsubstituted 2-halo-1-nitrobenzene (where the halo is fluoride or chloride) and a base such as $K_2CO_3$, in a suitable solvent such as DMF or MeCN at a temperature from about 20° C. to about 100° C. Compound I1 can be demethylated to give compound I2 using, e.g., 1-chloromethylchloroformate in a solvent such as 1,2-dichloroethane, followed by treatment with MeOH as described in "Lit 10." Compound I2 can be converted to compound I3 (similar to steps described in reference "Lit 2" in Scheme A). Compound I3 can be converted to compound I4 by hydrogenation using a catalyst under a hydrogen atmosphere or by chemical means using a reducing agent similar to steps described in "Lit 4" and "Lit 5". Compound I4 can be converted to compound I5 by reaction with diethyl 2-oxomalonate in a solvent with a high boiling point such as toluene or xylene under reflux conditions. Compound I5 can be converted to the carboxylic acid derivative I6 by hydrolysis using a base such as aqueous NaOH in a suitable solvent such as MeOH or EtOH, followed by neutralization using an acid such as dilute HCl.

Scheme L
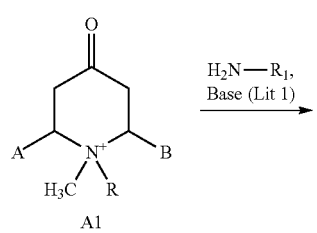
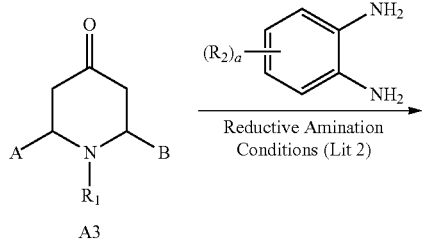
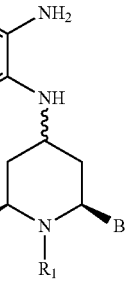
Compound I4 can be prepared, as shown in Scheme L, from compound A1 (similar to steps described in Scheme A). Where substituent groups A and B of compound I4 form a bridge, e.g., a two carbon bridge, the two isomers, "exo" and "endo," can be separated by chromatography and can be separately converted to compounds such as F1, F2, and the like as described earlier in Scheme F.
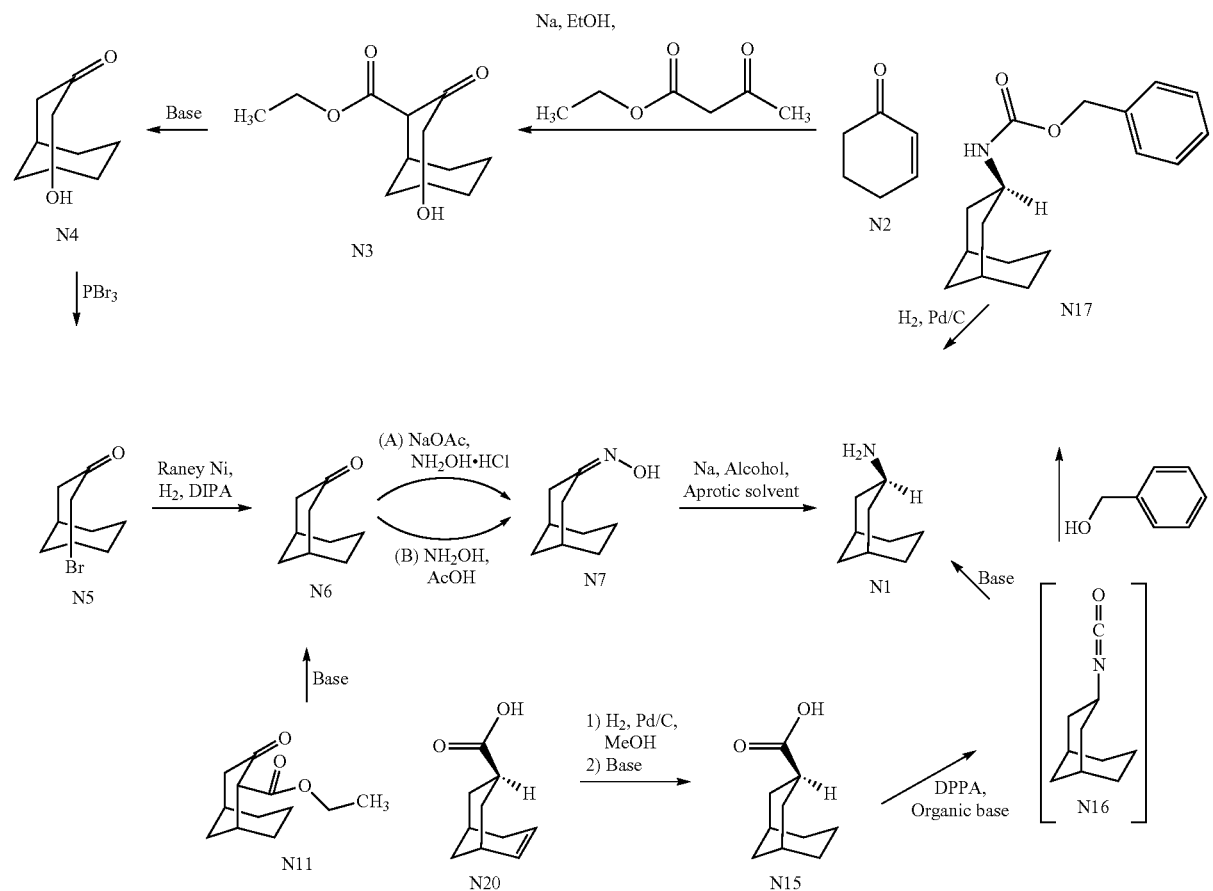

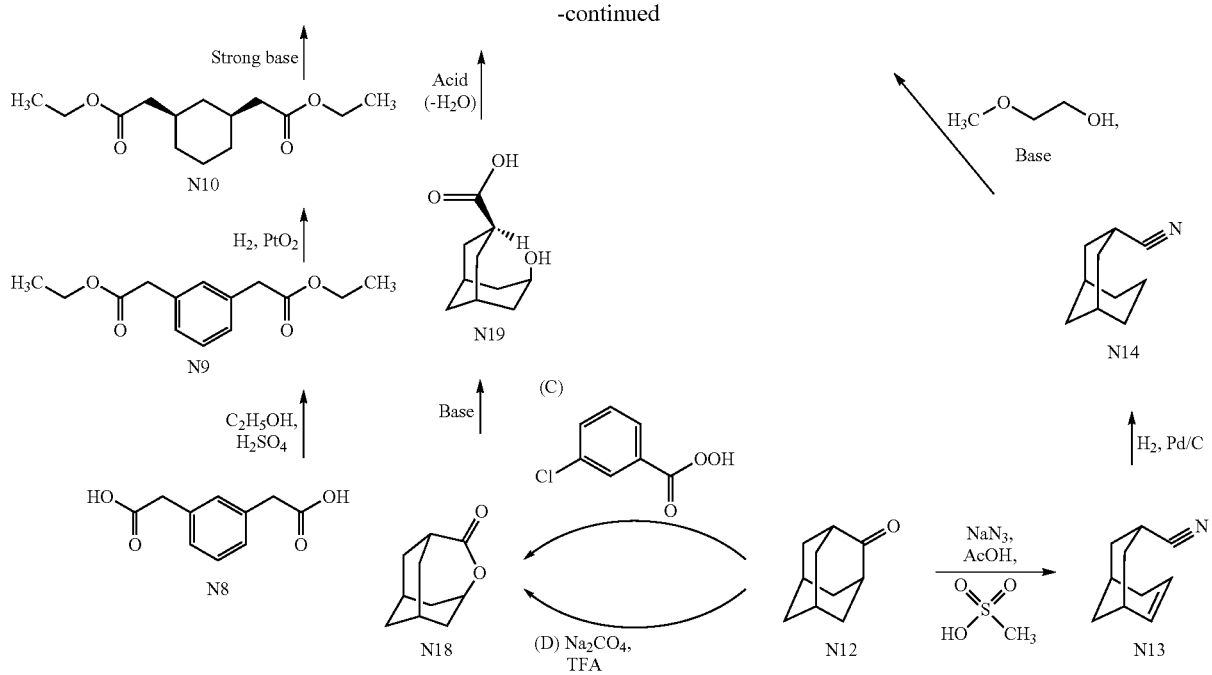

As shown in Scheme N, compound N1, which can comprise an $R_1$ group, can be prepared by a number of synthetic routes. For example, taking into account the procedures disclosed in "Improved synthetic methods for bicyclo[3.3.1]nonan-3-one," Momose et al., *Chem. Pharmaceut. Bull.* 26(1):288-295 (1978), compound N2 can be reacted with ethyl 3-oxobutanoate and a base, such as sodium ethoxide or potassium tert-butoxide which is optionally formed from metallic sodium and the corresponding alcohol, in an alcoholic solvent, such as MeOH or EtOH, under reflux for from about 24 h to about 48 h to provide compound N3. Compound N3 can be converted to compound N4 using a base, such as NaOH or KOH, in a solvent, such as MeOH or EtOH, and water at a temperature of from about 70° C. to about 100° C. for from about 4 h to about 6 h. Compound N4 can be reacted with phosphorus tribromide in a nonpolar solvent, such as DCM, 1,2-dichloroethane or $CHCl_3$, at a temperature of from about 0° C. to about 25° C. to provide compound N5, which can immediately be treated with Raney nickel and diisopropylamine in a solvent, such as THF or DME, under an atmosphere of hydrogen to provide compound N6.

Thereafter, compound N6 can be reacted with hydroxylamine or a salt thereof and a base, such as sodium acetate, in a solvent, such as EtOH, to provide compound N7 (shown as "(A)" in Scheme N). Alternatively, compound N7 can be prepared from compound N6 using an aqueous solution of hydroxylamine and a weak acid, such as acetic acid, in a solvent, such as THF, DME or 1,4-dioxane (shown as "(B)" in Scheme N). Compound N7 can be converted to compound N1 using an alkali metal, such as sodium or potassium, and an alcohol, such as EtOH or isopropanol, in an inert solvent, such as toluene or xylene, at a temperature of from about 100° C. to about 130° C.

If desired, taking into account the procedures provided in H. K. Hall, *J. Org. Chem.* 28:3213-3214 (1963), compound N6 can be prepared from compound N8, 2,2'-(1,3-phenylene) diacetic acid. Compound N8 can be converted to the diethyl ester using, for example, oxalyl chloride, thionyl chloride or sulfuric acid, in an inert solvent, such as DCM, followed by treatment with EtOH. The ester compound N9 can be dissolved in a solvent, such as acetic acid, and treated with a catalyst, such as a platinum metal catalyst, e.g., platinum oxide, under from about 1 atm to about 10 atm hydrogen gas pressure to provide compound N10 as a mixture of cis and trans isomers with a preponderance of the cis isomer. Compound N10 can be dissolved in a solvent, such as THF, DME or 1,4-dioxane, and reacted with a strong base, such as sodium hydride or potassium tert-butoxide, at a temperature of from about 50° C. to about 100° C. to provide compound N11, which can be converted to compound N6 using a strong base, such as NaOH or KOH, in a solvent, such as MeOH or EtOH.

Alternatively, compound N1 can be prepared from compound N12, adamantane-2-one. By one route, compound N12 can be converted to compound N15 via compounds N13 and N14 by using procedures provided in J. A. Peters, J. M. Van Der Toorn and H. Van Bekkumm, *Tetrahedron* 31:2273-2281 (1975). Compound N15 can be converted to compound N17 using the Curtius rearrangement procedure provided in "Diphenylphosphoryl azide a new convenient reagent for a modified Curtius rearrangement and for peptide synthesis," T. Shioiri, K. Ninomiya, S. Yamada, *J. Amer. Chem. Soc.* 94:6202-6205 (1972), whereby compound N15 is reacted with diphenyl phosphoryl azide and an organic base, such as triethylamine, in an inert solvent, such as benzene or toluene, at a temperature of about 70° C. to provide intermediate isocyanate compound N16 which, upon reaction with benzyl alcohol, provides compound N17. Compound N17 can be converted to compound N1 by hydrogenolysis using a catalyst, such as a platinum group metal catalyst, e.g., palladium on charcoal, in a solvent such as MeOH or EtOH under a hydrogen atmosphere.

If desired, compound N1 can be prepared from compound N15 by synthesizing intermediate isocyanate compound N16 as described above then reacting it with a base, such as aqueous NaOH or aqueous KOH, in a solvent, such as THF, at a temperature of from about −5° C. to about 0° C. to provide compound N1, which can be isolated as either its hydrochloride or diphenyl phosphate salt.

If desired, compound N18 can be prepared from compound N12 by reaction of compound N12 with 3-chlorobenzoperoxoic acid in a solvent, such as CHCl$_3$ or DCM, at a temperature of about 25° C. (shown as "(C)" in Scheme N). Alternatively, compound N18 can be prepared from compound N12 using sodium percarbonate in trifluoroacetic acid as solvent and reagent at a temperature of from about 25° C. to about 40° C. (shown as "(D)" in Scheme N). Compound N18 can be converted to compound N19 by using a base, such as NaOH or KOH, in water and a solvent, such as MeOH, EtOH or 2-methoxyethanol, under reflux for from about 24 h to about 48 h. Compound N19 can be converted to compound N20 by acid catalyzed dehydration using, for example, p-toluene sulfonic acid or methane sulfonic acid, in a solvent, such as toluene or xylene. Compound N20 can be converted to compound N15 by hydrogenation using a catalyst, such as palladium on charcoal, in MeOH followed by treatment of the product with NaOH or KOH in water.

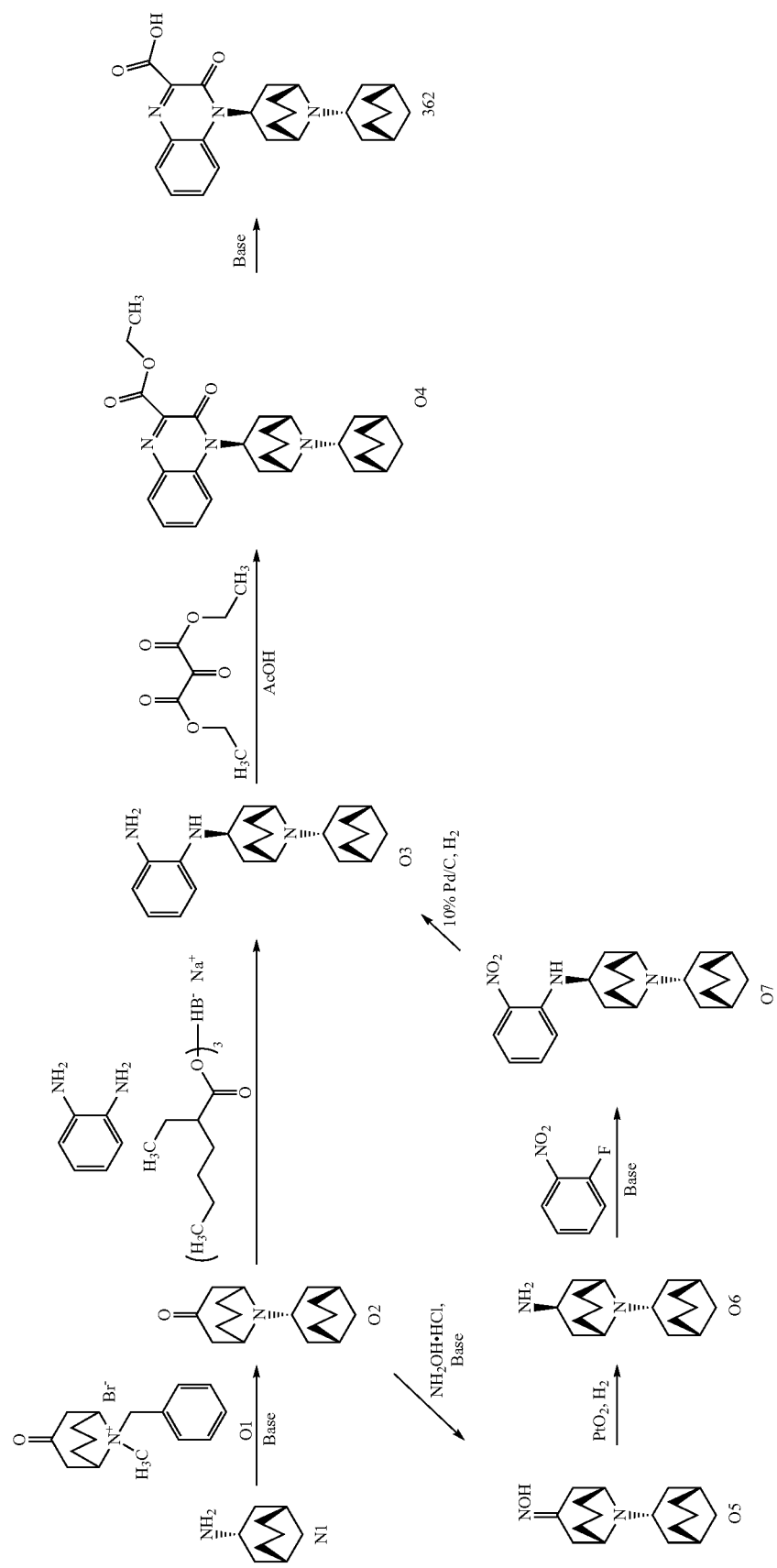

As shown in Scheme O, an exemplary Substituted Quinoxaline-Type Bridged-Piperidine Compound comprising an $R_1$ group formed from compound N1 can be prepared by a number of synthetic routes. For purposes of exemplification only, while the product illustrated in Scheme O is Substituted Quinoxaline-Type Bridged-Piperidine Compound 362, as those in the art will recognize this scheme is of course non-limiting and applicable to the preparation of other Substituted Quinoxaline-Type Bridged-Piperidine Compounds. For example, compound N1, its hydrochloride, or its diphenylphosphate salt can be reacted with compound O1, pseudopelletierine benzylbromide salt, in a solvent, such as EtOH and water, and a base, such as $K_2CO_3$ or $Na_2CO_3$, at a temperature of from about 25° C. to about 100° C. to provide compound O2. Compound O2 can be converted to compound O3 by treatment with excess 1,2-phenylenediamine and a sterically hindered reducing agent, such as sodium tris-(2-ethylhexanoyl)borohydride, in a solvent, such as DCM, at a temperature of from about 25° C. to about 40° C. Compound O3 can be converted to compound O4 by reaction with diethyl 2-oxomalonate and acetic acid in a solvent, such as toluene or xylene, at a temperature of from about 80° C. to about 110° C. Compound O4 can be converted to the exemplary Substituted Quinoxaline-Type Bridged-Piperidine Compound 362 using a base, such as NaOH or KOH, in water and a solvent, such as MeOH, EtOH or THF.

Alternatively, compound O3 can be prepared from compound O2 in a four step procedure as follows. Compound O2 can be reacted with hydroxylamine hydrochloride in a base, such as an inorganic base, e.g., sodium acetate, or an organic base, e.g., pyridine, in a solvent, such as EtOH, to provide oxime compound O5. Compound O5 can be reduced to the endo amine isomer compound O6 in good stereoselectivity by using a catalyst, such as a platinum group metal catalyst, e.g., platinum oxide or palladium on charcoal, in a solvent, such as acetic acid, under an atmosphere of from about 1 atm to about 5 atm of hydrogen. Compound O6 can be converted to compound O7 by reaction with a 1-halo-2-nitrobenzene, such as 2-fluoro-nitrobenzene or 2-chloro-nitrobenzene, and a base, such as $K_2CO_3$ or TEA, in a solvent, such as DMF, N-methylpyrrolidone, MeCN or 1,4-dioxane, at a temperature of from about 100° C. to about 110° C. Compound O7 can be converted to compound O3 under hydrogenation conditions using a catalyst, such as Raney nickel, palladium on charcoal or platinum oxide, in a solvent, such as MeOH or EtOH.

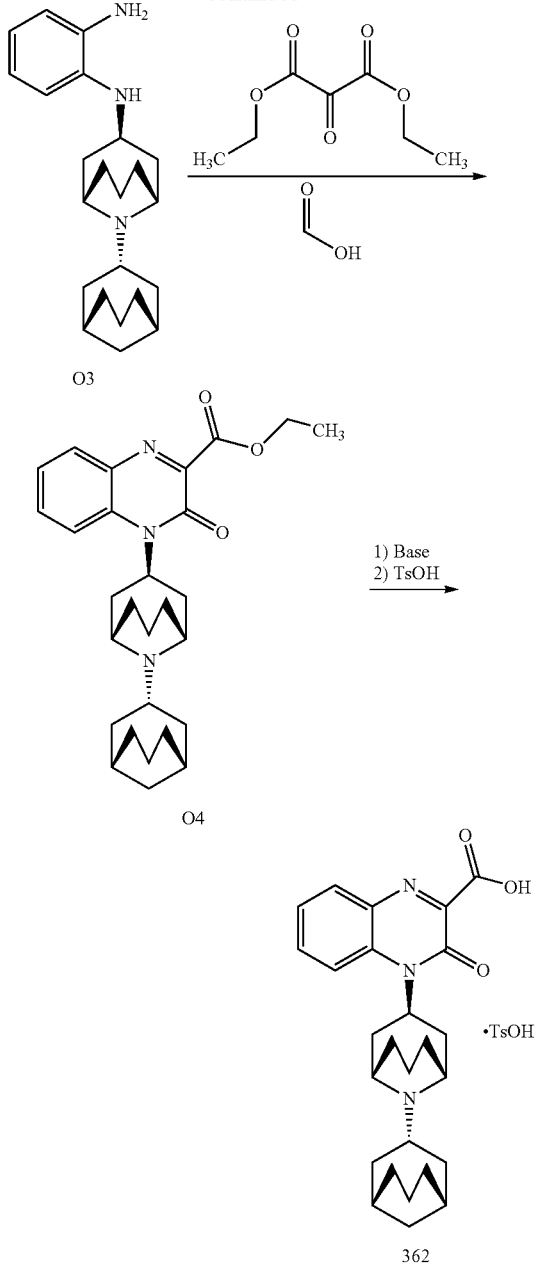

Alternatively, as shown in Scheme P an exemplary Substituted Quinoxaline-Type Bridged-Piperidine Compound comprising an $R_1$ group formed from compound N1 can be prepared by a method beginning with a two-step, "one-pot" procedure for converting compound O2 to compound O3. For purposes of exemplification only, while the product illustrated in Scheme P is Substituted Quinoxaline-Type Bridged-Piperidine Compound 362, as those in the art will recognize this scheme is of course non-limiting and applicable to the preparation of other Substituted Quinoxaline-Type Bridged-Piperidine Compounds. Compound O2 can be reacted with an excess of 1,2-phenylenediamine, from 1.2 to 3.0 equivalents, and acetic acid in a solvent, such as THF or DME (diglyme), and the intermediate imine (comprising a C=N group) can immediately be reacted with a reducing agent, such as sodium triacetoxyborohydride, to provide compound O3. Compound O3 can be converted to compound O4 by reaction with diethyl 2-oxomalonate and formic acid in a solvent, such as toluene or xylene, at a temperature of from about 80° C. to about 110° C. Compound O4 can be converted to the exemplary Substituted Quinoxaline-Type Bridged-Piperidine Compound by reaction with a base, such as NaOH or KOH, in water and a co-solvent, such as THF or DME. After the reaction is complete, excess TsOH in THF can be added to provide the tosylate salt of the exemplary Substituted Quinoxaline-Type Bridged-Piperidine Compound 362.

4.6 Therapeutic Uses of the Substituted-Quinoxaline-Type Bridged-Piperidine Compounds In accordance with the invention, the Substituted-Quinoxaline-Type Bridged-Piperidine Compounds are administered to an animal in need of treatment or prevention of a Condition.

In one embodiment, an effective amount of a Substituted-Quinoxaline-Type Bridged-Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to, pain (CNS effect), memory disorders, obesity, constipation, depression, dementia, and Parkinsonism.

In another embodiment, an effective amount of a Substituted-Quinoxaline-Type Bridged-Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Substituted-Quinoxaline-Type Bridged-Piperidine Compounds can be used to treat or prevent acute or chronic pain. Examples of pain that can be treated or prevented using a Substituted-Quinoxaline-Type Bridged-Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Substituted-Quinoxaline-Type Bridged-Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Substituted-Quinoxaline-Type Bridged-Piperidine Compound can be used to treat or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Substituted-Quinoxaline-Type Bridged-Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Substituted-Quinoxaline-Type Bridged-Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Substituted-Quinoxaline-Type Bridged-Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

According to the invention, some of the Substituted-Quinoxaline-Type Bridged-Piperidine Compounds are agonists at the ORL-1 receptor, some of the Substituted-Quinoxaline-Type Bridged-Piperidine Compounds are partial agonists at the ORL-1 receptor, and some of the Substituted-Quinoxaline-Type Bridged-Piperidine Compounds are antagonists at the ORL-1 receptor. In another embodiment, a Substituted-Quinoxaline-Type Bridged-Piperidine Compound is an agonist at the ORL-1 receptor and an agonist at a µ, κ and/or δ opioid receptor, particularly at a g opioid receptor. In another embodiment, a Substituted-Quinoxaline-Type Bridged-Piperidine Compound is a partial agonist at the ORL-1 receptor and an agonist at a µ, κ and/or δ opioid receptor, particularly at a g opioid receptor. In another embodiment, a Substituted-Quinoxaline-Type Bridged-Piperidine Compound is an antagonist at the ORL-1 receptor and an agonist at µ, κ and/or δ opioid receptor, particularly at a µ opioid receptor. In another embodiment, a Substituted-Quinoxaline-Type Bridged-Piperidine Compound is an agonist at the ORL-1 receptor and an antagonist at µ, κ and/or δ opioid receptor, particularly at a µ opioid receptor. In another embodiment, a Substituted-Quinoxaline-Type Bridged-Piperidine Compound is a partial agonist at the ORL-1 receptor and an antagonist at a µ, κ and/or δ opioid receptor, particularly at a µ opioid receptor. In another embodiment, a Substituted-Quinoxaline-Type Bridged-Piperidine Compound is an antagonist at the ORL-1 receptor and an antagonist at a µ, κ and/or δ opioid receptor, particularly at a µ opioid receptor.

The invention also provides methods for inhibiting ORL-1 receptor function in a cell, comprising contacting a cell capable of expressing the ORL-1 receptor with an amount of a Substituted-Quinoxaline-Type Bridged-Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Substituted-Quinoxaline-Type Bridged-Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The invention also relates to methods for activating ORL-1 receptor function in a cell, comprising contacting a cell capable of expressing the ORL-1 receptor with an amount of a Substituted-Quinoxaline-Type Bridged-Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Substituted-Quinoxaline-Type Bridged-Piperidine Compound. In one embodiment the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Y. Shimohigashi et al., "Sensitivity of opioid receptor-like receptor ORL1 for chemical modification on nociceptin, a naturally occurring nociceptive peptide," *J. Biol. Chem.* 271(39):23642-23645 (1996); M. Narita et al., "Identification of the G-protein coupled ORL1 receptor in the mouse spinal cord by [$^{35}$S]-GTPγS binding and immunohistochemistry," *Brit. J. Pharmacol.* 128:1300-1306 (1999); G. Milligan, "Principles: Extending then utility of [$^{35}$S]GTPγS binding assays," *TIPS* 14: 87-90 (2003): and S. Lazareno, "Measurement of agonist-stimulated [$^{35}$S]GTPγS binding to cell membranes," *Methods in Molecular Biology* Vol. 106:231-1245 (1999).

4.7 Therapeutic/Prophylactic Administration and Compositions of the Invention Due to their activity, the Substituted-Quinoxaline-Type Bridged-Piperidine Compounds are advantageously useful in human and veterinary medicine. As described above, the Substituted-Quinoxaline-Type Bridged-Piperidine Compounds are useful for treating or preventing a Condition in an animal in need thereof. The Substituted-Quinoxaline-Type Bridged-Piperidine Compounds of the invention can be administered to any animal requiring modulation of the opioid and/or ORL-1 receptors.

When administered to an animal, a Substituted-Quinoxaline-Type Bridged-Piperidine Compound can be administered as a component of a composition that comprises a pharmaceutically acceptable carrier or excipient. The invention compositions, which comprise a Substituted-Quinoxaline-Type Bridged-Piperidine Compound, can be administered orally. A Substituted-Quinoxaline-Type Bridged-Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Substituted-Quinoxaline-Type Bridged-Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a Substituted-Quinoxaline-Type Bridged-Piperidine Compound into the bloodstream.

In specific embodiments, it can be desirable to administer a Substituted-Quinoxaline-Type Bridged-Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Substituted-Quinoxaline-Type Bridged-Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Substituted-Quinoxaline-Type Bridged-Piperidine Compound can be formulated as a suppository, with traditional binders and excipients such as triglycerides.

When a Substituted-Quinoxaline-Type Bridged-Piperidine Compound of the invention is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Substituted-Quinoxaline-Type Bridged-Piperidine Compound of the invention can also be in the form of a powder for reconstitution as an injectable formulation.

In another embodiment, a Substituted-Quinoxaline-Type Bridged-Piperidine Compound can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In yet another embodiment, a Substituted-Quinoxaline-Type Bridged-Piperidine Compound can be delivered in a controlled-release system or sustained-release system (see, e.g., Goodson, "Dental Applications" (pp. 115-138) in *Medical Applications of Controlled Release, Vol. 2, Applications and Evaluation*, R. S. Langer and D. L. Wise eds., CRC Press (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Langer and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Substituted-Quinoxaline-Type Bridged-Piperidine Compound, e.g., the spinal column, brain, or gastrointestinal tract, thus requiring only a fraction of the systemic dose.

The invention compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Substituted-Quinoxaline-Type Bridged-Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

The invention compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Substituted-Quinoxaline-Type Bridged-Piperidine Compounds are formulated in accordance with routine procedures as a composition adapted for oral administration to human beings. A Substituted-Quinoxaline-Type Bridged-Piperidine Compound to be orally delivered can be in the form of tablets, capsules, gelcaps, caplets, lozenges, aqueous or oily solutions, suspensions, granules, powders, emulsions, syrups, or elixirs, for example. When a Substituted-Quinoxaline-Type Bridged-Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems*, (Lieberman, Rieger and Banker, eds.) published by Marcel Dekker, Inc.

When a Substituted-Quinoxaline-Type Bridged-Piperidine Compound is to be injected parenterally, it can be, e.g., in the form of an isotonic sterile solution. Alternatively, when a Substituted-Quinoxaline-Type Bridged-Piperidine Compound is to be inhaled, it can be formulated into a dry aerosol or can be formulated into an aqueous or partially aqueous solution.

An orally administered Substituted-Quinoxaline-Type Bridged-Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Substituted-Quinoxaline-Type Bridged-Piperidine Compounds can be formulated for intravenous administration. Typically, compositions for intravenous administration comprise sterile isotonic aqueous buffer. Where necessary, the compositions can also include a solubilizing agent. A Substituted-Quinoxaline-Type Bridged-Piperidine Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Substituted-Quinoxaline-Type Bridged-Piperidine Compound is to be administered by infusion, it can be dispensed, for example, with an infusion bottle containing sterile pharmaceutical grade water or saline. Where a Substituted-Quinoxaline-Type Bridged-Piperidine Compound is administered by injection, an ampule of sterile water for injection or saline can be provided so that the ingredients can be mixed prior to administration.

A Substituted-Quinoxaline-Type Bridged-Piperidine Compound can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Substituted-Quinoxaline-Type Bridged-Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Substituted-Quinoxaline-Type Bridged-Piperidine Compound, and can thus reduce the occurrence of adverse side effects.

Controlled- or sustained-release compositions can initially release an amount of a Substituted-Quinoxaline-Type Bridged-Piperidine Compound that promptly produces the desired therapeutic or prophylactic effect, and gradually and continually release other amounts of the Substituted-Quinoxaline-Type Bridged-Piperidine Compound to maintain this level of therapeutic or prophylactic effect over an extended period of time. To maintain a constant level of the Substituted-Quinoxaline-Type Bridged-Piperidine Compound in the body, the Substituted-Quinoxaline-Type Bridged-Piperidine Compound can be released from the dosage form at a rate that will replace the amount of Substituted-Quinoxaline-Type Bridged-Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Substituted-Quinoxaline-Type Bridged-Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Substituted-Quinoxaline-Type Bridged-Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Substituted-Quinoxaline-Type Bridged-Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Substituted-Quinoxaline-Type Bridged-Piperidine Compound in vitro, the amount effective for inhibiting or activating that receptor function in a cell will typically range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Substituted-Quinoxaline-Type Bridged-Piperidine Compound will be from about 0.01 μL to about 1 mL. In another embodiment, the volume of solution or suspension will be about 200 μL.

The Substituted-Quinoxaline-Type Bridged-Piperidine Compounds will have a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

Typically, the Substituted-Quinoxaline-Type Bridged-Piperidine Compounds will have a Ki (nM) of about 300 or less for binding to ORL-1 receptors. In one embodiment, the Substituted-Quinoxaline-Type Bridged-Piperidine Compounds of the invention will have a Ki (nM) of about 100 or less. In another embodiment, the Substituted-Quinoxaline-Type Bridged-Piperidine Compounds of the invention will have a Ki (nM) of about 35 or less. In another embodiment, the Substituted-Quinoxaline-Type Bridged-Piperidine Compounds of the invention will have a Ki (nM) of about 20 or less. In another embodiment, the Substituted-Quinoxaline-Type Bridged-Piperidine Compounds of the invention will have a Ki (nM) of about 15 or less. In another embodiment, the Substituted-Quinoxaline-Type Bridged-Piperidine Compounds of the invention will have a Ki (nM) of about 10 or less. In another embodiment, the Substituted-Quinoxaline-Type Bridged-Piperidine Compounds of the invention will have a Ki (nM) of about 4 or less. In another embodiment, the Substituted-Quinoxaline-Type Bridged-Piperidine Compounds of the invention will have a Ki (nM) of about 1 or less. In another embodiment, the Substituted-Quinoxaline-Type Bridged-Piperidine Compounds of the invention will have a Ki (nM) of about 0.4 or less. In another embodiment, the Substituted-Quinoxaline-Type Bridged-Piperidine Compounds of the invention will have a Ki (nM) of about 0.1 or less.

ORL-1 GTP $EC_{50}$ is the concentration of a compound providing 50% of the maximal response for the compound at an ORL-1 receptor. Substituted-Quinoxaline-Type Bridged-Piperidine Compounds typically will have an ORL-1 GTP $EC_{50}$ (nM) of about 5000 or less to stimulate ORL-1 receptor function. In one embodiment, the Substituted-Quinoxaline-Type Bridged-Piperidine Compounds of the invention will have an ORL-1 GTP $EC_{50}$ (nM) of about 1000 or less. In another embodiment, the Substituted-Quinoxaline-Type Bridged-Piperidine Compounds of the invention will have an ORL-1 GTP $EC_{50}$ (nM) of about 100 or less. In another embodiment, the Substituted-Quinoxaline-Type Bridged-Piperidine Compounds of the invention will have an ORL-1 GTP $EC_{50}$ (nM) of about 80 or less. In another embodiment, the Substituted-Quinoxaline-Type Bridged-Piperidine Compounds of the invention will have an ORL-1 GTP $EC_{50}$ (nM) of about 50 or less. In another embodiment, the Substituted-Quinoxaline-Type Bridged-Piperidine Compounds of the invention will have an ORL-1 GTP $EC_{50}$ (nM) of about 35 or less. In another embodiment, the Substituted-Quinoxaline-Type Bridged-Piperidine Compounds of the invention will have an ORL-1 GTP $EC_{50}$ (nM) of about 15 or less. In another embodiment, the Substituted-Quinoxaline-Type Bridged-Piperidine Compounds will have an ORL-1 GTP $EC_{50}$ (nM) of about 10 or less. In another embodiment, the Substituted-Quinoxaline-Type Bridged-Piperidine Compounds will have an ORL-1 GTP $EC_{50}$ (nM) of about 4 or less. In another embodiment, the Substituted-Quinoxaline-Type Bridged-Piperidine Compounds will have an ORL-1 GTP $EC_{50}$ (nM) of about 1 or less. In another embodiment, the Substituted-Quinoxaline-Type Bridged-Piperidine Compounds will have an ORL-1 GTP $EC_{50}$ (nM) of about 0.4 or less. In another embodiment, the Substituted-Quinoxaline-Type Bridged-Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. Typically, a Substituted-Quinoxaline-Type Bridged-Piperidine Compound of the invention acting as an agonist will have an ORL-1 GTP Emax (%) of about 50% or greater. In one embodiment, agonist Substituted-Quinoxaline-Type Bridged-Piperidine Compounds will have an ORL-1 GTP Emax (%) of about 75% or greater. In another embodiment, agonist Substituted-Quinoxaline-Type Bridged-Piperidine Compounds will have an ORL-1 GTP Emax (%) of about 85% or greater. In another embodiment, agonist Substituted-Quinoxaline-Type Bridged-Piperidine Compounds will have an ORL-1 GTP Emax (%) of about 95% or greater. In another embodiment, agonist Substituted-Quinoxaline-Type Bridged-Piperidine Compounds will have an ORL-1 GTP Emax (%) of about 100% or greater. Typically, a Substituted-Quinoxaline-Type Bridged-Piperidine Compound of the invention acting as a partial agonist will have an ORL-1 GTP Emax (%) of less than about 10%. In one embodiment, partial agonist Substituted-Quinoxaline-Type Bridged-Piperidine Compounds will have an ORL-1 GTP Emax (%) of less than about 20%. In another embodiment, partial agonist Substituted-Quinoxaline-Type Bridged-Piperidine Compounds will have an ORL-1 GTP Emax (%) of less than about 30%. In another embodiment, partial agonist Substituted-Quinoxaline-Type Bridged-Piperidine Compounds will have an ORL-1 GTP Emax (%) of less than about 40%. In another embodiment, partial agonist Substituted- Quinoxaline-Type Bridged-Piperidine Compounds will have an ORL-1 GTP Emax (%) of less than about 50%.

The Substituted-Quinoxaline-Type Bridged-Piperidine Compounds will have a binding affinity (Ki) for the human μ-opioid receptors of about 3000 nM or less in one embodiment, or about 1000 nM or less in another embodiment, or about 525 nM or less in another embodiment, or about 100 nM or less in another embodiment, or about 50 nM or less in another embodiment, or about 20 nM or less in another embodiment, or about 5 nM or less in another embodiment.

Typically, the Substituted-Quinoxaline-Type Bridged-Piperidine Compounds will have a Ki (nM) of about 3000 or less for binding to μ-opioid receptors. In one embodiment, the Substituted-Quinoxaline-Type Bridged-Piperidine Compounds of the invention will have a Ki (nM) of about 1000 or less. In another embodiment, the Substituted-Quinoxaline-Type Bridged-Piperidine Compounds of the invention will have a Ki (nM) of about 650 or less. In another embodiment, the Substituted-Quinoxaline-Type Bridged-Piperidine Compounds of the invention will have a Ki (nM) of about 525 or less. In another embodiment, the Substituted-Quinoxaline-Type Bridged-Piperidine Compounds of the invention will have a Ki (nM) of about 250 or less. In another embodiment, the Substituted-Quinoxaline-Type Bridged-Piperidine Compounds of the invention will have a Ki (nM) of about 100 or less. In another embodiment, the Substituted-Quinoxaline-Type Bridged-Piperidine Compounds of the invention will have a Ki (nM) of about 10 or less. In another embodiment, the Substituted-Quinoxaline-Type Bridged-Piperidine Compounds of the invention will have a Ki (nM) of about 1 or less.

μ GTP $EC_{50}$ is the concentration of a compound providing 50% of the maximal response for the compound at a μ-opioid receptor. Substituted-Quinoxaline-Type Bridged-Piperidine Compounds typically will have a μ GTP $EC_{50}$ (nM) of about 5000 or less to stimulate μ-opioid receptor function. In one embodiment, the Substituted-Quinoxaline-Type Bridged-Piperidine Compounds of the invention will have a μ GTP $EC_{50}$ (nM) of about 4100 or less. In another embodiment, the Substituted-Quinoxaline-Type Bridged-Piperidine Compounds of the invention will have a μ GTP $EC_{50}$ (nM) of about 3100 or less. In another embodiment, the Substituted-Quinoxaline-Type Bridged-Piperidine Compounds of the invention will have a μ GTP $EC_{50}$ (nM) of about 2000 or less. In another embodiment, the Substituted-Quinoxaline-Type Bridged-Piperidine Compounds of the invention will have a μ GTP $EC_{50}$ (nM) of about 1000 or less. In another embodiment, the Substituted-Quinoxaline-Type Bridged-Piperidine Compounds of the invention will have a μ GTP $EC_{50}$ (nM) of about 100 or less. In another embodiment, the Substituted-Quinoxaline-Type Bridged-Piperidine Compounds will have a μ GTP $EC_{50}$ (nM) of about 10 or less. In another embodiment, the Substituted-Quinoxaline-Type Bridged-Piperidine Compounds will have a μ GTP $EC_{50}$ (nM) of about 1 or less. In another embodiment, the Substituted-Quinoxaline-Type Bridged-Piperidine Compounds will have a μ GTP $EC_{50}$ (nM) of about 0.4 or less.

μ GTP Emax (%) is the maximal effect elicited by a compound relative to the effect elicited by DAMGO, a standard μ agonist. Typically, the Substituted-Quinoxaline-Type Bridged-Piperidine Compounds of the invention will have a μ GTP Emax (%) of about 10% or greater. In one embodiment, the Substituted-Quinoxaline-Type Bridged-Piperidine Compounds will have a μ GTP Emax (%) of about 20% or greater. In another embodiment, the Substituted-Quinoxaline-Type Bridged-Piperidine Compounds will have a μ GTP Emax (%) of about 50% or greater. In another embodiment, the Substituted-Quinoxaline-Type Bridged-Piperidine Compounds will have a μ GTP Emax (%) of about 65% or greater. In another embodiment, the Substituted-Quinoxaline-Type Bridged-Piperidine Compounds will have a μ GTP Emax (%) of about 75% or greater. In another embodiment, the Substituted-Quinoxaline-Type Bridged-Piperidine Compounds will have a μ GTP Emax (%) of about 88% or greater.

Typically, the Substituted-Quinoxaline-Type Bridged-Piperidine Compounds will have a Ki (nM) of about 20,000 or less for κ receptors. In one embodiment, the Substituted-Quinoxaline-Type Bridged-Piperidine Compounds will have substantially no activity. In another embodiment, the Substituted-Quinoxaline-Type Bridged-Piperidine Compounds will have a Ki (nM) of about 10,000 or less. In another embodiment, the Substituted-Quinoxaline-Type Bridged-Piperidine Compounds will have a Ki (nM) of about 5000 or less. In another embodiment, the Substituted-Quinoxaline-Type Bridged-Piperidine Compounds will have a Ki (nM) of about 1000 or less. In another embodiment, the Substituted-Quinoxaline-Type Bridged-Piperidine Compounds will have a Ki (nM) of about 500 or less. In another embodiment, the Substituted-Quinoxaline-Type Bridged-Piperidine Compounds will have a Ki (nM) of about 300 or less. In another embodiment, the Substituted-Quinoxaline-Type Bridged-Piperidine Compounds will have a Ki (nM) of about 100 or less. In another embodiment, the Substituted-Quinoxaline-Type Bridged-Piperidine Compounds will have a Ki (nM) of about 50 or less. In another embodiment, the Substituted-Quinoxaline-Type Bridged-Piperidine Compounds will have a Ki (nM) of about 20 or less. In another embodiment, the Substituted-Quinoxaline-Type Bridged-Piperidine Compounds will have a Ki (nM) of about 15 or less.

κ GTP $EC_{50}$ is the concentration of a compound providing 50% of the maximal response for the compound at a κ receptor. Substituted-Quinoxaline-Type Bridged-Piperidine Compounds typically will have a κ GTP $EC_{50}$ (nM) of about 20,000 or less to stimulate κ opioid receptor function. In one embodiment, the Substituted-Quinoxaline-Type Bridged-Piperidine Compounds will have a κ GTP $EC_{50}$ (nM) of about 10,000 or less. In another embodiment, the Substituted-Quinoxaline-Type Bridged-Piperidine Compounds will have a κ GTP $EC_{50}$ (nM) of about 5000 or less. In another embodiment, the Substituted-Quinoxaline-Type Bridged-Piperidine Compounds will have a κ GTP $EC_{50}$ (nM) of about 2000 or less. In another embodiment, the Substituted-Quinoxaline-Type Bridged-Piperidine Compounds will have a κ GTP $EC_{50}$ (nM) of about 1500 or less. In another embodiment, the Substituted-Quinoxaline-Type Bridged-Piperidine Compounds will have a κ GTP $EC_{50}$ (nM) of about 800 or less. In another embodiment, the Substituted-Quinoxaline-Type Bridged-Piperidine Compounds will have a κ GTP $EC_{50}$ (nM) of about 500 or less. In another embodiment, the Substituted-Quinoxaline-Type Bridged-Piperidine Compounds will have a κ GTP $EC_{50}$ (nM) of about 300 or less. In another embodiment, the Substituted-Quinoxaline-Type Bridged-Piperidine Compounds will have a κ GTP $EC_{50}$ (nM) of about 100 or less. In another embodiment, the Substituted-Quinoxaline-Type Bridged-Piperidine Compounds will have a κ GTP $EC_{50}$ (nM) of about 50 or less. In another embodiment, the Substituted-Quinoxaline-Type Bridged-Piperidine Compounds will have a κ GTP $EC_{50}$ (nM) of about 25 or less.

κ GTP Emax (%) is the maximal effect elicited by a compound relative to the effect elicited by U69,593. Typically, the Substituted-Quinoxaline-Type Bridged-Piperidine Compounds of the invention will have a κ GTP Emax (%) of about 10% or greater. In one embodiment, the Substituted-Quinoxaline-Type Bridged-Piperidine Compounds will have a κ GTP Emax (%) of about 15% or greater. In another embodiment, the Substituted-Quinoxaline-Type Bridged-Piperidine Compounds will have a κ GTP Emax (%) of about 30% or greater. In another embodiment, the Substituted-Quinoxaline-Type Bridged-Piperidine Compounds will have a κ GTP Emax (%) of about 40% or greater. In another embodiment, the Substituted-Quinoxaline-Type Bridged-Piperidine Compounds will have a κ GTP Emax (%) of about 45% or greater. In another embodiment, the Substituted-Quinoxaline-Type Bridged-Piperidine Compounds will have a κ GTP Emax (%) of about 75% or greater. In another embodiment, the Substituted-Quinoxaline-Type Bridged-Piperidine Compounds will have a κ GTP Emax (%) of about 90% or greater.

Typically, the Substituted-Quinoxaline-Type Bridged-Piperidine Compounds will have a Ki (nM) of about 20,000 or less for δ receptors. In one embodiment, the Substituted-Quinoxaline-Type Bridged-Piperidine Compounds will have substantially no activity. In another embodiment, the Substituted-Quinoxaline-Type Bridged-Piperidine Compounds will have a Ki (nM) of about 10,000 or less. In another embodiment, the Substituted-Quinoxaline-Type Bridged-Piperidine Compounds will have a Ki (nM) of about 9000 or less. In another embodiment, the Substituted-Quinoxaline-Type Bridged-Piperidine Compounds will have a Ki (nM) of about 7500 or less. In another embodiment, the Substituted-Quinoxaline-Type Bridged-Piperidine Compounds will have a Ki (nM) of about 6500 or less. In another embodiment, the Substituted-Quinoxaline-Type Bridged-Piperidine Compounds will have a Ki (nM) of about 5000 or less. In another embodiment, the Substituted-Quinoxaline-Type Bridged-Piperidine Compounds will have a Ki (nM) of about 3000 or less. In another embodiment, the Substituted-Quinoxaline-Type Bridged-Piperidine Compounds will have a Ki (nM) of about 2500 or less. In another embodiment, the Substituted-Quinoxaline-Type Bridged-Piperidine Compounds will have a Ki (nM) of about 1000 or less. In another embodiment, the Substituted-Quinoxaline-Type Bridged-Piperidine Compounds will have a Ki (nM) of about 500 or less. In another embodiment, the Substituted-Quinoxaline-Type Bridged-Piperidine Compounds will have a Ki (nM) of about 350 or less. In another embodiment, the Substituted-Quinoxaline-Type Bridged-Piperidine Compounds will have a Ki (nM) of about 250 or less. In another embodiment, the Substituted-Quinoxaline-Type Bridged-Piperidine Compounds will have a Ki (nM) of about 100 or less.

δ GTP $EC_{50}$ is the concentration of a compound providing 50% of the maximal response for the compound at a δ receptor. Substituted-Quinoxaline-Type Bridged-Piperidine Compounds typically will have a δ GTP $EC_{50}$ (nM) of about 20,000 or less to stimulate δ opioid receptor function. In one embodiment, the Substituted-Quinoxaline-Type Bridged-Piperidine Compounds will have a δ GTP $EC_{50}$ (nM) of about 10,000 or less. In another embodiment, the Substituted-Quinoxaline-Type Bridged-Piperidine Compounds will have a δ GTP $EC_{50}$ (nM) of about 1000 or less. In another embodiment, the Substituted-Quinoxaline-Type Bridged-Piperidine Compounds will have a δ GTP $EC_{50}$ (nM) of about 100 or less. In another embodiment, the Substituted-Quinoxaline-Type Bridged-Piperidine Compounds will have a δ GTP $EC_{50}$ (nM) of about 90 or less. In another embodiment, the Substituted-Quinoxaline-Type Bridged-Piperidine Compounds will have a δ GTP $EC_{50}$ (nM) of about 50 or less. In another embodiment, the Substituted-Quinoxaline-Type Bridged-Piperidine Compounds will have a δ GTP $EC_{50}$ (nM) of about 25 or less.

δ GTP Emax (%) is the maximal effect elicited by a compound relative to the effect elicited by met-enkephalin. Typically, the Substituted-Quinoxaline-Type Bridged-Piperidine Compounds of the invention will have a δ GTP Emax (%) of about 10% or greater. In one embodiment, the Substituted-Quinoxaline-Type Bridged-Piperidine Compounds will have a δ GTP Emax (%) of about 30% or greater. In another embodiment, the Substituted-Quinoxaline-Type Bridged-Piperidine Compounds will have a δ GTP Emax (%) of about 50% or greater. In another embodiment, the Substituted-Quinoxaline-Type Bridged-Piperidine Compounds will have a δ GTP Emax (%) of about 75% or greater. In another embodiment, the Substituted-Quinoxaline-Type Bridged-Piperidine Compounds will have a δ GTP Emax (%) of about 90% or greater. In another embodiment, the Substituted-Quinoxaline-Type Bridged-Piperidine Compounds will have a δ GTP Emax (%) of about 100% or greater.

The Substituted-Quinoxaline-Type Bridged-Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Substituted-Quinoxaline-Type Bridged-Piperidine Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. In one embodiment of the invention, where a second therapeutic agent is administered to an animal for treatment of a Condition (e.g., pain), the minimal effective amount of the Substituted-Quinoxaline-Type Bridged-Piperidine Compound will be less than its minimal effective amount would be where the second therapeutic agent is not administered. In this embodiment, the Substituted-Quinoxaline-Type Bridged-Piperidine Compound and the second therapeutic agent can act synergistically to treat or prevent a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout*, in *Goodman & Gilman's The Pharmacological Basis of Therapeutics* 617-57 (P. B. Molinhoff and R. W. Ruddon eds., 9th ed 1996), and G. R. Hanson, *Analgesic, Antipyretic and Anti-Inflammatory Drugs in Remington: The Science and Practice of Pharmacy Vol II* 1196-1221 (A. R. Gennaro ed. 19th ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A Substituted-Quinoxaline-Type Bridged-Piperidine Compound and the second therapeutic agent combined can act either additively or synergistically to treat the same Condition, or they may act independently of each other such that the Substituted-Quinoxaline-Type Bridged-Piperidine Compound treats or prevents a first Condition and the second therapeutic agent treats or prevents a second disorder, which can be the same as the first Condition or another disorder. In one embodiment, a Substituted-Quinoxaline-Type Bridged-Piperidine Compound is administered concurrently with a second therapeutic agent as a single composition comprising an effective amount of a Substituted-Quinoxaline-Type Bridged-Piperidine Compound and an effective amount of the second therapeutic agent. Alternatively, a composition comprising an effective amount of a Substituted-Quinoxaline-Type Bridged-Piperidine Compound and a second composition comprising an effective amount of the second therapeutic agent are concurrently administered. In another embodiment, an effective amount of a Substituted-Quinoxaline-Type Bridged-Piperidine Compound is administered prior or subsequent to administration of an effective amount of the second therapeutic agent. In this embodiment, the Substituted-Quinoxaline-Type Bridged-Piperidine Compound is administered while the second therapeutic agent exerts its therapeutic effect, or the second therapeutic agent is administered while the Substituted-Quinoxaline-Type Bridged-Piperidine Compound exerts its therapeutic effect for treating or preventing a Condition.

A composition of the invention is prepared by a method comprising admixing a Substituted-Quinoxaline-Type Bridged-Piperidine Compound or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Substituted-Quinoxaline-Type Bridged-Piperidine Compound is present in the composition in an effective amount.

4.8 Kits

The invention further provides kits that can simplify the handling and administration of a Substituted-Quinoxaline-Type Bridged-Piperidine Compound to an animal.

A typical kit of the invention comprises a unit dosage form of a Substituted-Quinoxaline-Type Bridged-Piperidine Compound. In one embodiment, the unit dosage form comprises a first container, which can be sterile, containing an effective amount of a Substituted-Quinoxaline-Type Bridged-Piperidine Compound and a pharmaceutically acceptable carrier or excipient. The kit can further comprise a label or printed instructions instructing the use of the Substituted-Quinoxaline-Type Bridged-Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Substituted-Quinoxaline-Type Bridged-Piperidine Compound, an effective amount of a second therapeutic agent and a pharmaceutically acceptable carrier or excipient. Examples of second therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The invention relates to methods for preparing Substituted-Quinoxaline-Type Bridged-Piperidine Compounds and/or pharmaceutically acceptable derivatives thereof, such as illustrated in the following examples. The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

The following examples illustrate various aspects of the invention, and are not to be construed to limit the claims in any manner whatsoever.

5.1 Example 1

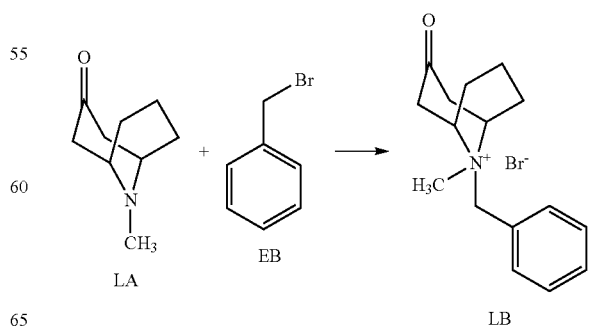

A mixture of the compound of formula LA (10.00 g, 65.4 mmol, Trans World Chemicals, Inc., Rockville, Md.) and the compound of formula EB, (bromomethyl)benzene (17 g, 65.4 mmol, Sigma-Aldrich, St. Louis, Mo.) was refluxed in acetone (150 mL) for 3 h, cooled, filtered, washed twice with Et$_2$O (30 mL for each wash), washed twice with hexanes (30 mL for each wash), and dried under reduced pressure to provide 10 g of the compound of formula LB, 9-methyl-9-benzyl-9-azabicyclo[3.3.1]nonan-3-one bromide, as white solid (yield 47%).

reduced pressure to provide 1020 mg of the compound of formula QB as a colorless solid (yield 45%).

The identity of the compound of formula QB, 9-((exo)-bicyclo[3.3.1]nonan-3-yl)-9-azabicyclo[3.3.1]nonan-3-one, was confirmed using $^1$H NMR and LC/MS.

To a mixture of the compound of formula QA ((exo)-bicyclo[3.3.1]nonan-3-amine, 1222 mg, 8.78 mmol), K$_2$CO$_3$ (121.3 mg, 0.878 mmol), EtOH (10 mL), and water (3 mL) at a temperature of about 25° C. was added a mixture of the compound of formula LB (2846 mg, 8.78 mmol), EtOH (14

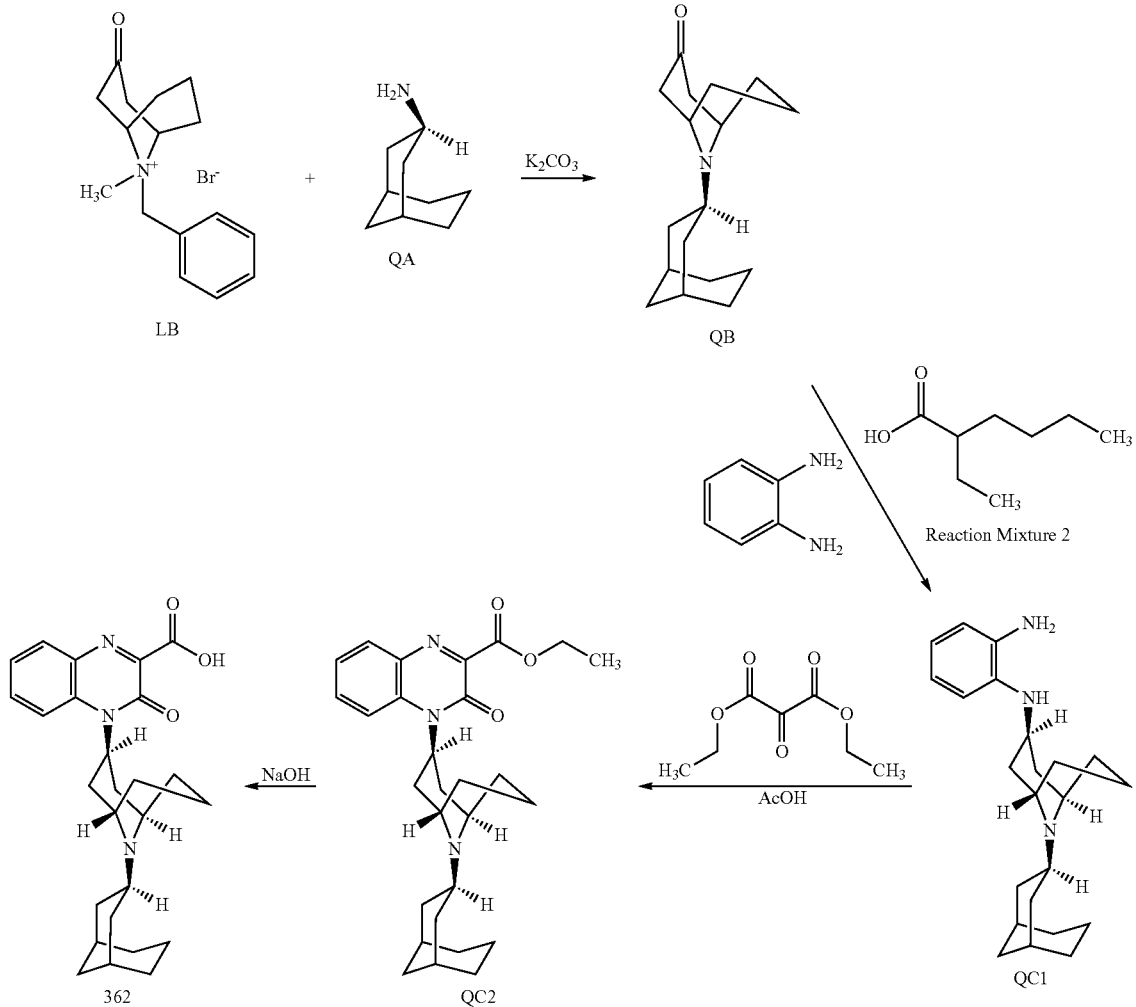

To a mixture of the compound of formula QA ((exo)-bicyclo[3.3.1]nonan-3-amine, 1222 mg, 8.78 mmol), K$_2$CO$_3$ (121.3 mg, 0.878 mmol), EtOH (10 mL), and water (3 mL) at a temperature of about 25° C. was added a mixture of the compound of formula LB (2846 mg, 8.78 mmol), EtOH (14 mL), and water (16 mL). After the addition, the resulting reaction mixture was heated to a temperature of 90° C. and stirred for 4 h. Thereafter, the reaction mixture was cooled to a temperature of about 25° C. and ice-water (50 mL) was poured into the reaction mixture to provide a colorless precipitate. To the precipitate was added saturated aqueous NaHCO$_3$ (10 mL). The mixture was sonicated; a precipitate formed. The precipitate was filtrated, washed twice with water (8 mL for each wash), and dried at 70° C. for 8 h under mL), and water (16 mL). After the addition, the resulting reaction mixture was heated to a temperature of 90° C. and stirred for 4 h. Thereafter, the reaction mixture was cooled to a temperature of about 25° C. and ice-water (50 mL) was poured into the reaction mixture to provide a colorless precipitate. To the precipitate was added saturated aqueous NaHCO$_3$ (10 mL). The mixture was sonicated; a precipitate formed. The precipitate was filtrated, washed twice with water (8 mL for each wash), and dried at 70° C. for 8 h under reduced pressure to provide 1020 mg of the compound of formula QB as a colorless solid (yield 45%).

The identity of the compound of formula QB, 9-((exo)-bicyclo[3.3.1]nonan-3-yl)-9-azabicyclo[3.3.1]nonan-3-one, was confirmed using $^1$H NMR and LC/MS.

Compound QB: $^1$H NMR: $\delta_H$ (400 MHz, CDCl$_3$): 1.26 (s, 1H), 1.43-1.69 (m, 13H), 1.85 (m, 2H), 2.01 (m, 4H), 2.22 (d, 2H), 2.63 (dd, J=16.42, 6.32 Hz, 2H), 3.35-3.41 (m, 1H), 3.69 (s, 2H); LC/MS: m/z=262.1 [M+H]$^+$ (Calc: 261).

Under a nitrogen atmosphere, to a solution of the compound of formula QB (1020 mg, 3.90 mmol) in CH$_2$Cl$_2$ (15 mL) at a temperature of about 25° C. was added 1,2-phenylenediamine (1266 mg, 11.71 mmol, Sigma-Aldrich) and 2-ethylhexanoic acid (0.938 mL, 5.85 mmol, Sigma-Aldrich). The mixture was stirred at a temperature of about 25° C. for 30 min to provide reaction mixture 1.

Under a nitrogen atmosphere, to a solution of sodium tetrahydroborate (590 mg, 15.61 mmol, Sigma-Aldrich) in CH$_2$Cl$_2$ (10 mL) at a temperature of about 25° C. was added 2-ethylhexanoic acid (8.75 mL, 54.6 mmol). The mixture was stirred at a temperature of about 25° C. for 30 min to provide reaction mixture 2.

Under a nitrogen atmosphere, to reaction mixture 1 at 0° C. was added reaction mixture 2 dropwise over a 15 min period. After the addition, the resulting reaction mixture was heated to a temperature of about 25° C. and stirred for 30 min. Thereafter, the reaction mixture was heated to a temperature of 60° C. and stirred for 16 h. After cooling the reaction mixture to a temperature of about 25° C., saturated aqueous NaHCO$_3$ (20 mL) was added, the mixture stirred for 10 min, then extracted twice with 1M aqueous K$_2$CO$_3$/EtOAc (200 mL for each extraction). The organic portions were combined, dried (Na$_2$SO$_4$), and concentrated under reduced pressure to provide a brown solid. The solid was chromatographed with an amino-silica gel column (Yamazen Corp. WO91-01) eluted with a gradient of from 0%:100% EtOAc:n-hexane to 30%:70% EtOAc:n-hexane to provide 815 mg of the compound of formula QC1 as a colorless solid (yield 59%).

The identity of the compound of formula QC1, N$^1$-((endo)-9-((exo)-bicyclo[3.3.1]nonan-3-yl)-9-azabicyclo[3.3.1]nonan-3-yl)benzene-1,2-diamine, was confirmed using $^1$H NMR and LC/MS.

Compound QC-1: $^1$H NMR: $\delta_H$ (400 MHz, CDCl$_3$): 1.02-1.83 (m, 17H), 2.01 (m, 5H), 2.40-2.48 (m, 2H), 3.06-3.45 (m, 6H), 3.76 (br, 1H), 6.61-6.82 (m, 4H); LC/MS: m/z=354.1 [M+H]$^+$ (Calc: 353).

Under a nitrogen atmosphere, to a solution of the compound of formula QC1 (815 mg, 2.305 mmol) in toluene (16 mL) at a temperature of about 25° C. was added diethyl 2-oxomalonate (0.407 mL, 2.54 mmol, Sigma-Aldrich) and AcOH (0.145 mL, 2.54 mmol). After the addition, the resulting reaction mixture was heated to a temperature of 130° C. and stirred for 1 h. Thereafter, the reaction mixture was cooled to a temperature of about 25° C. and concentrated under reduced pressure to provide a sticky oil. The oil was diluted with saturated aqueous NaHCO$_3$, extracted twice with CHCl$_3$:H$_2$O (100 mL for each extraction), dried (Na$_2$SO$_4$), and concentrated under reduced pressure to provide an orange solid. The solid was chromatographed with an amino-silica gel column (Yamazen Corp. WO91-01) eluted with a gradient of from 0%:100% EtOAc:n-hexane to 20%:80% EtOAc:n-hexane to provide 560 mg of the compound of formula QC2 as a colorless solid (yield 52%).

The identity of the compound of formula QC2, ethyl 4-((endo)-9-((exo)-bicyclo[3.3.1]nonan-3-yl)-9-azabicyclo[3.3.1]nonan-3-yl)-3-oxo-3,4-dihydroquinoxaline-2-carboxylate, was confirmed using $^1$H NMR and LC/MS.

Compound QC2: $^1$H NMR: $\delta_H$ (400 MHz, CDCl$_3$): 1.04-1.11 (m, 2H), 1.35-1.86 (m, 17H), 1.92-2.02 (m, 6H), 2.37-2.47 (m, 1H), 2.67-2.79 (m, 1H), 3.46-3.56 (m, 3H), 4.51 (q, J=7.07 Hz, 2H), 5.20 (m, 1H), 7.34-7.37 (m, 1H), 7.63 (t, J=6.57 Hz, 2H), 7.92 (d, J=8.08 Hz, 1H); LC/MS: m/z=464.2 [M+H]$^+$ (Calc: 463).

To a suspension of the compound of formula QC2 (561 mg, 1.21 mmol) in EtOH (15 mL) at a temperature of about 25° C. was added 2N aqueous NaOH (1.812 mL, 3.62 mmol). The resulting reaction mixture was stirred at a temperature of about 25° C. for 1 h. Thereafter, the reaction mixture was concentrated under reduced pressure to provide a residue. The residue was diluted with water (10 mL) to form a colorless solution, neutralized with 2N aqueous HCl (2.3 mL), and sonicated to provide a white precipitate. The precipitate was collected by filtration, washed with water, and dried at 75° C. for 5 h under reduced pressure to provide 396 mg of Substituted-Quinoxaline-Type Bridged-Piperidine Compound 362 as a colorless solid (yield 75%).

The identity of Substituted-Quinoxaline-Type Bridged-Piperidine Compound 362, 4-((endo)-9-((exo)-bicyclo[3.3.1]nonan-3-yl)-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Bridged-Piperidine Compound 362: $^1$H NMR: $\delta_H$ (400 MHz, CDCl$_3$): 0.83 (dq, J=8.72, 2.78 Hz, 1H), 1.22 (s, 1H), 1.38 (br, 1H), 1.54 (d, J=12.63 Hz, 1H), 1.69 (s, 6H), 1.87 (m, 4H), 2.05 (t, J=13.89 Hz, 2H), 2.22 (s, 2H), 2.51 (dd, J=19.71, 11.12 Hz, 2H), 2.70 (m, 3H), 2.98 (t, J=12.38 Hz, 2H), 4.11-4.22 (m, 3H), 6.65 (br, 1H), 7.51-7.62 (m, 4H), 7.93 (t, J=7.83 Hz, 1H), 8.16 (d, J=8.08 Hz, 1H), 8.96 (dd, J=7.83, 6.32 Hz, 1H), 10.89 (s, 1H); LC/MS (100%, t$_r$=1.55 min): m/z=436.2 [M+H]$^+$ (Calc: 436).

Taking into account the procedures provided in J. A. Peters, J. M. Van Der Toorn and H. Van Bekkumm, *Tetrahedron* 31:2273-2281 (1975) and "Diphenylphosphoryl azide a new convenient reagent for a modified Curtius rearrangement and for peptide synthesis," T. Shioiri, K. Ninomiya, S. Yamada, *J. Amer. Chem. Soc.* 94:6202-6205 (1972), the compound of formula QA was prepared as follows.

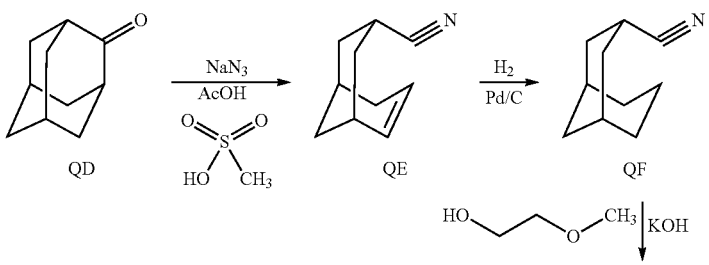

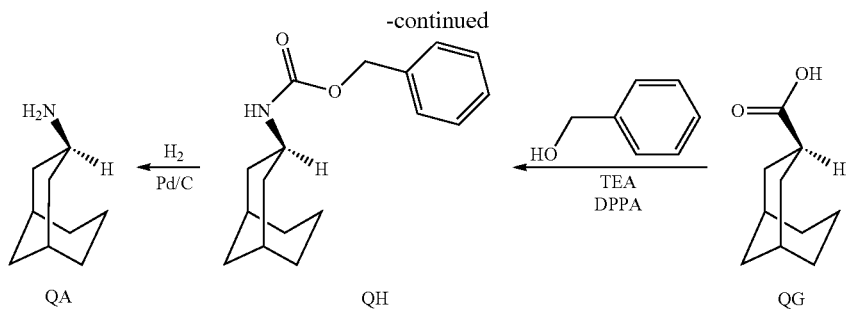

Under a nitrogen atmosphere, to a solution of the compound of formula QD (adamantane-2-one, 60 g, 399 mmol, Sigma-Aldrich) in AcOH (251 mL, 4394 mmol) and methane sulfonic acid (182.00 mL, 2803 mmol, Sigma-Aldrich) at a temperature of 20° C. was added sodium azide (29.9 g, 459 mmol) portionwise over 45 min. After the addition, the resulting reaction mixture was stirred for 30 min at a temperature of from 20° C. to 25° C. Thereafter, ice-water (1 L) was poured into the reaction mixture to provide a white precipitate that was collected by filtration, washed with water (400 mL), and dried at 60° C. for 4 h under reduced pressure to provide 40.78 g of the compound of formula QE as a colorless solid (yield 69%).

The identity of the compound of formula QE, bicyclo[3.3.1]non-6-ene-3-carbonitrile, was confirmed using $^1$H NMR.

Compound QE: $^1$H NMR: $\delta_H$ (400 MHz, CDCl$_3$): 1.53 (d, J=12.67 Hz, 1H), 1.72-2.05 (m, 5H), 2.23 (dt, J=17.91 Hz, 8.11 Hz, 2H), 2.41-2.50 (m, 2H), 2.96 (dd, J=9.63, 4.06 Hz, 1H), 5.85-5.95 (m, 2H).

Under a hydrogen atmosphere, a mixture of the compound of formula QE (5260 mg, 35.7 mmol), 10% palladium on carbon (570 mg, 0.536 mmol, Sigma-Aldrich), and MeOH (150 mL) was stirred at a temperature of about 25° C. for 4 h. After the Pd/C was filtered off, the mixture was concentrated under reduced pressure to provide a colorless oil. The oil was chromatographed with a silica gel column eluted with a gradient of from 3%:97% EtOAc:n-hexane to 20%:80% EtOAc:n-hexane to provide 3500 mg of the compound of formula QF as a colorless solid (yield 66%).

The identity of the compound of formula QF, bicyclo[3.3.1]nonane-3-carbonitrile, was confirmed using $^1$H NMR.

Compound QF: $^1$H NMR: $\delta_H$ (400 MHz, CDCl$_3$): 1.22 (m, 1H), 1.38-1.59 (m, 8H), 1.72-1.82 (m, 1H), 2.04-2.08 (m, 2H), 2.20-2.28 (m, 2H), 2.60-2.69 (m, 1H).

Under a nitrogen atmosphere, to a solution of the compound of formula QF (2530 mg, 16.95 mmol) in 2-methoxyethanol (26.9 mL, 339 mmol) at a temperature of about 25° C. was added KOH (4280 mg, 76 mmol). After the addition, the resulting reaction mixture was heated to a temperature of 120° C. and stirred for 16 h. Thereafter, the reaction mixture was cooled to a temperature of about 25° C., 2N aqueous HCl was added such that the pH was within 3 to 4, and a pale brown precipitate formed. The precipitate was collected by filtration, washed with water, and dried at 70° C. for 3 h under reduced pressure to provide a pale brown solid, which $^1$H NMR showed to be a 1:9 mixture of endo:exo isomers.

Under a nitrogen atmosphere, to a solution of the above endo:exo isomer mixture in 2-methoxyethanol (73.5 mL, 932 mmol) at a temperature of about 25° C. was added KOH (4756 mg, 85 mmol). After the addition, the resulting reaction mixture was heated to a temperature of 120° C. and stirred for 16 h. Thereafter, the reaction mixture was cooled to a temperature of about 25° C., 2N aqueous HCl was added such that the pH was within 3 to 4, and a pale brown precipitate formed. The precipitate was collected by filtration, washed with water, and dried at 70° C. for 3 h under reduced pressure to provide 2187 mg of the compound of formula QG as a pale brown solid, with a melting point of 126-128° C. and present only as the exo isomer (yield 77%).

The identity of the compound of formula QG, (exo)-bicyclo[3.3.1]nonane-3-carboxylic acid, was confirmed using $^1$H NMR.

Compound QG: $^1$H NMR: $\delta_H$ (400 MHz, CDCl$_3$): 1.52-1.85 (m, 10H), 1.96 (t, J=6.59 Hz, 4H), 3.10-3.19 (m, 1H).

Under a nitrogen atmosphere, to a solution of the compound of formula QG (2680 mg, 15.93 mmol) in toluene (25 mL) at a temperature of about 25° C. was added TEA (2.65 mL, 19.12 mmol, Sigma-Aldrich) and DPPA (4.51 mL, 19.12 mmol, Sigma-Aldrich). After the addition, the resulting reaction mixture was heated to a temperature of 70° C. and stirred for 1 h. Thereafter, the reaction mixture was cooled to a temperature of about 25° C. and concentrated under reduced pressure to provide a pale yellow oil, which was dried under reduced pressure at a temperature of about 25° C. To the oil was added phenylmethanol (4.77 mL, 45.9 mmol, Sigma-Aldrich). After the addition, the resulting reaction mixture was heated to a temperature of 90° C. and stirred for 1.5 h. Thereafter, the reaction mixture was cooled to a temperature of about 25° C. and chromatographed with a silica gel column eluted with a gradient of from 2%:98% EtOAc:n-hexane to 10%:90% EtOAc:n-hexane to provide 4270 mg of the compound of formula QH as a colorless solid (yield 98%).

The identity of the compound of formula QH, benzyl (exo)-bicyclo[3.3.1]nonan-3-ylcarbamate, was confirmed using $^1$H NMR and LC/MS.

Compound QH: $^1$H NMR: $\delta_H$ (400 MHz, CDCl$_3$): 1.32 (td, J=12.25, 3.71 Hz, 2H), 1.44-1.80 (m, 8H), 1.97-2.09 (m, 4H), 4.28-4.46 (m, 2H), 5.08 (s, 2H), 7.26-7.35 (m, 5H); LC/MS: m/z=274.2 [M+H]$^+$ (Calc: 273).

Under a hydrogen atmosphere, a mixture of the compound of formula QH (4456 mg, 16.30 mmol), 10% palladium on carbon (694 mg, 0.652 mmol), and EtOH (50 mL) was stirred at a temperature of about 25° C. for 3 h. After filtering off the Pd/C and washing with EtOH, the mixture was concentrated under reduced pressure to a volume of 20 mL. The EtOH solution contained 2270 mg (16.30 mmol) of the compound of formula QA.

Alternatively, the compound of formula QG was prepared from the compound of formula QD as follows.

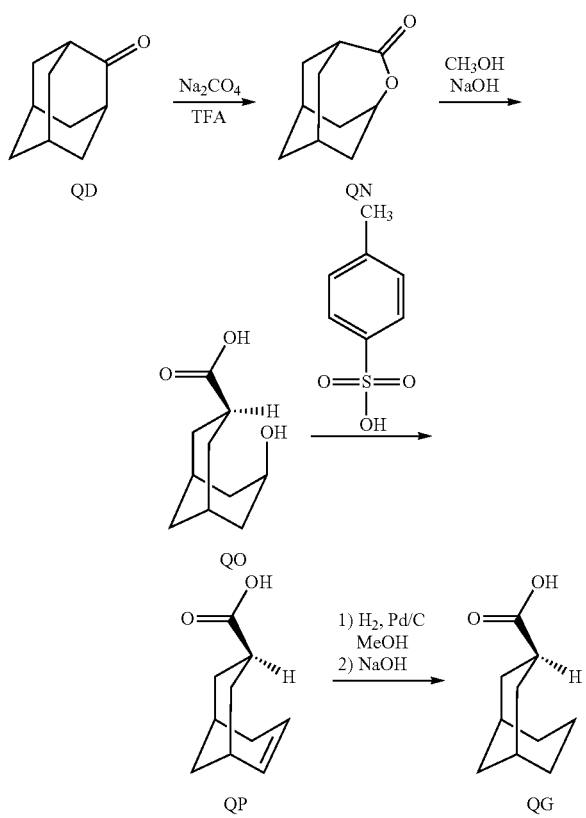

The compound of formula QD (200 g, 1.33 mol) was dissolved in 2,2,2-trifluoroacetic acid (1 L, Sigma-Aldrich) and cooled to 0° C. by an ice/MeOH bath. To this mechanically-stirred mixture was added sodium percarbonate (417.64 g, 2.66 mol) portionwise such that the temperature of the reaction mixture was kept below 5° C. The cold bath was removed and the reaction mixture was allowed to warm to a temperature of about 25° C. After 2.5 h stirring at about 25° C., deionized water (1 L) was added over 5 min followed by the addition of DCM (2 L). The DCM layer was separated, dried (MgSO$_4$), filtered, and concentrated to dryness under reduced pressure to provide 209 g of the compound of formula QN as a white crystalline solid (yield 95%).

The identity of the compound of formula QN, 4-oxa-tricyclo[4.3.1.1*3,8*]undecan-5-one, was confirmed using $^1$H NMR and TLC.

Compound QN: $^1$H NMR: $\delta_H$ (400 MHz, CDCl$_3$): 4.48 (1H, s), 3.06 (1H, m), 2.09 (2H, m), 2.00 (3H, m), 1.95 (2H, m), 1.81 (2H, m), 1.70 (2H, m); TLC (SiO$_2$, 1:1 EtOAc:hexanes) (visualized with molybdenum blue spray reagent).

To a mixture of the compound of formula QN (165.52 g, 1.0 mol) and MeOH (200 mL) was added 10M NaOH (600 mL). Thereafter, with stirring the resulting reaction mixture was heated at reflux for 24 h. After cooling to a temperature of about 25° C., the mixture was concentrated under reduced pressure and deionized water (4 L) was added. The resulting solution was stirred and acidified with concentrated HCl to a pH of about 2.5. The white precipitate that formed was allowed to stir with ice bath cooling for 1 h and then filtered under reduced pressure to provide the partially dried compound of formula QO.

The identity of the compound of formula QO, exo-7-hydroxybicyclo[3.3.1]nonane-3-carboxylic acid, was confirmed using $^1$H NMR and TLC.

Compound QO: $^1$H NMR: $\delta_H$ (400 MHz, DMSO-d$_6$): 11.88 (1H, s), 4.44 (1H, s), 3.73 (1H, m), 1.95 (4H, m), 1.63 (2H, m), 1.41 (3H, m), 1.22 (2H, m), 1.16 (1H, m); TLC (SiO$_2$, 2:1:0.1 EtOAc:hexanes:AcOH)R$_f$=0.3 (visualized with molybdenum blue spray reagent). The $^1$H-NMR indicated that the compound of formula QO was about 97% to 98% pure and nuclear Overhauser enhancement spectroscopy ("NOESY") NMR indicated only the exo-isomer was present.

The compound of formula QO from the step above was suspended in toluene (1.2 L) and to this was added TsOH (35.6 mL, 0.5 mol, Sigma-Aldrich). With stirring the resulting reaction mixture was heated to reflux with azeotropic removal of water for 2 h. After cooling to a temperature of about 25° C., deionized water (1 L) was added. The toluene layer was separated, dried (MgSO$_4$), filtered, and concentrated under reduced pressure to provide the compound of formula QP, which could be if desired but which was not recrystallized from cyclohexane.

The identity of the compound of formula QP, exo-bicyclo[3.3.1]non-6-ene-3-carboxylic acid, was confirmed using $^1$H NMR and TLC.

Compound QP: $^1$H NMR: $\delta_H$ (400 MHz, CDCl$_3$): 10.45 (1H, bs), 5.85 (1H, m), 5.70 (1H, m), 2.79 (1H, m), 2.37 (2H, m), 2.11 (1H, m), 1.81 (3H, m), 1.61 (4H, m); TLC (SiO$_2$, 1:1:0.1 EtOAc:hexanes:AcOH)R$_f$=0.8 (visualized with molybdenum blue spray reagent). The $^1$H-NMR indicated that the compound of formula QP was about 97% to 98% pure and NOESY indicated only the exo-isomer was present.

The compound of formula QP from the step above was added to 6:1 EtOAc:MeOH (700 mL). This mixture was split into two batches and to each batch was added 10% palladium on carbon (0.01 mol). Under a 50 psi hydrogen atmosphere, each batch was stirred at a temperature of about 25° C. for 2 h. The batches were combined, filtered through CELITE, and concentrated to dryness under reduced pressure at 50° C. to provide a cream colored sticky solid which was determined to be a mixture of the desired product and its methyl ester. To the solid was added MeOH (600 mL) and 3M NaOH (300 mL). The resulting reaction mixture was stirred at a temperature of about 25° C. for 1 h. The mixture was poured into deionized water (3 L) and concentrated HCl was added until the pH was about 2. Then DCM (3 L) was added. The resulting layers were separated and the aqueous layer was washed with DCM (2 L). The organic portions were combined, dried (MgSO$_4$), filtered, and concentrated to dryness under reduced pressure to provide 147.34 g of the compound of formula QG as a white crystalline solid (yield 88% for three steps).

The identity of the compound of formula QG was confirmed using $^1$H NMR and TLC.

Compound QG: $^1$H NMR: $\delta_H$ (400 MHz, CDCl$_3$): 9.25 (1H, bs), 3.13 (1H, m), 1.97 (4H, m), 1.80 (2H, m), 1.70 (5H, m), 1.57 (3H, m); TLC (SiO$_2$, 1:1:0.1 EtOAc:hexanes:AcOH)R$_f$=0.8 (visualized with molybdenum blue spray reagent).

Alternatively, the compound of formula QA was prepared from the compound of formula QG as follows.

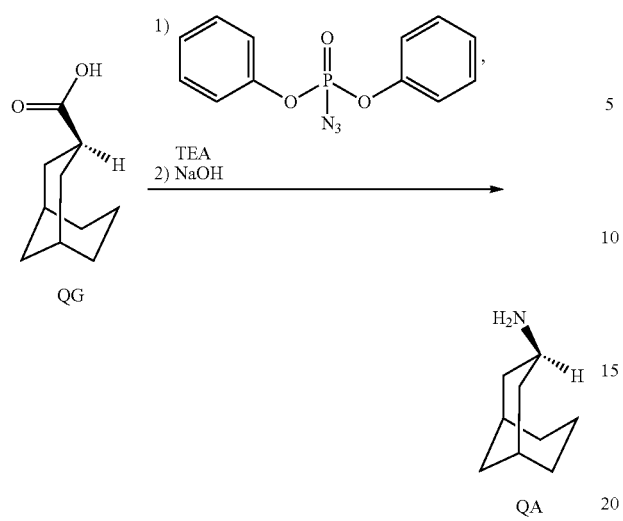

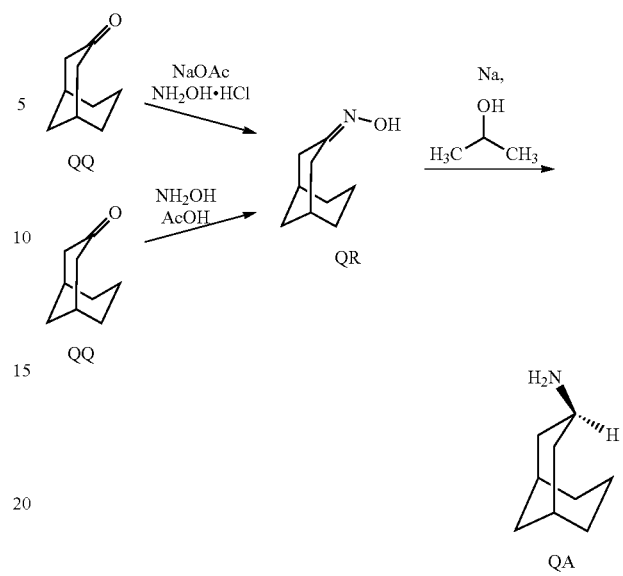

Under an argon atmosphere, to a solution of the compound of formula QG (5.23 g, 31.13 mmol) in toluene (50 mL) at a temperature of about 25° C. was added TEA (4.77 mL, 34.24 mmol) and DPPA (7.40 mL, 34.24 mmol). After the addition, the resulting reaction mixture was heated to a temperature of 75° C. and stirred for 1 h. Thereafter, the reaction mixture was cooled to a temperature of 70° C. and concentrated to dryness under reduced pressure to provide a yellow oil. The oil was cooled to 5° C. and THF (50 mL) was added. While stirring, the mixture was further cooled to 0° C. and a solution of NaOH (3.73 g, 93.39 mmol) in deionized water (25 mL) was added dropwise over 15 min while maintaining the temperature of the reaction mixture below 5° C. The reaction mixture was stirred for 1 h at 0° C. then treated with concentrated HCl until the pH was about 8. Deionized water (100 mL) was added; a white precipitate formed. The mixture was stirred an additional 30 min at 0° C. The precipitate was collected by filtration under reduced pressure then suspended in 1:1 M NaOH:Et$_2$O (500 mL). The mixture was stirred until all solids disappeared. Upon ending stirring, the layers that formed were separated and the aqueous layer was washed with Et$_2$O (250 mL). The organic portions were combined, dried (MgSO$_4$), and filtered. To the filtrate was added 2M HCl in Et$_2$O (38 mL, 77.83 mmol); a white solid formed. The mixture was cooled to −5° C. and stirred an additional 1 h. The solid was collected by filtration and dried under reduced pressure at 50° C. to provide 4.1 g of the compound of formula QA as the diphenylphosphate salt (yield 75%).

The identity of the compound of formula QA was confirmed using $^1$H NMR and TLC.

Compound QA: $^1$H NMR: $\delta_H$ (400 MHz, CD$_3$OD): 3.91 (1H, m), 2.08 (4H, m), 1.71 (4H, m), 1.59 (6H, m); TLC (SiO$_2$, 1:1:0.1 DCM:MeOH:NH$_3$) R$_f$=0.4 (visualized with molybdenum blue spray reagent).

Alternatively, taking into account the procedures provided in F. I. Carroll, M. S. Melvin, M. C. Nuckols, S. W. Mascarella, H. A. Navarro, and J. B. Thomas, *J. Med. Chem.* 49:1781-1791 (2006), the compound of formula QA was prepared from the compound of formula QQ as follows.

Under a nitrogen atmosphere, to a solution of the compound of formula QQ (bicyclo[3.3.1]nonan-3-one, 975 mg, 7.05 mmol) in EtOH (40 mL) at a temperature of about 25° C. was added sodium acetate (1,157 mg, 14.11 mmol, Sigma-Aldrich) and hydroxylamine hydrochloride (980 mg, 14.11 mmol, Sigma-Aldrich). The resulting reaction mixture was stirred at a temperature of about 25° C. for 2 h. Thereafter, the mixture was diluted with saturated aqueous NaHCO$_3$ then extracted three times with EtOAc (30 mL for each extraction). The organic portions were combined, washed with saturated aqueous NaCl, dried (MgSO$_4$), and evaporated under reduced pressure to provide 800 mg of the compound of formula QR as a yellow solid (yield 76%).

The identity of the compound of formula QR, bicyclo [3.3.1]nonan-3-one oxime, was confirmed using $^1$H NMR.

Compound QR: $^1$H NMR: $\delta_H$ (CDCl$_3$): 1.40 (m, 1H), 1.50-1.80 (m, 8H), 1.99-2.17 (m, 3H), 2.40 (d, J=8.0 Hz, 2H), 3.20 (d, J=16 Hz, 1H).

Alternatively, the compound of formula QR was prepared from the compound of formula QQ as follows. To a solution of the compound of formula QQ (390 g, 2.822 mol) in dry THF (2 L) at a temperature of about 25° C. was added 50% aqueous hydroxylamine (207.5 mL, 3.386 mol, Sigma-Aldrich) followed by acetic acid (204 mL, 3.386 mol); thereafter, the temperature of the resulting reaction mixture rose to 35° C. While stirring, the reaction mixture was heated at 40° C. for 2 h. The mixture was poured into water (2 L) and neutralized with sodium bicarbonate. The organic portion was separated and the aqueous portion was extracted with EtOAc (2 L). The organic portions were combined, dried (MgSO$_4$), and concentrated to dryness under reduced pressure to provide a residue. The residue was dried at 50° C. for 16 h under reduced pressure in a vacuum oven to provide 417 g of the compound of formula QR as a white solid (yield 96.5%).

Under a nitrogen atmosphere, to a refluxing suspension of sodium (2.401 g, 104 mmol, Sigma-Aldrich) in toluene (20 mL) at 115° C. was added a mixture of the compound of formula QR (1.60 g, 10.44 mmol) and 2-propanol (8 mL) dropwise over 30 min. The reaction mixture was stirred at reflux for 2 h. Additional 2-propanol (3 mL) was added dropwise. The reaction mixture was refluxed until the sodium was consumed. Thereafter, the mixture was cooled to a temperature of about 25° C. then quenched by the addition of water (20 mL). The organic portion was separated and washed twice with 1N HCl (30 mL for each wash). The acidic solution was made alkaline by the addition of 2N NaOH (50 mL) and extracted three times with Et$_2$O (50 m for each extraction). The organic portions were combined, washed with saturated aqueous NaCl (50 mL), dried (Na$_2$SO$_4$), filtered, and concentrated under reduced pressure to provide the compound of formula QA.

The identity of the compound of formula QA was confirmed using $^1$H NMR.

Compound QA: $^1$H NMR: $\delta_H$ (CDCl$_3$): 3.38 (m, 1H), 1.90 (m, 4H), 1.70-1.20 (m, 10H).

Taking into account the procedures provided in "Improved synthetic methods for bicyclo[3.3.1]nonan-3-one," T. Momose et al., Chem. Pharmaceut. Bull. 26(1):288-295 (1978), the compound of formula QQ was prepared as follows.

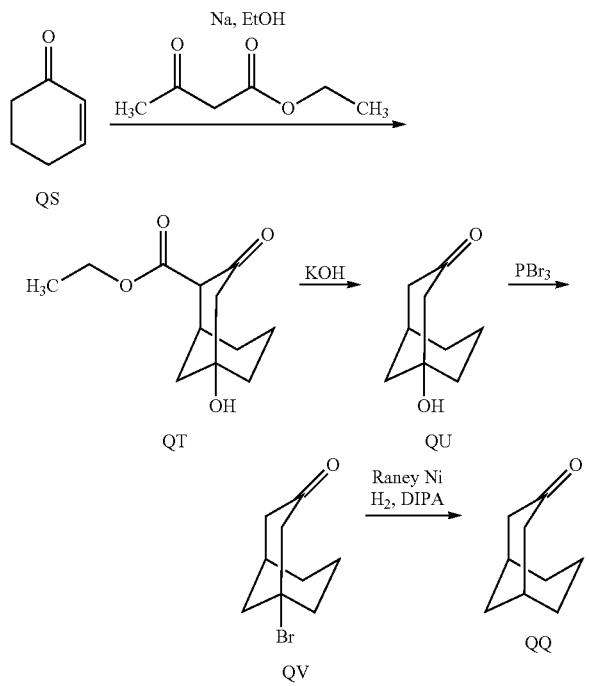

Under a nitrogen atmosphere and with mechanical stirring, to EtOH (2 L) was added small pieces of sodium (63.2 g, 2.746 mol). The resulting suspension was heated to reflux and stirred under gentle reflux conditions until the sodium dissolved (about 1 h). Thereafter, ethyl 3-oxobutanoate (357.4 g, 2.746 mol, Sigma-Aldrich) was added and the mixture was stirred for 5 min. Thereafter, the compound of formula QS (cyclohex-2-enone, 220 g, 2.288 mol, Sigma-Aldrich) was added dropwise over 30 min. The resulting orange reaction mixture was stirred under reflux for 48 h. This first batch of the mixture was concentrated under reduced pressure to about half its original volume and poured into crushed ice (about 2 kg). The procedure above was repeated to provide a second batch. The two batches were combined, the mixture was acidified to a pH of 5 with concentrated HCl, and extracted twice with EtOAc (2 L for each extraction). The organic portions were combined, dried (MgSO$_4$), and concentrated to dryness under reduced pressure to provide an orange oil. The oil was adsorbed onto silica gel (1 kg) and applied to a flash chromatograph with a silica gel column (2 kg) eluted with a gradient of from 0%:100% EtOAc:hexanes to 50%:50% EtOAc:hexanes to provide a yellow oil. The oil was dissolved in hexanes (1 L). With mechanical stirring, the solution was cooled to −10° C. by an ice/MeOH bath, seeded with a crystal of the desired product, stirred for about 1 h, then filtered and dried under reduced pressure to provide 753 g of the compound of formula QT, ethyl 5-hydroxy-3-oxobicyclo[3.3.1]nonane-2-carboxylate, as a white solid (yield 73%).

The compound of formula QT (500 g, 2.210 mol) was dissolved in EtOH (2.5 L). KOH (371.8 g, 6.63 mol) in water (2.5 L) was added and the resulting reaction mixture was refluxed with stirring for 5.5 h. The mixture was concentrated under reduced pressure to about half its original volume, poured into water (3 L), and extracted twice with DCM (3 L for each extraction). The organic portions were combined, dried (MgSO$_4$), and concentrated to dryness under reduced pressure to provide a yellow solid. The solid was dissolved in toluene (2 L). The solution was mechanically-stirred for 1 h then filtrated to provide 300 g of the compound of formula QU, 1-hydroxybicyclo[3.3.1]nonan-3-one, as a pale yellow solid (yield 88%).

With mechanical stirring, the compound of formula QU (500 g, 3.2425 mol) was dissolved in dry DCM (2 L) and cooled to −30° C. Phosphorus tribromide (965.5 g, 3.5667 mol, Sigma-Aldrich) in DCM (1 L) was added portionwise over 30 min. The resulting orange red solution allowed to warm slowly to 10° C. over 3 h. With mechanical stirring, the mixture was poured into crushed ice (3 kg), diluted with hexanes (3 L), and the organic portion was separated. The organic portion was washed with water (4 L), washed with aqueous sodium bicarbonate solution (4 L), dried (MgSO$_4$), and evaporated to dryness under reduced pressure to provide 570.5 g of the compound of formula QV, 1-bromobicyclo[3.3.1]nonan-3-one, as pale yellow crystals which were dried under reduced pressure and then stored at below 0° C. under argon (yield 81%). As it is relatively unstable, it is important that the organic portion be properly basified and also well dried or the compound of formula QV may decompose on standing. If an emulsion forms when using DCM, the reaction can be carried out in dry toluene instead to facilitate the work-up.

Raney nickel (about 10 g, Sigma-Aldrich) was washed twice with dry THF (50 mL for each wash) then suspended in dry THF (50 mL). To this was added a mixture of the compound of formula QV (100 g, 0.4604 mol) and dry THF. Thereafter, diisopropylamine (DIPA, 71 mL, Sigma-Aldrich) was added and under a hydrogen atmosphere and the resulting reaction mixture was shaken in a Parr Hydrogenator at 60 psi for about 3 h until no further hydrogen was taken up. It is important to ensure the reaction has gone substantially to completion before proceeding. This can be done using TLC (SiO$_2$, 1:1 hexanes:DCM) in which the compound of formula QQ has a slightly lower R$_f$ than the compound of formula QV. Under a nitrogen atmosphere, the mixture was carefully filtered through CELITE, the filter pad washed with EtOAc (250 mL), and the filtrate evaporated to dryness under reduced pressure to provide a light yellow gum. The gum was flash chromatographed with a silica gel column eluted with 5:1 hexanes:EtOAc to provide a white solid. The solid was crystallized at −30° C. from hexanes (100 mL) to provide 60 g of the compound of formula QQ as a white solid (yield 95%).

Alternatively, taking into account the procedures provided in H. K. Hall, J. Org. Chem. 28:3213-3214 (1963), the compound of formula QQ was prepared as follows.

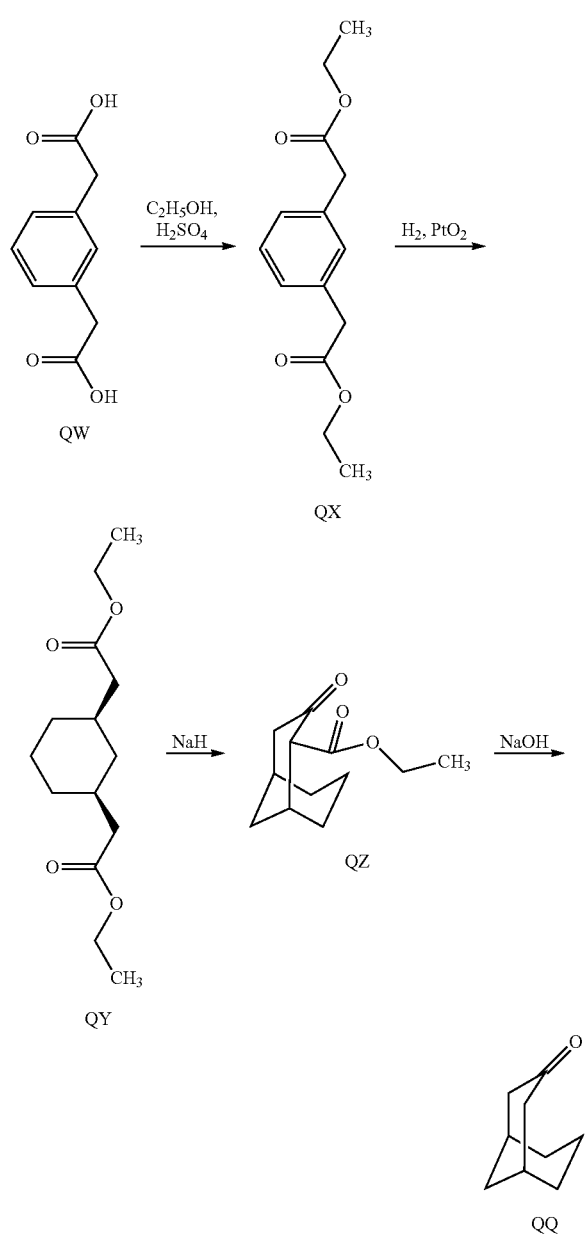

mol, Sigma-Aldrich), and acetic acid (250 mL) at 30° C. was degassed and stirred for 15 h. The mixture was flushed with argon and diluted with water (40 mL). The catalyst was removed by filtration. The mixture was concentrated under reduced pressure to about (200 mL) then diluted with toluene (400 mL). The mixture was washed twice with water (100 mL for each wash), washed twice with NaHCO$_3$ (100 mL for each wash), and washed with brine (100 mL). The mixture was concentrated under reduced pressure to provide the compound of formula QY as a colorless oil.

The identity of the compound of formula QY, diethyl 2,2'-((cis)-cyclohexane-1,3-diyl)diacetate, was confirmed using $^1$H NMR.

Compound QY: $^1$H NMR: $\delta_H$ (400 MHz, CDCl$_3$): 4.15 (q, J=7.2 Hz, 4H), 2.17 (d, J=7.0 Hz, 4H), 1.4-1.9 (m, 6H), 1.25 (t, J=7.1 Hz, 6H), 0.83-0.92 (m, 2H), 0.71 (dd, J=11.8, 11.9 Hz, 2H).

The compound of formula QY from the step above was dissolved in dry DME (300 mL). Sodium hydride (15 g, Sigma-Aldrich) was added and the resulting suspension was heated at 94° C. and stirred for 16 h. After cooling to a temperature of about 25° C., the mixture was slowly poured into ice-water (500 mL). The mixture was then extracted four times with EtOAc (200 mL for each extraction). The organic portions were combined, washed with brine, and concentrated under reduced pressure to provide the compound of formula QZ, ethyl 3-oxobicyclo[3.3.1]nonane-2-carboxylate.

The compound of formula QZ from the step above was dissolved in EtOH (150 mL). NaOH (30 g, 0.75 mol) in water (150 mL) was added and the resulting reaction mixture was heated at 70° C. for 8 h. Thereafter, the mixture was concentrated under reduced pressure, diluted with brine (150 mL), and extracted three times with Et$_2$O (150 mL for each extraction). The organic portions were combined and concentrated to dryness under reduced pressure to provide 18 g of the compound of formula QQ as a white solid (yield 51% for three steps).

The identity of the compound of formula QQ was confirmed using $^1$H NMR.

Compound QQ: $^1$H NMR: $\delta_H$ (CDCl$_3$): 2.52-1.31 (m, 6H), 1.82 (m, 2H), 1.70-1.56 (m, 5H), 1.54-1.32 (m, 2H).

5.2 Example 2

Substituted-Quinoxaline-Type Bridged-Piperidine Compound 362 was also prepared as follows.

To a solution of the compound of formula QW (2,2'-(1,3-phenylene)diacetic acid, 50 g, 0.26 mol, TCI-US, Portland, Oreg.) in EtOH (500 mL) at a temperature of about 25° C. was added concentrated sulfuric acid (2 mL). The resulting reaction mixture was refluxed for 24 h. After cooling to a temperature of about 25° C., the mixture was concentrated to about 200 mL under reduced pressure and diluted with toluene (400 mL). The mixture was washed with water (100 mL), washed with brine (100 mL), and concentrated to dryness under reduced pressure to provide 63 g of the compound of formula QX as a colorless oil (yield 98%).

The identity of the compound of formula QX, diethyl 2,2'-(1,3-phenylene)diacetate, was confirmed using $^1$H NMR.

Compound QX: $^1$H NMR: $\delta_H$ (400 MHz, CDCl$_3$): 7.26-7.3 (m, 1H), 7.18-7.21 (m, 3H), 4.15 (q, J=7.1 Hz, 4H), 3.6 (s, 4H), 1.25 (t, J=7.2 Hz, 6H).

Under a hydrogen atmosphere, a mixture of the compound of formula QX (63 g, 0.25 mol), platinum dioxide (2 g, 0.09

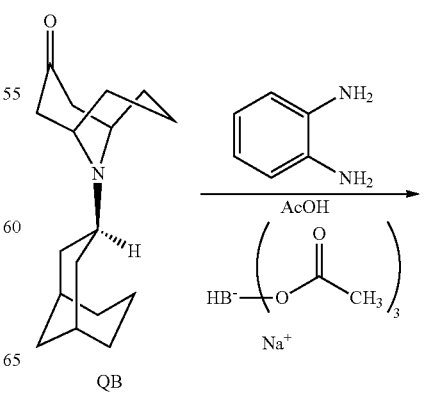

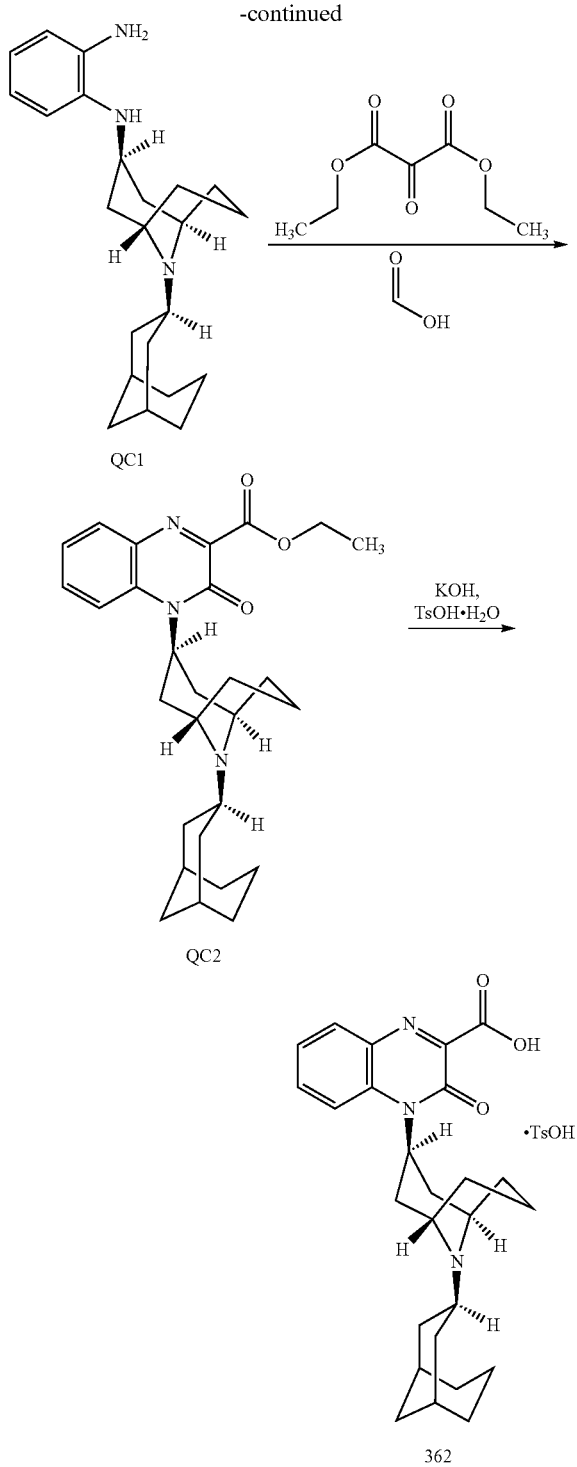

Under a nitrogen atmosphere, to a solution of the compound of formula QB (15 g, 57.38 mmol) and 1,2-phenylenediamine (18.62 g, 172.14 mmol) in DME (38 mL) at a temperature of about 25° C. was added was added acetic acid (15 mL). The mixture was stirred at a temperature of about 25° C. for 16 h to provide reaction mixture 3. To a suspension of sodium triacetoxy borohydride (42.56 g, 200.53 mmol) in DME (75 mL) at a temperature of about 25° C. was added dropwise reaction mixture 3 over 1 h. The reaction mixture was diluted with additional DME (23 mL) then stirred at a temperature of about 25° C. for 5 h. Thereafter, the reaction mixture was cooled to 0° C. then water (75 mL) was added dropwise over 30 min while the temperature of the reaction mixture rose from 0° C. to a temperature of about 25° C. The mixture was then extracted with $CHCl_3:H_2O$ (225 mL:75 mL) and the $CHCl_3$ extract was washed with 10% aqueous AcOH (75 mL). The aqueous portions were combined and extracted with $CHCl_3$ (75 mL). Thereafter, the $CHCl_3$ portions were combined, dried ($Na_2SO_4$), and concentrated to dryness under reduced pressure to provide an oil. To the oil was added MeOH; the mixture was then concentrated under reduced pressure. The product was heated to 40° C. and added was MeOH (45 mL) and 8N NaOH (38 mL) such that the pH was within 8 to 9 to provide a black solution. After seeding with a small amount of the desired product (the compound of formula QC1), a white precipitate formed. To the suspension containing the precipitate was added water (150 mL) and MeCN (45 mL) and the suspension was stirred at a temperature of about 25° C. for about 1.5 h. After filtration, the resulting solid was washed with 1:1 $MeCN:H_2O$ (75 mL) and dried under reduced pressure at a temperature of about 25° C. to provide 12.05 g of the compound of formula QC1 (yield 59.4%). To the filtrate at a temperature of about 25° C. was added 8N NaOH (1.5 mL) and the filtrate was stirred for 1 h to provide a white precipitate which was collected by filtration and washed with 1:1 $MeCN:H_2O$ 1:1 (75 mL) to provide an additional 3.93 g of the compound of formula QC1 (yield 19.4%; total yield 78.8%).

Under a nitrogen atmosphere, to a suspension of the compound of formula QC1 (14 g, 39.6 mmol) in toluene (140 mL) at a temperature of about 25° C. was added diethyl 2-oxomalonate (8.28 g, 47.52 mmol) and formic acid (3.34 mL, 87.12 mmol). After the addition, the resulting reaction mixture was heated to a temperature within the range from 100° C. to 110° C. and stirred for about 75 min. Thereafter, the reaction mixture was cooled to a temperature of 50° C. and EtOAc (98 mL) was added, followed by the addition of 5% aqueous $NaHCO_3$ (112 mL) and THF (15 mL) such that the pH of the mixture was within 6 to 7. The organic portion was separated and the aqueous portion extracted with EtOAc (102 mL). The organic portions were combined, dried ($Na_2SO_4$), and concentrated to dryness under reduced pressure. The residue was dissolved in THF (50 mL) at a temperature within the range from 50° C. to 55° C. To the solution was added MeOH (280 mL); a pale yellow precipitate formed at a temperature within the range from 40° C. to 45° C. After cooling to about 25° C., water (70 mL) was added to the suspension containing the precipitate. After filtration, the resulting solid was washed with MeOH (70 mL) to provide a white solid which was dried under reduced pressure at a temperature of about 25° C. to provide 13.69 g of the compound of formula QD (yield 80.3%).

To a solution of the compound of formula QC2 (500 mg, 1.078 mmol) in THF (5 mL) at a temperature of about 25° C. was added 8N KOH (0.202 mL, 1.618 mmol) in water (0.5 mL). The resulting reaction mixture was stirred at a temperature of 80° C. for 1 h so that it was clear. After cooling the reaction mixture to a temperature between 40° C. and 50° C., para-toluene sulfonic acid monohydrate (615 mg, 3.24 mmol, Sigma-Aldrich) in THF (2 mL) was added. The clear mixture was stirred at a temperature of 50° C. for 1 h; a pale yellow precipitate formed. The precipitate was collected by filtration, washed twice with 4:1 $THF:H_2O$ (5 mL for each wash), and dried under reduced pressure at 100° C. for 8 h to provide 539 mg of the tosylate salt of Substituted-Quinoxaline-Type Bridged-Piperidine Compound 362 as a pale yellow solid (yield 82%).

5.3 Example 3

Substituted-Quinoxaline-Type Bridged-Piperidine Compound 362 was also prepared as follows.

To a solution of the compound of formula LA (20.00 g, 130.5 mmol) in acetone (100 mL) at a temperature of about 25° C. was added the compound of formula EB (15.5 mL, 130.55 mmol). After the addition, the resulting reaction mixture was heated to reflux and refluxed for 24 h. The mixture was cooled to a temperature of about 25° C. and filtered to provide 34 g of the compound of formula LB as a white solid (yield 81%).

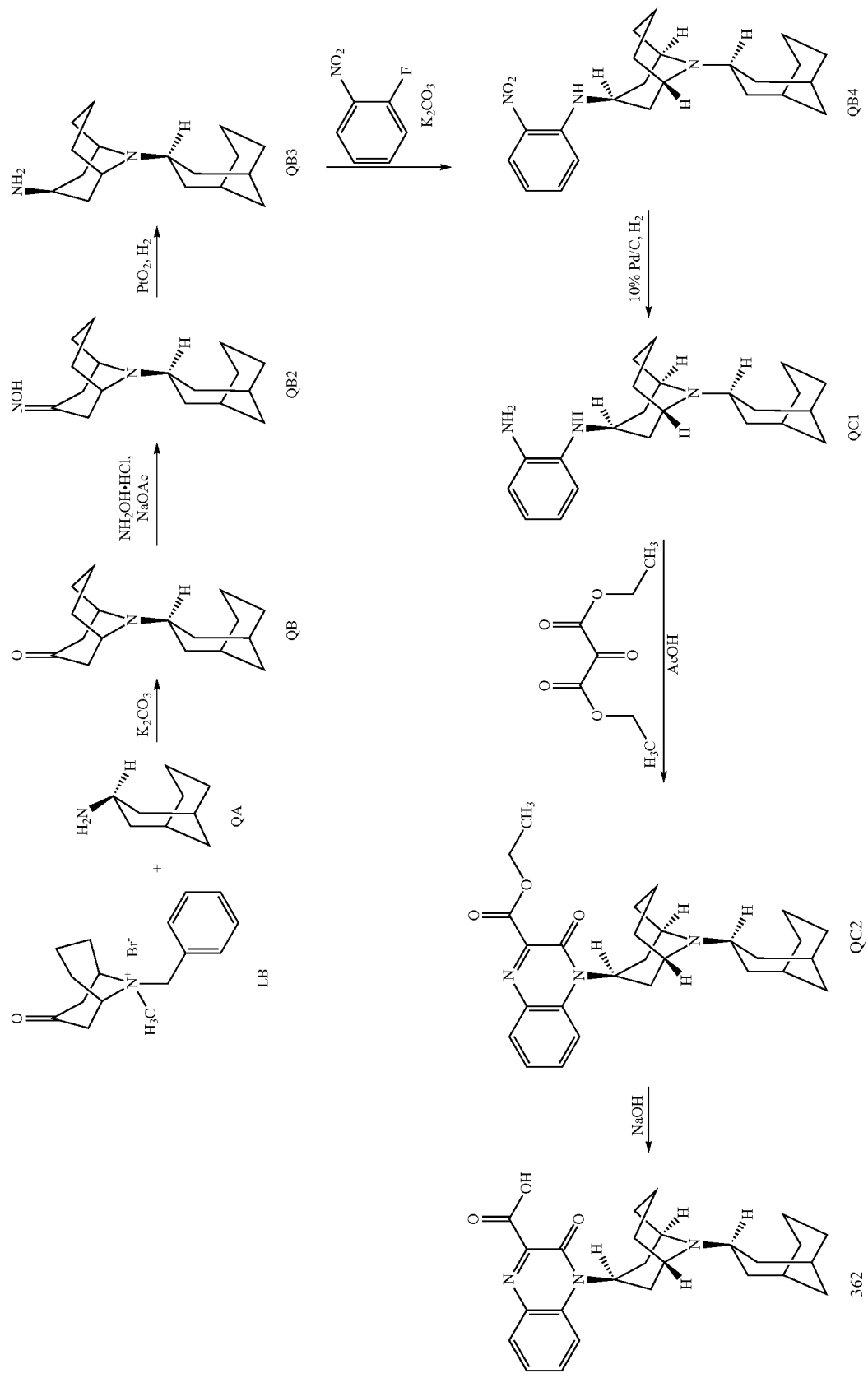

To a solution of the compound of formula QA (1.453 g, 10.44 mmol) in EtOH (3.1 mL) and water (0.7 mL) at a temperature of about 25° C. was added a mixture of $K_2CO_3$ (144 mg, 1.04 mmol), the compound of formula LB (4.06 g, 12.53 mmol), EtOH (29 mL), and water (18 mL). After the addition, the resulting reaction mixture was heated to a temperature of 90° C. and stirred for 5 h. Thereafter, the reaction mixture was cooled to a temperature of 0° C.; a white precipitate formed. The precipitate was filtered, rinsed with water, and collected to provide 1.58 g of the compound of formula QB as a white solid (yield 58%).

The identity of the compound of formula QB was confirmed using $^1$H NMR.

Compound QB: $^1$H NMR: $\delta_H$(CDCl$_3$): 1.50-1.70 (m, 14H), 1.75-1.90 (m, 2H), 1.90-2.10 (m, 4H), 2.20 (d, J=15.0 Hz, 2H), 2.60 (m, 2H), 3.35 (m, 1H), 3.66 (m, 2H).

Under a nitrogen atmosphere, to a suspension of the compound of formula QB (10.77 g, 41.2 mmol) in EtOH (215 mL) at a temperature of about 25° C. was added hydroxylamine hydrochloride (4.29 g, 61.8 mmol) and sodium acetate (5.07 g, 61.8 mmol). The resulting reaction mixture was stirred at a temperature of about 25° C. for 1.5 h. Thereafter, the mixture was cooled to a temperature of about 25° C., quenched by the addition of water (50 mL), then extracted twice with a mixture of saturated aqueous NaHCO$_3$:CHCl$_3$ (200 mL for each extraction). The organic portions were combined, dried (Na$_2$SO$_4$), and concentrated under reduced pressure to provide 11.39 g of the compound of formula QB2 as a pale yellow solid (yield>99.5%).

The identity of the compound of formula QB2, 9-((exo)-bicyclo[3.3.1]nonan-3-yl)-9-azabicyclo[3.3.1]nonan-3-one oxime, was confirmed using LC/MS.

Compound QB2: LC/MS: m/z=277.45 [M+H]$^+$ (Calc: 276.42).

To a solution of the compound of formula QB2 (11.39 g, 41.2 mmol) in AcOH (203 mL) at a temperature of about 25° C. was added platinum(IV) oxide (1.871 g, 8.24 mmol, Sigma-Aldrich). Under a hydrogen atmosphere at 5 atm pressure, the resulting reaction mixture was stirred at a temperature of about 25° C. for 24 h. Thereafter, the mixture was filtered, washed with EtOAc (100 mL), and concentrated under reduced pressure to provide a sticky yellow oil. Water was added to the oil and the mixture was neutralized by 28% aqueous ammonia to provide a white gel like precipitate. The mixture was then extracted twice with a mixture of CHCl$_3$:MeOH:H$_2$O (700 mL for each extraction), dried (MgSO$_4$), and concentrated under reduced pressure to provide 9.07 g of the endo-azabicyclo[3.3.1]nonan-3-amine form of the compound of formula QB3 as a colorless solid (yield 84%).

The identity of the compound of formula QB3, 9-(exo-bicyclo[3.3.1]nonan-3-yl)-9-endo-azabicyclo[3.3.1]nonan-3-amine, was confirmed using $^1$H NMR and LC/MS.

Compound QB3: $^1$H NMR: $\delta_H$ (400 MHz, DMSO-d$_6$): 0.92-0.99 (m, 4H), 1.23-1.65 (m, 16H), 1.98 (m, 7H), 3.12 (s, 1H), 3.28 (s, 2H); LC/MS: m/z=263.15 [M+H]$^+$ (Calc: 262.43).

Under a nitrogen atmosphere, to a solution of the compound of formula QB3 (9.07 g, 34.6 mmol) in DMF (136 mL) at a temperature of about 25° C. was added K$_2$CO$_3$ (7.16 g, 51.8 mmol) and 1-fluoro-2-nitrobenzene (3.65 mL, 34.6 mmol, Sigma-Aldrich). The resulting reaction mixture was heated at 100° C. and stirred for 2 h. Thereafter, the mixture was cooled to a temperature of about 25° C. and quenched by the addition of ice-water (100 mL) and saturated aqueous NaHCO$_3$ (10 mL); a yellow precipitate formed. The precipitate was collected by filtration, washed twice with water (50 mL for each wash), and dried at 70° C. for 8 h under reduced pressure to provide 11.98 g of the compound of formula QB4 as a yellow solid (yield 90%).

The identity of the compound of formula QB4,9-((exo)-bicyclo[3.3.1]nonan-3-yl)-N-(2-nitrophenyl)-9-(endo)-azabicyclo[3.3.1]nonan-3-amine, was confirmed using $^1$H NMR and LC/MS.

Compound QB4: $^1$H NMR: $\delta_H$ (400 MHz, CDCl$_3$): 0.85-2.02 (m, 26H), 2.45 (m, 2H), 3.49 (m, 3H), 4.03 (t, J=3.79 Hz, 1H), 6.58 (t, J=7.58 Hz, 1H), 6.93 (d, J=8.08 Hz, 1H), 7.40 (t, J=7.33 Hz, 1H), 8.09 (dd, J=48.50, 7.58 Hz, 2H); LC/MS: m/z=384.2 [M+H]$^+$ (Calc: 383.5).

Under a hydrogen atmosphere, to a suspension of the compound of formula QB4 (11.98 g, 31.2 mmol) in MeOH (50 mL) at a temperature of about 25° C. was added 10% palladium on carbon (1.330 g, 1.249 mmol). After the addition, the resulting reaction mixture was stirred at a temperature of about 25° C. for 1.5 h. Thereafter, CHCl$_3$ (150 mL) was added and the mixture was filtered, washed with CHCl$_3$, and concentrated under reduced pressure to provide 11.04 g of the compound of formula QC1 as a pale green solid (yield>99.5%). The identity of the compound of formula QC1 was confirmed using $^1$H NMR and LC/MS.

Under a nitrogen atmosphere, to a solution of the compound of formula QC1 (11.04 g, 31.2 mmol) in toluene (220 mL) at a temperature of about 25° C. was added diethyl 2-oxomalonate (6.02 mL, 37.5 mmol) and AcOH (2.143 mL, 37.5). After the addition, the resulting reaction mixture was heated to a temperature of 130° C. and stirred for 1 h. Thereafter, the reaction mixture was cooled to a temperature of about 25° C. and concentrated under reduced pressure to provide a sticky oil. The oil was diluted with saturated aqueous NaHCO$_3$, extracted twice with CHCl$_3$ (600 mL for each extraction), dried (Na$_2$SO$_4$), and concentrated under reduced pressure to provide an orange solid. The solid was sonicated using 4:1 n-hexane:Et$_2$O, collected by filtration, and dried under reduced pressure at 65° C. for 8 h to provide a first portion of the compound of formula QC2 as a pale yellow solid. The remaining filtrate was chromatographed with a silica gel column eluted with a gradient of from 100%:0% CHCl$_3$:MeOH to 95%:5% CHCl$_3$:MeOH to provide a second portion of the compound of formula QC2 as a pale yellow solid; a total of 9.83 g was obtained (combined yield 67%). The identity of the compound of formula QC2 was confirmed using $^1$H NMR and LC/MS.

Thereafter, Substituted-Quinoxaline-Type Bridged-Piperidine Compound 362 was prepared from the compound of formula QC2 as described in Example 1. The identity of Substituted-Quinoxaline-Type Bridged-Piperidine Compound 362 was confirmed using $^1$H NMR and LC/MS.

5.4 Example 4

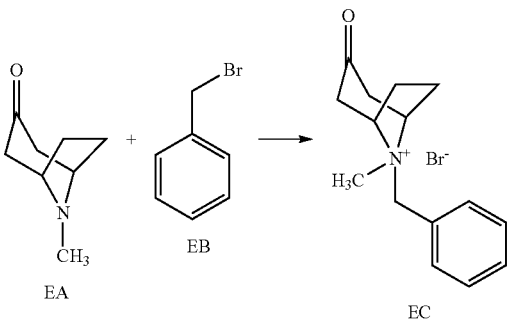

The compound of formula EB (6.5 g, 38 mmol) was added to a mixture of the compound of formula EA, 8-methyl-8-azabicyclo[3.2.1]octan-3-one (5 g, 36 mmol, Sigma-Aldrich), in acetone (100 mL) over 30 min at a temperature of about 25° C. The resulting reaction mixture was stirred at a temperature of about 25° C. for 1 h then at 38° C. for 2 h. Thereafter, the mixture was cooled to a temperature of about 25° C., filtered, and washed twice with hexanes (10 mL for each wash) to provide 10 g of the compound of formula EC, 8-benzyl-8-methyl-3-oxo-8-azoniabicyclo[3.2.1]octane bromide, as white solid (yield 85%).

of from 20%:80% EtOAc:n-hexane to 80%:20% EtOAc:n-hexane to provide 2030 mg of the compound of formula RA as a colorless solid (yield 50%).

The identity of the compound of formula RA, 8-((exo)-bicyclo[3.3.1]nonan-3-yl)-8-azabicyclo[3.2.1]octan-3-one, was confirmed using $^1$H NMR and LC/MS.

Compound RA: $^1$H NMR: $\delta_H$ (400 MHz, CDCl$_3$): 1.79 (m, 12H), 2.26 (m, 8H), 2.87 (d, J=13.64 Hz, 2H), 3.52 (td, J=11.12, 5.56 Hz, 1H), 3.99 (s, 2H); LC/MS: m/z=248.5 [M+H]$^+$ (Calc: 247).

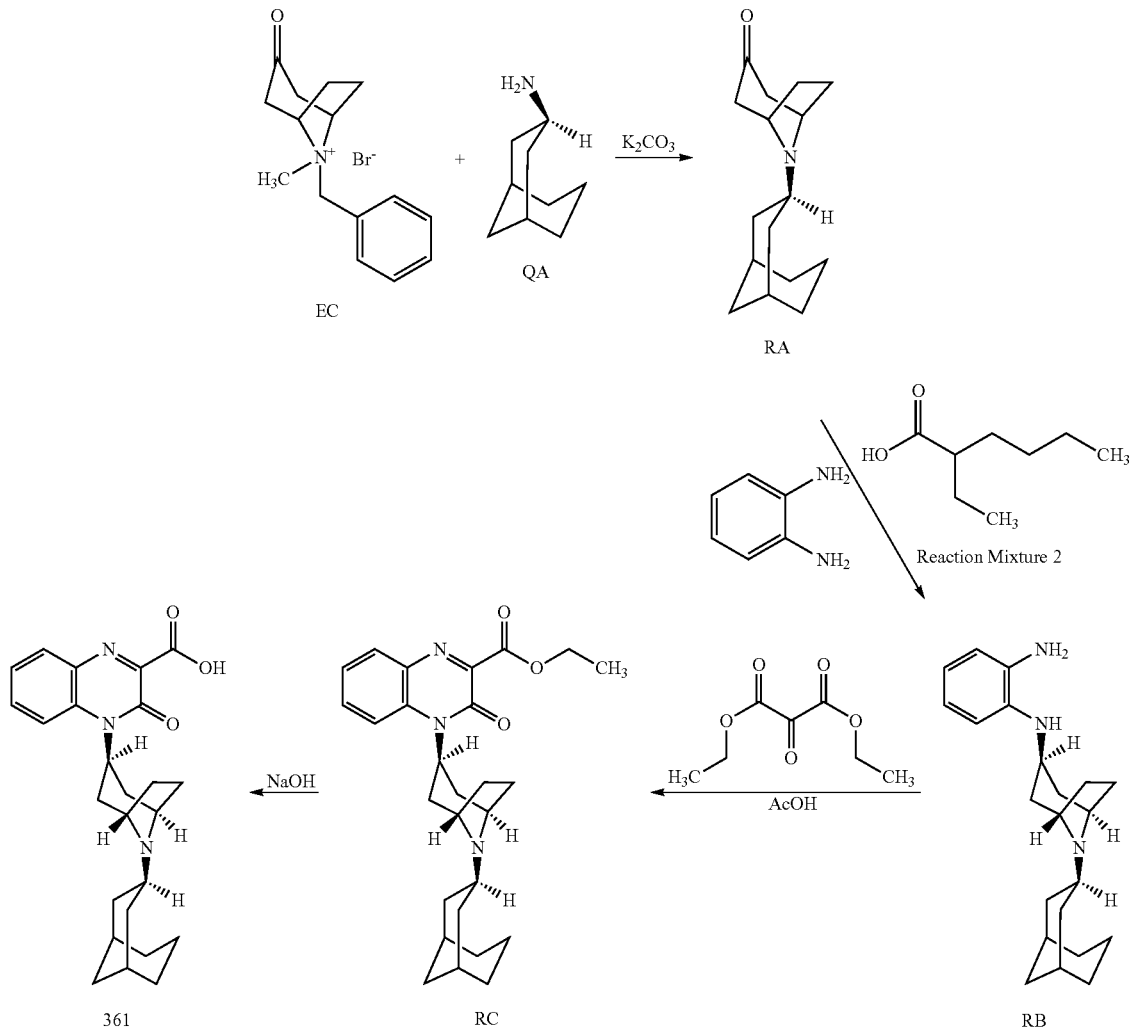

To a mixture of the compound of formula QA (2270 mg, 16.30 mmol), K$_2$CO$_3$ (225.3 mg, 1.63 mmol), EtOH (20 mL), and water (5 mL) at a temperature of about 25° C. was added dropwise a mixture of the compound of formula EC (5058 mg, 16.30 mmol), EtOH (20 mL), and water (27 mL). After the addition, the resulting reaction mixture was heated to a temperature of 90° C. and stirred for 4 h. Thereafter, the reaction mixture was cooled to a temperature of about 25° C., diluted with saturated aqueous NaHCO$_3$, then extracted twice with EtOAc:H$_2$O (100 mL for each extraction). The organic portions were combined, dried (Na$_2$SO$_4$), and concentrated under reduced pressure to provide an oil. The oil was chromatographed with a silica gel column eluted with a gradient Under a nitrogen atmosphere, to a solution of the compound of formula RA (2029 mg, 8.20 mmol) in CH$_2$Cl$_2$ (25 mL) at a temperature of about 25° C. was added 1,2-phenylenediamine (2661 mg, 24.61 mmol) and 2-ethylhexanoic acid (1.971 mL, 12.30 mmol). The mixture was stirred at a temperature of about 25° C. for 30 min to provide reaction mixture 1.

Under a nitrogen atmosphere, to reaction mixture 1 at 0° C. was added reaction mixture 2 dropwise over a 15 min period. After the addition, the resulting reaction mixture was heated to a temperature of about 25° C. and stirred for 30 min. Thereafter, the reaction mixture was heated to a temperature of 60° C. and stirred for 16 h. After cooling the reaction mixture to a temperature of about 25° C., saturated aqueous NaHCO₃ (20 mL) was added, the mixture stirred for 10 min, then extracted twice with 1M aqueous K₂CO₃/EtOAc (150 mL for each extraction). The organic portions were combined, dried (Na₂SO₄), and concentrated under reduced pressure to provide a yellow oil. The oil was chromatographed with a silica gel column eluted with a gradient of from 97%:3% CHCl₃: (10% NH₃ in MeOH) to 80%:20% CHCl₃: (10% NH₃ in MeOH) to provide 874 mg of the compound of formula RB as a pale yellow amorphous solid (yield 31%).

The identity of the compound of formula RB, N¹-((endo)-8-((exo)-bicyclo[3.3.1]nonan-3-yl)-8-azabicyclo[3.2.1]octan-3-yl)benzene-1,2-diamine, was confirmed using ¹H NMR and LC/MS.

Compound RB: ¹H NMR: $\delta_H$ (400 MHz, CDCl₃): 0.91 (m, 3H), 1.26-2.10 (m, 20H), 2.35 (m, 2H), 3.28-3.33 (m, 1H), 3.69 (m, 3H), 6.57 (d, J=7.58 Hz, 1H), 6.75 (m, 3H); LC/MS: m/z=340.6 [M+H]⁺ (Calc: 339).

Under a nitrogen atmosphere, to a solution of the compound of formula RB (870 mg, 2.56 mmol) in xylene (15 mL) at a temperature of about 25° C. was added diethyl 2-oxomalonate (0.494 mL, 3.07 mmol) and AcOH (0.176 mL, 3.07 mmol). After the addition, the resulting reaction mixture was heated to a temperature of 130° C. and stirred for 1 h. Thereafter, the reaction mixture was cooled to a temperature of about 25° C., diluted with saturated aqueous NaHCO₃, extracted twice with EtOAc (100 mL for each extraction), dried (Na₂SO₄), and concentrated under reduced pressure to provide an orange oil. The oil was chromatographed with an amino-silica gel column (Yamazen Corp. WO91-01) eluted with a gradient of from 5%:95% EtOAc:n-hexane to 30%:70% EtOAc:n-hexane to provide a pale yellow solid. The solid was triturated with 1:4 Et₂O:n-hexane and dried under reduced pressure at 70° C. to provide 343 mg of the compound of formula RC as a colorless solid (yield 30%).

The identity of the compound of formula RC, ethyl 4-((endo)-8-((exo)-bicyclo[3.3.1]nonan-3-yl)-8-azabicyclo[3.2.1]octan-3-yl)-3-oxo-3,4-dihydroquinoxaline-2-carboxylate, was confirmed using ¹H NMR and LC/MS.

Compound RC: ¹H NMR: $\delta_H$ (400 MHz, CDCl₃): 0.83-0.88 (m, 1H), 1.26 (dd, J=33.09, 17.94 Hz, 3H), 1.51 (m, 11H), 1.91 (m, 8H), 2.20 (s, 3H), 2.79 (dt, J=11.62 Hz, 3.66 Hz, 1H), 3.70 (s, 2H), 4.50 (q, J=7.07 Hz, 2H), 5.20 (br, 1H), 7.34 (t, J=7.07 Hz, 1H), 7.61 (q, J=7.92 Hz, 2H), 7.91 (d, J=7.58 Hz, 1H); LC/MS: m/z=450.1 [M+H]⁺ (Calc: 449).

To a solution of the compound of formula RC (343 mg, 0.763 mmol) in EtOH (10 mL) at a temperature of about 25° C. was added 2N aqueous NaOH (1.144 mL, 2.289 mmol). The resulting reaction mixture was stirred at a temperature of about 25° C. for 1 h. Thereafter, the reaction mixture was concentrated under reduced pressure to provide a residue. The residue was diluted with water (2 mL) to form a pale yellow solution, neutralized with 2N aqueous HCl (1.144 mL), and sonicated to provide a white precipitate. The precipitate was collected by filtration, washed with water, and dried at 75° C. for 8 h under reduced pressure to provide 312 mg of Substituted-Quinoxaline-Type Bridged-Piperidine Compound 361 as a colorless solid (yield 97%).

The identity of Substituted-Quinoxaline-Type Bridged-Piperidine Compound 361, 4-((endo)-8-((exo)-bicyclo[3.3.1]nonan-3-yl)-8-azabicyclo[3.2.1]octan-3-yl)-3-oxo-3,4-dihydroquinoxaline-2-carboxylic acid, was confirmed using ¹H NMR and LC/MS.

Substituted-Quinoxaline-Type Bridged-Piperidine Compound 361: ¹H NMR: $\delta_H$ (400 MHz, CDCl₃): 0.86 (m, 2H), 1.64 (m, 6H), 1.89 (m, 1H), 2.03 (dq, J=9.09, 2.44 Hz, 2H), 2.42 (m, 9H), 3.01 (m, 2H), 3.49 (s, 1H), 4.26 (d, J=1.01 Hz, 2H), 6.55 (s, 1H), 7.55 (t, J=7.33 Hz, 1H), 7.92 (dd, J=9.85, 5.81 Hz, 1H), 8.18 (d, J=7.58 Hz, 1H), 8.40 (d, J=8.59 Hz, 1H), 11.41 (s, 1H); LC/MS (100%, $t_r$=1.38 min): m/z=422.5 [M+H]⁺ (Calc: 421.5).

5.5 Example 5

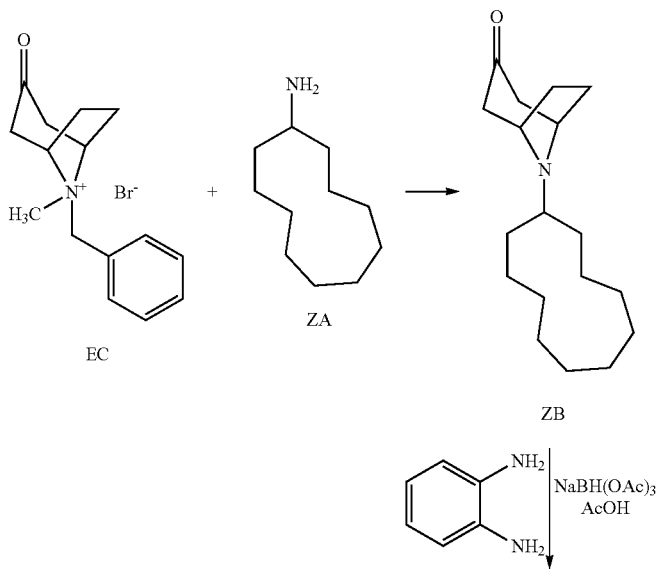

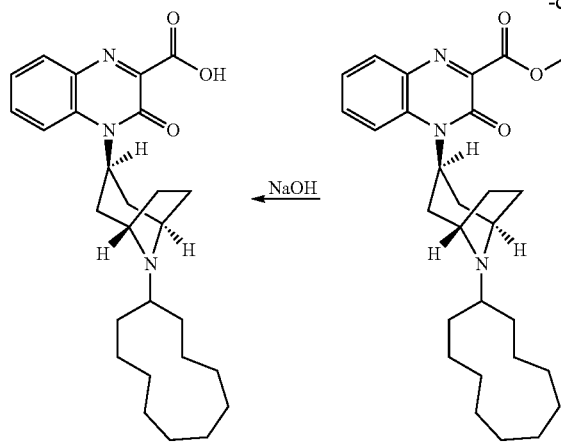

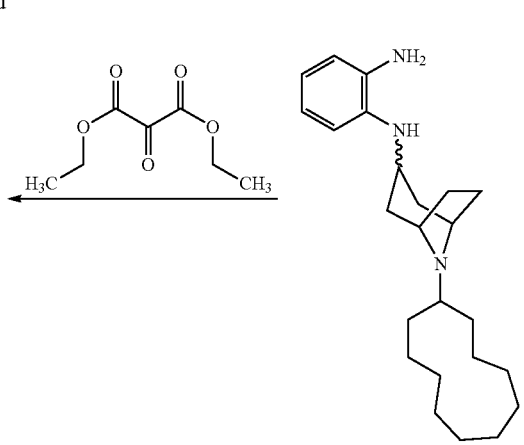

The compound of formula EC was mixed with 2:1 EtOH:H$_2$O. Over 30 min, this mixture was added to a mixture of the compound of formula ZA (cycloundecanamine, Sigma-Aldrich) and K$_2$CO$_3$ in EtOH at 70° C. After 3 h at 70° C., the reaction mixture was cooled to a temperature of about 25° C. and concentrated under reduced pressure. The residue was treated with water and extracted three times with CHCl$_3$. The combined organic portions were washed with brine and concentrated under reduced pressure to provide the compound of formula ZB.

The identity of the compound of formula ZB, 8-cycloundecyl-8-azabicyclo[3.2.1]octan-3-one, was confirmed using $^1$H NMR.

Compound ZB: $^1$H NMR: $\delta_H$ (400 MHz, CDCl$_3$): 1.46-1.77 (m, 22H), 1.97 (m, 2H), 2.14 (d, J=16.22 Hz, 2H), 2.64 (d, J=16.22 Hz, 2H), 2.73 (m, 1H), 3.77 (s, 2H).

Sodium triacetoxyborohydride (Sigma-Aldrich) was added to a mixture of the compound of formula ZB and 1,2-phenylenediamine in CH$_2$Cl$_2$ at a temperature of about 25° C. Thereafter, acetic acid was added. The resulting reaction mixture was stirred at a temperature of about 25° C. for about 16 h. Thereafter, MeOH and water were added and the mixture was neutralized with 28% aqueous ammonia to adjust the pH to about 8. The organic portion was separated, washed with brine, concentrated under reduced pressure, and chromatographed with a silica gel column eluted with 10:1:1 EtOAc:MeOH:TEA to provide a mixture of the endo and exo isomers of the compound of formula ZC.

The identity of the compound of formula ZC, N$^1$-(8-cycloundecyl-8-azabicyclo[3.2.1]octan-3-yl)benzene-1,2-diamine, was confirmed using $^1$H NMR and LC/MS.

Compound ZC: $^1$H NMR: $\delta_H$(CDCl$_3$): 1.57 (m, 22H), 2.00 (m, 4H), 2.23 (m, 2H), 2.47 (m, 1H), 3.33 (m, 2H), 3.48 (m, 3H), 3.68 (m, 1H), 6.57 (d, J=7.72 Hz, 1H), 6.69 (t, J=7.72 Hz, 1H), 6.76 (d, J=7.55 Hz, 1H), 6.84 (t, J=7.55 Hz, 1H); LC/MS: m/z=370 [M+H]$^+$ (Calc: 369.6).

Diethyl 2-oxomalonate was added dropwise to a suspension of the compound of formula ZC in toluene at 25° C. The resulting reaction mixture was stirred at 130° C. for 4 hr. After cooling to a temperature of about 25° C. and concentrating under reduced pressure, an oil was obtained. The oil was chromatographed with a silica gel column eluted with a gradient of from 99%:1% CHCl$_3$:MeOH to 95%:5% CHCl$_3$:MeOH to provide an amorphous solid. The solid was chromatographed with a silica gel column eluted with a gradient of from 95%:5% EtOAc:MeOH to 90%:10% EtOAc:MeOH to provide the compound of formula ZD.

The identity of the compound of formula ZD, ethyl 4-((endo)-8-cycloundecyl-8-azabicyclo[3.2.1]octan-3-yl)-3-oxo-3,4-dihydroquinoxaline-2-carboxylate, was confirmed using $^1$H NMR and LC/MS.

Compound ZD: $^1$H NMR: $\delta_H$ (CDCl$_3$): 1.30-1.70 (m, 24H), 1.83 (m, 2H), 2.00 (m, 2H), 2.25 (m, 5H), 3.66 (m, 2H), 4.50 (d, J=7.14 Hz, 2H), 5.20 (br, 1H), 7.36 (t, J=7.60 Hz, 1H), 7.56 (d, J=7.60 Hz, 1H), 7.60 (t, J=7.60 Hz, 1H), 7.91 (d, J=7.60 Hz, 1H); LC/MS: m/z=480 [M+H]$^+$ (Calc: 479.6).

To a mixture of the compound of formula ZD in MeOH at a temperature of about 25° C. was added 2N aqueous NaOH. The resulting reaction mixture was stirred for 2 h at a temperature of about 25° C. After concentration under reduced pressure, the mixture was diluted with water then extracted with EtOAc. The aqueous portion was neutralized by adding a first treatment of 2N aqueous HCl at a temperature of 0° C. Thereafter, the mixture was extracted twice with CHCl$_3$. The organic portions were combined, dried (MgSO$_4$), filtrated, and concentrated under reduced pressure to provide Substituted-Quinoxaline-Type Bridged-Piperidine Compound 358.

The identity of Substituted-Quinoxaline-Type Bridged-Piperidine Compound 358, 4-((endo)-8-cycloundecyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Bridged-Piperidine Compound 358: $^1$H NMR: $\delta_H$ (CDCl$_3$): 1.30-1.60 (m, 14H), 1.75 (m, 2H), 2.13 (m, 6H), 2.39 (m, 4H), 2.61 (m, 1H), 3.04 (m, 2H), 4.12 (m, 2H), 5.83 (m, 1H), 7.25 (m, 1H), 7.44 (m, 1H), 7.85-7.94 (m, 2H); LC/MS (99%, t$_r$=2.06 min): m/z=452 [M+H]$^+$ (Calc: 451.6).

5.6 Example 6

In a manner similar to Example 5, the compound of formula SA and Substituted-Quinoxaline-Type Bridged-Piperidine Compound 356 were prepared from the compound of formula EC by using cyclododecanamine (Sigma-Aldrich) in place of the compound of formula ZD.

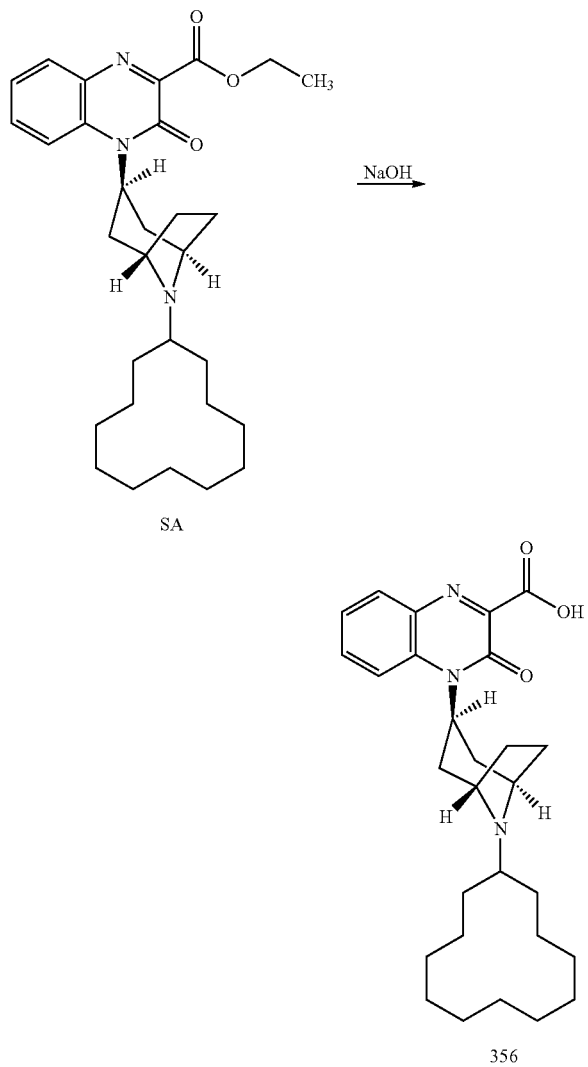

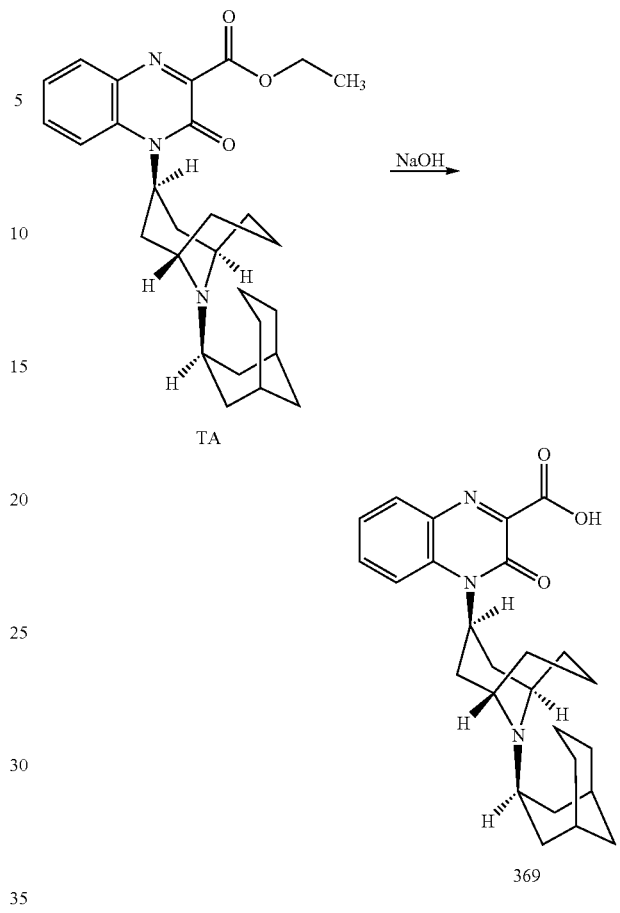

The identity of the compound of formula SA, ethyl 4-((endo)-8-cyclododecyl-8-azabicyclo[3.2.1]octan-3-yl)-3-oxo-3,4-dihydroquinoxaline-2-carboxylate, was confirmed using $^1$H NMR and LC/MS.

Compound SA: $^1$H NMR: $\delta_H$ (CDCl$_3$): 1.35 (m, 25.0H), 1.82 (m, 2.0H), 2.02 (m, 2.0H), 2.26 (m, 5.0H), 3.68 (m, 2.0H), 4.49 (q, J=7.10 Hz, 2.0H), 5.20 (br, 1.0H), 7.34 (t, J=7.60 Hz, 1.0H), 7.54 (d, J=7.60 Hz, 1.0H), 7.62 (t, J=7.60 Hz, 1.0H), 7.91 (d, J=7.60 Hz, 1.0H); LC/MS: m/z=494 [M+H]$^+$ (Calc: 493.6).

The identity of Substituted-Quinoxaline-Type Bridged-Piperidine Compound 356, 4-((endo)-8-cyclododecyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Bridged-Piperidine Compound 356: $^1$H NMR: $\delta_H$ (CDCl$_3$): 1.42 (m, 16.0H), 1.60-2.60 (m, 12.0H), 2.72 (s, 1.0H), 3.06 (m, 2.0H), 4.16 (s, 2.0H), 6.00 (br, 1.0H), 7.32 (t, J=7.35 Hz, 1.0H), 7.60 (m, 1.0H), 7.93 (d, J=8.11 Hz, 1.0H), 8.10 (m, 1.0H); LC/MS (100%, t$_r$=2.20 min): m/z=466 [M+H]$^+$ (Calc: 465.6).

5.7 Example 7

In a manner similar to Example 1, the following Substituted-Quinoxaline-Type Bridged-Piperidine Compound was prepared from the compound of formula LB.

The compound of formula TA (yield 8% for three steps) and Substituted-Quinoxaline-Type Bridged-Piperidine Compound 369 (yield 91%) were prepared from the compound of formula LB by using (endo)-bicyclo[3.3.1]nonan-3-amine (QI) in place of the compound of formula QA.

The identity of the compound of formula TA, ethyl 4-((endo)-9-((endo)-bicyclo[3.3.1]nonan-3-yl)-9-azabicyclo[3.3.1]nonan-3-yl)-3-oxo-3,4-dihydroquinoxaline-2-carboxylate, was confirmed using $^1$H NMR and LC/MS.

Compound TA: $^1$H NMR: $\delta_H$ (400 MHz, CDCl$_3$): 0.98-1.12 (m, 5H), 1.26 (s, 1H), 1.43 (m, 7H), 1.57 (m, 1H), 1.75-1.85 (m, 5H), 2.10 (m, 5H), 2.40-2.45 (m, 1H), 2.72 (br, 2H), 3.00-3.07 (m, 1H), 3.53 (d, J=10.11 Hz, 2H), 4.51 (q, J=7.07 Hz, 2H), 5.20 (br, 1H), 7.36 (t, J=3.54 Hz, 1H), 7.65 (s, 2H), 7.93 (d, J=8.08 Hz, 1H); LC/MS: m/z=464.1 [M+H]$^+$ (Calc: 463).

The identity of Substituted-Quinoxaline-Type Bridged-Piperidine Compound 369, 4-((endo)-9-((endo)-bicyclo[3.3.1]nonan-3-yl)-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Bridged-Piperidine Compound 369: $^1$H NMR: $\delta_H$ (400 MHz, CDCl$_3$): 0.84-0.89 (m, 1H), 1.27 (m, 4H), 1.40-1.52 (m, 2H), 1.66 (m, 5H), 1.85 (m, 1H), 2.11 (m, 2H), 2.28 (s, 4H), 2.50 (m, 2H), 2.76 (m, 1H), 3.00 (t, J=12.63 Hz, 2H), 3.69-3.74 (m, 1H), 4.16 (d, J=10.11 Hz, 2H), 6.78 (s, 1H), 7.56 (t, J=7.58 Hz, 1H), 7.93 (t, J=7.83 Hz, 1H), 8.19 (d, J=8.08 Hz, 1H), 9.07 (t, J=7.58 Hz, 1H), 11.08 (s, 1H); LC/MS (100%, t$_r$=1.55 min): m/z=436.2 [M+H]$^+$ (Calc: 436).

The compound of formula QI was prepared as follows.

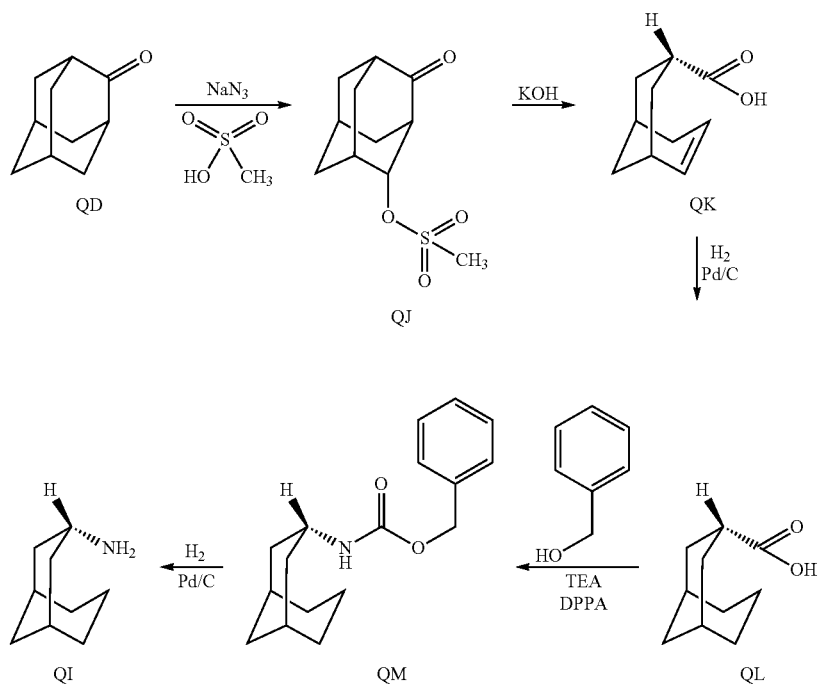

Under a nitrogen atmosphere, to a solution of the compound of formula QD (6.0 g, 39.9 mmol) in methane sulfonic acid (33.7 mL, 519 mmol) at a temperature of 20° C. was added sodium azide (2.726 g, 41.9 mmol) portionwise over 2.5 h. After the addition, the resulting reaction mixture was stirred for 3 days at 20° C. Thereafter, ice-water (300 mL) was poured into the reaction mixture to provide a white precipitate that was collected by filtration, washed with water, and dried at 40° C. for 6 h under reduced pressure to provide 5.63 g of the compound of formula QJ as a colorless solid with a melting point of 69-72° C. (yield 58%).

The identity of the compound of formula QJ, methane sulfonic acid 4-oxo-adamantan-2-yl ester, was confirmed using $^1$H NMR.

Compound QJ: $^1$H NMR: $\delta_H$ (400 MHz, CDCl$_3$): 1.75-2.12 (m, 9H), 2.31 (m, 1H), 2.41-2.50 (m, 2H), 2.58 (s, 1H), 2.88 (s, 1H), 3.05 (d, J=6.59 Hz, 3H), 4.80 (t, J=3.55 Hz, 1H).

To a solution of the compound of formula QJ (5.63 g, 23.04 mmol) in EtOH (100 mL) at a temperature of about 25° C. was added a KOH (8.469 g, 15 µmol) in water (67 mL) solution. After the addition, the resulting reaction mixture was heated to a temperature of 110° C. and stirred for 12 h. Thereafter, the reaction mixture was cooled to a temperature of about 25° C., 10% aqueous HCl was added such that the pH was within 3 to 4, and a colorless precipitate formed. The precipitate was collected by filtration, washed with water, concentrated under reduce pressure, and dried at 50° C. for 8 h under reduced pressure to provide 3.61 g of the compound of formula QK as a colorless solid with a melting point of 189-192° C. (yield 94%).

The identity of the compound of formula QK, (endo)-bicyclo[3.3.1]non-6-ene-3-carboxylic acid, was confirmed using $^1$H NMR.

Compound QK: $^1$H NMR: $\delta_H$ (400 MHz, CDCl$_3$): 1.64 (m, 4H), 2.07-2.42 (m, 6H), 2.58 (t, J=6.32 Hz, 1H), 5.57-5.68 (m, 2H).

In a manner similar to the preparation of the compound of formula QF above, the compound of formula QL was prepared from the compound of formula QK (yield 99%).

The identity of the compound of formula QL, (endo)-bicyclo[3.3.1]nonane-3-carboxylic acid, was confirmed using $^1$H NMR.

Compound QL: $^1$H NMR: $\delta_H$ (400 MHz, CDCl$_3$): 1.17 (d, J=13.18 Hz, 1H), 1.37-1.82 (m, 10H), 2.12 (m, 4H), 2.51-2.60 (m, 1H).

In a manner similar to the preparation of the compound of formula QH above, the compound of formula N was prepared from the compound of formula QL (yield 90%).

The identity of the compound of formula QM, benzyl (endo)-bicyclo[3.3.1]nonan-3-ylcarbamate, was confirmed using $^1$H NMR and LC/MS.

Compound QM: $^1$H NMR: $\delta_H$ (400 MHz, CDCl$_3$): 1.31 (m, 2H), 1.44-1.76 (m, 9H), 2.04 (s, 2H), 2.09 (s, 2H), 4.31-4.40 (m, 2H), 5.08 (s, 2H), 7.28-7.39 (m, 5H); LC/MS: m/z=274.2 [M+H]$^+$ (Calc: 273).

Under a hydrogen atmosphere, a mixture of the compound of formula QM (4.11 g, 15.03 mmol), 10% palladium on carbon (0.64 g, 0.601 mmol), and EtOH (45 mL) was stirred at a temperature of about 25° C. for 3 h. After filtering off the Pd/C and washing with EtOH, the mixture was concentrated under reduced pressure to a volume of 10 mL. The EtOH solution contained 2.093 g (15.03 mmol) of the compound of formula QI.

5.8 Example 8

In a manner similar to Example 4, the compound of formula UA (yield 4% for three steps) and Substituted-Quinoxaline-Type Bridged-Piperidine Compound 360 (yield 87%) were prepared from the compound of formula EC by using the compound of formula QI in place of the compound of formula QA.

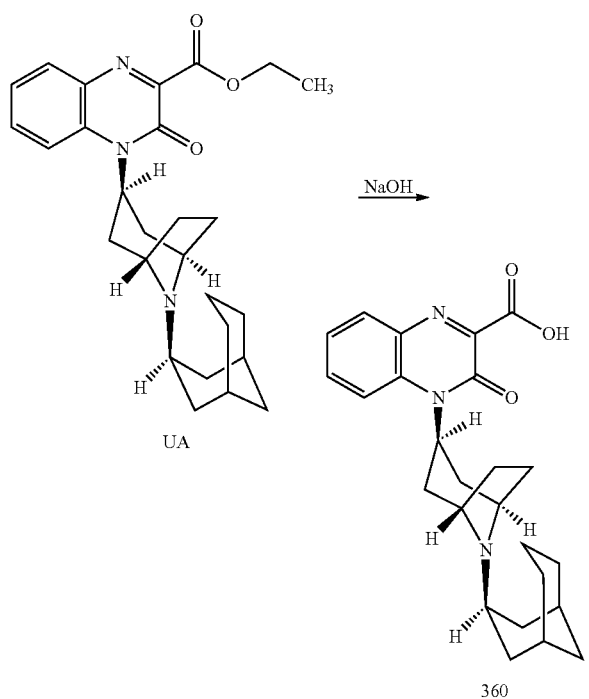

The identity of the compound of formula UA, ethyl 4-((endo)-8-((endo)-bicyclo[3.3.1]nonan-3-yl)-8-azabicyclo[3.2.1]octan-3-yl)-3-oxo-3,4-dihydroquinoxaline-2-carboxylate, was confirmed using $^1$H NMR and LC/MS.

Compound UA: $^1$H NMR: $\delta_H$ (400 MHz, CDCl$_3$): 0.86 (dq, J=10.11, 2.69 Hz, 1H), 1.07 (m, 3H), 1.21-1.45 (m, 10H), 1.65-2.37 (m, 15H), 3.67 (t, J=2.53 Hz, 2H), 4.50 (q, J=7.07 Hz, 2H), 5.18 (br, 1H), 7.35 (t, J=7.33 Hz, 1H), 7.60 (t, J=9.60 Hz, 2H), 7.91 (d, J=8.08 Hz, 1H); LC/MS: m/z=450.2 [M+H]$^+$ (Calc: 449).

The identity of Substituted-Quinoxaline-Type Bridged-Piperidine Compound 360, 4-((endo)-8-((endo)-bicyclo[3.3.1]nonan-3-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Bridged-Piperidine Compound 360: NMR: $\delta_H$ (400 MHz, CDCl$_3$): 0.84-0.88 (m, 4H), 1.38-1.46 (m, 1H), 1.54-1.65 (m, 3H), 2.27 (m, 6H), 2.46 (dt, J=12.80 Hz, 4.93 Hz, 3H), 2.95 (br, 3H), 4.25 (s, 2H), 6.61 (s, 1H), 7.51 (d, J=8.08 Hz, 1H), 7.88 (dd, J=9.60, 5.05 Hz, 1H), 8.14 (d, J=8.59 Hz, 1H), 8.44 (d, J=4.04 Hz, 1H), 11.55 (s, 1H); LC/MS (100%, t$_r$=1.48 min): m/z=422.2 [M+H]$^+$ (Calc: 421.5).

5.9 Example 9

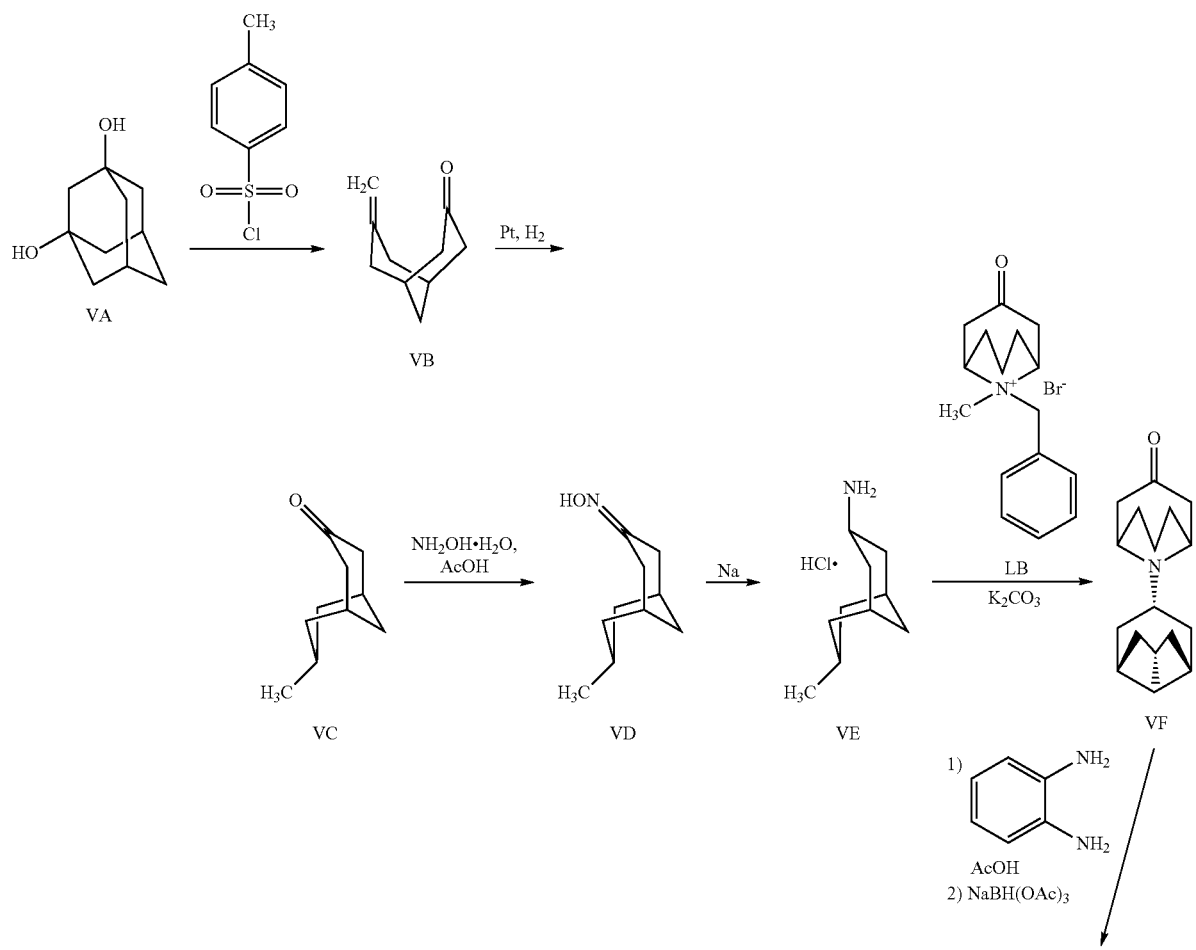

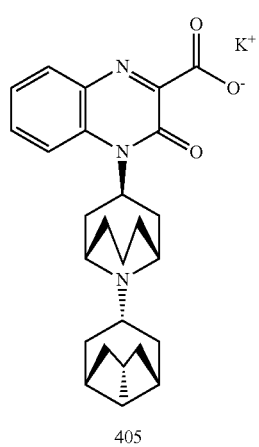 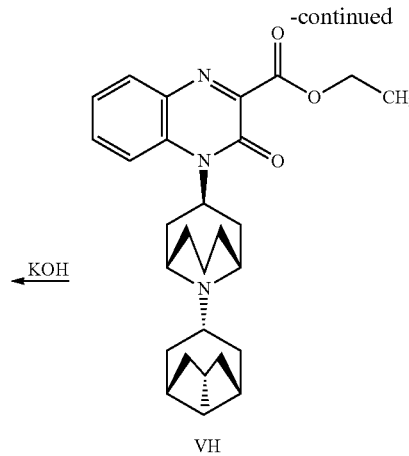 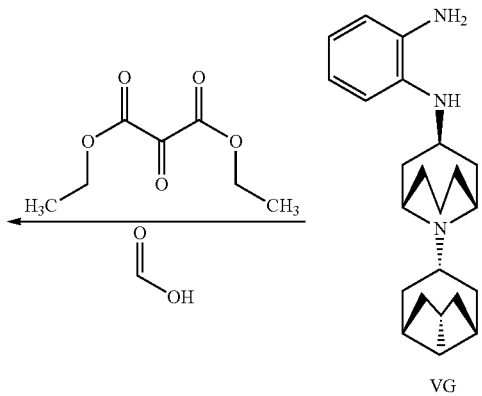

405　　　　　　　　　　VH　　　　　　　　　　　　VG

To a solution of the compound of formula VA (1,3-dihydroxyadamantane, 50.0 g, 297.3 mmol, Sigma-Aldrich) in pyridine (150 mL) at a temperature of about 25° C. was added 4-methylbenzene-1-sulfonyl chloride (62.4 g, 327.0 mmol, Sigma-Aldrich). The resulting reaction mixture was heated at 70° C. for 6 h. After cooling to a temperature of about 25° C., the mixture was poured into saturated aqueous brine solution (1 L) and that mixture was extracted twice with 1:1 $Et_2O$:hexanes (1 L for each extraction). The organic portions were combined, washed with brine (1 L), dried ($MgSO_4$), and concentrated to dryness under reduced pressure to provide a pale yellow solid. The residue was chromatographed with a silica gel column eluted with 100:10:1 hexanes:EtOAc:TEA to provide 29.0 g of the compound of formula VB as a white solid (yield 65%).

The identity of the compound of formula VB, 7-methylenebicyclo[3.3.1]nonan-3-one, was confirmed using $^1H$ NMR.

Compound VB: $^1$H NMR: $\delta_H$ (400 MHz, $CDCl_3$): 4.70 (2H, s), 2.40-2.13 (12H, m), 1.87 (2H, m).

Under a hydrogen atmosphere, to a solution of the compound of formula VB (5.0 g, 38.29 mmol) in cyclohexane (100 mL) at a temperature of about 25° C. was added platinum black (250 mg, Sigma-Aldrich). The resulting reaction mixture was stirred vigorously at a temperature of about 25° C. for 24 h. The mixture was filtered and the filtrate evaporated to dryness under reduced pressure to provide the compound of formula VC 7-methylbicyclo[3.3.1]nonan-3-one, as a pale yellow oil.

To a solution of the compound of formula VC from the previous step in acetic acid (20 mL) at a temperature of about 25° C. was added 50% aqueous hydroxylamine (5 mL). The resulting reaction mixture was heated at 70° C. for 2 h. Thereafter, the mixture was poured into 8% aqueous sodium bicarbonate solution (250 mL), extracted twice with EtOAc (250 mL for each extraction), dried ($MgSO_4$), and evaporated to dryness under reduced pressure to provide a residue. The residue was recrystallized from hexanes (50 mL) at −10° C. to provide 1.90 g of a first portion of the compound of formula VD. The filtrate was concentrated to dryness under reduced pressure and chromatographed with a silica gel column eluted with 1:1 hexanes:EtOAc to provide a 2.15 g second portion of the compound of formula VD.

The identity of the compound of formula VD, 7-methylbicyclo[3.3.1]nonan-3-one oxime, was confirmed using $^1$H NMR and TLC.

Compound VD: $^1$H NMR: $\delta_H$ (400 MHz, $CDCl_3$): 7.8 (1H, bs), 3.2 (1H, d, J=12 Hz), 2.40-2.10 (4H, m), 2.00-1.73 (4H, m), 1.55 (1H, m), 1.32 (1H, d, J=12 Hz), 0.80 (4H, m), 0.62 (2H, m); TLC ($SiO_2$, 1:10 EtOAc:hexanes) $R_f$=0.20 (visualized with molybdophosphoric acid).

Under a nitrogen atmosphere and with stirring, to dry toluene (25 mL) was added small pieces of sodium (3.0 g, 130.4 mmol). The resulting suspension was heated to reflux and to it was added dropwise a mixture of the compound of formula VD (2.15 g, 12.86 mmol), toluene (25 mL), and isopropanol (10 mL). The resulting reaction mixture was stirred under reflux for 3 h. The mixture was cooled to a temperature of about 25° C., quenched with MeOH (10 mL) followed by water (5 mL), and the resulting mixture stirred for 15 min. The mixture was partitioned between 1M aqueous KOH (200 mL) and $Et_2O$ (200 mL). The organic portion was separated, dried ($MgSO_4$), and filtered. The filtrate was treated with 2M HCl in $Et_2O$ (20 mL) and the mixture filtered to provide a 1.12 g first portion of the compound of formula VE as a white crystalline solid. The filtrate was evaporated to dryness under reduced pressure, $Et_2O$ (100 mL) was added, and the mixture filtered to provide a 0.44 g second portion of the compound of formula VE; a total of 1.56 g was obtained (combined yield 63%).

The identity of the compound of formula VE, (exo, endo)-7-methylbicyclo[3.3.1]nonan-3-amine hydrochloride, was confirmed using $^1$H NMR.

Compound VE: $^1$H NMR: $\delta_H$ (400 MHz, $CDCl_3$): 8.20 (3H, bs), 3.43 (1H, m), 2.10 (2H, m), 1.85 (4H, m), 1.65-1.43 (5H, m), 1.00 (1H, d, J=12 Hz), 0.75 (3H, d, J=6 Hz), 0.65 (2H, dt, J=12 Hz, 2 Hz).

The compound of formula VE (1.56 g, 8.22 mmol), the compound of formula LB (3.20 g, 9.87 mmol), and $K_2CO_3$ (1.25 g, 9.04 mmol) were suspended in a mixture of EtOH (10 mL) and water (6 mL). The resulting reaction mixture was heated with stirring under reflux for 6 h, then allowed to cool to a temperature of about 25° C. over 18 h. The mixture was filtered to provide 2.00 g of the compound of formula VF as long white needles (yield 87%). It should be noted that in the above reaction scheme drawing for the compound of formula VF and the compounds prepared from it, for simplicity the "$CH_3$" notation for the 7-methyl substituent has been omitted.

The identity of the compound of formula VF, (exo, endo)-9-(7-methylbicyclo[3.3.1]nonan-3-yl)-9-azabicyclo[3.3.1]nonan-3-one, was confirmed using $^1$H NMR.

Compound VF: $^1$H NMR: $\delta_H$ (400 MHz, $CDCl_3$): 3.70 (2H, m), 3.05 (1H, m), 3.66 (2H, m), 3.04 (1H, m), 2.62 (2H, dd, J=16.7, 6.7 Hz), 2.22 (4H, m), 2.03-1.45 (13H, m), 1.26 (2H, dt, J=13.3 Hz, 3.3 Hz), 1.06 (1H, dt, J=13.3 Hz, 3.3 Hz), 0.86 (3H, d, J=6.7 Hz), 0.79 (2H, t, J=13.3 Hz).

The compound of formula VF (1.00 g, 3.63 mmol) and 1,2-phenylenediamine (0.471 g, 4.36 mmol) were dissolved in DME (2.5 mL). At a temperature of about 25° C., acetic acid (1 mL) was added and the resulting reaction mixture stirred for 24 h. Then, sodium triacetoxyborohydride (2.69 g, 12.71 mmol) was added and the resulting reaction mixture stirred for 6 h at a temperature of about 25° C. Thereafter, the mixture was quenched with water (5 mL) then partitioned between CHCl$_3$ (250 mL) and water (250 mL). The organic portion was separated, washed with 10% aqueous acetic acid (250 mL), dried (MgSO$_4$), and evaporated to dryness under reduced pressure to provide 1.20 g of the compound of formula VG, (exo, endo, endo)-N$^1$-(7-methylbicyclo[3.3.1]nonan-3-yl)-9-azabicyclo[3.3.1]nonan-3-yl)-benzene-1,2-diamine, as an orange gum which was used immediately in the following step.

Under a nitrogen atmosphere, to a solution of the compound of formula VG (1.10 g, 2.99 mmol) in toluene (10 mL) at a temperature of about 25° C. was added formic acid (0.34 mL, 8.97 mmol) followed by diethyl 2-oxomalonate (0.55 mL, 3.59 mmol). After the addition, the resulting reaction mixture was heated to a temperature of 110° C. and stirred for 1 h. Thereafter, the reaction mixture was cooled to a temperature of about 25° C. and EtOAc (100 mL) was added. That mixture was washed with 1M aqueous Na$_2$CO$_3$ solution (100 mL), dried (MgSO$_4$), and evaporated to dryness under reduced pressure to provide an orange gum. The orange gum was chromatographed with a silica gel column eluted with 900:100:20:1 hexanes:EtOAc:MeOH:ammonia to provide a yellow gum. The yellow gum was recrystallized from 1:1 Et$_2$O:hexanes (10 mL) to provide 400 mg of the compound of formula VH as a pale yellow solid. By mass spectrometry analysis, this product was found to contain about 10% of an impurity of [M+H]$^+$ equal to 451, which may have been the free carboxylic acid of the compound of formula VH. Therefore, the solid was dissolved in hot MeOH (25 mL), cooled to 0° C. with stirring over 1 h, and filtered to provide 313 mg of relatively pure compound of formula VH as a white solid (yield 22% for two steps).

The identity of the compound of formula VH, ethyl (exo, endo, endo)-4-(9-(7-methylbicyclo[3.3.1]nonan-3-yl)-9-azabicyclo[3.3.1]nonan-3-yl)-3-oxo-3,4-dihydroquinoxaline-2-carboxylate, was confirmed using $^1$H NMR and TLC.

Compound VH: $^1$H NMR: $\delta_H$ (400 MHz, CDCl$_3$): 7.88 (1H, d, J=8 Hz), 7.55 (2H, m), 7.30 (1H, t, J=8 Hz), 5.05 (1H, bs), 4.47 (2H, q, J=10 Hz), 3.43 (2H, m), 3.05 (1H, m), 2.65 (2H, m), 2.37 (1H, m), 2.13 (2H, m), 1.96-1.50 (12H, m), 1.38 (3H, t, J=10 Hz), 1.10 (4H, m), 0.95 (1H, m), 0.80 (5H, m); TLC (SiO$_2$, 900:100:20:1 hexanes:EtOAc:MeOH:ammonia) R$_f$=0.2 (ultraviolet detection, potassium iodoplatinate).

To a solution of the compound of formula VH (300 mg, 0.628 mmol) in THF (5 mL) at a temperature of about 25° C. was added a solution of KOH (106 mg) in water (1 mL). The resulting reaction mixture was stirred at a temperature of about 25° C. for 3 h. Thereafter, the reaction mixture was concentrated to dryness under reduced pressure to provide a residue. The residue was diluted with water (15 mL) and the resulting mixture was filtered, washed with water (5 mL), and dried at 50° C. for 48 h under reduced pressure to provide 300 mg of the potassium salt of Substituted-Quinoxaline-Type Bridged-Piperidine Compound 405 as a white solid (yield>99.5%).

The identity of Substituted-Quinoxaline-Type Bridged-Piperidine Compound 405, (exo, endo, endo)-4-(9-(7-methylbicyclo[3.3.1]nonan-3-yl)-9-azabicyclo[3.3.1]nonan-3-yl)-3-oxo-3,4-dihydroquinoxaline-2-carboxylic acid potassium salt, was confirmed using $^1$H NMR and LC/MS.

Substituted-Quinoxaline-Type Bridged-Piperidine Compound 405: $^1$H NMR: $\delta_H$ (400 MHz, DMSO-d$_6$): 7.70 (1H, d, J=10 Hz), 7.50 (2H, m), 7.28 (1H, m), 4.90 (1H, m), 3.46 (2H, m), 3.08 (1H, m), 2.38 (1H, m), 2.15 (2H, m), 2.00-1.80 (6H, m), 1.75-1.50 (5H, m), 1.16 (4H, m), 1.00 (1H, m), 0.90 (5H, m); LC/MS (100%): m/z=450 [M+H]$^+$ (Calc: 451).

5.10 Example 10

In vitro ORL-1 Receptor Binding Assays

ORL-1 Receptor Binding Assay Procedures:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 μg membrane protein in a final volume of 500 μL binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma). Harvesting was performed using a 96-well tissue harvester (Packard) followed by three filtration washes with 5004 ice-cold binding buffer. Filter plates were subsequently dried at 50° C. for 2-3 hours. Fifty μL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data:

Typically, the Substituted-Quinoxaline-Type Bridged-Piperidine Compounds will have a K$_i$ (nM) of about 300 or less for binding to ORL-1 receptors. In one embodiment, the Substituted-Quinoxaline-Type Bridged-Piperidine Compounds will have a K, (nM) of about 100 or less. In another embodiment, the Substituted-Quinoxaline-Type Bridged-Piperidine Compounds of the invention will have a K$_i$ (nM) of about 35 or less. In another embodiment, the Substituted-Quinoxaline-Type Bridged-Piperidine Compounds of the invention will have a K$_i$ (nM) of about 20 or less. In another embodiment, the Substituted-Quinoxaline-Type Bridged-Piperidine Compounds of the invention will have a K$_i$ (nM) of about 15 or less. In another embodiment, the Substituted-Quinoxaline-Type Bridged-Piperidine Compounds of the invention will have a K$_i$ (nM) of about 10 or less. In another embodiment, the Substituted-Quinoxaline-Type Bridged-Piperidine Compounds of the invention will have a K$_i$ (nM) of about 4 or less. In another embodiment, the Substituted-Quinoxaline-Type Bridged-Piperidine Compounds of the invention will have a $K_i$ (nM) of about 1 or less. In another embodiment, the Substituted-Quinoxaline-Type Bridged-Piperidine Compounds of the invention will have a $K_i$ (nM) of about 0.4 or less. In another embodiment, the Substituted-Quinoxaline-Type Bridged-Piperidine Compounds of the invention will have a $K_i$ (nM) of about 0.1 or less.

5.11 Example 11

In Vitro ORL-1 Receptor Functional Assays

ORL-1 Receptor [$^{35}$S]GTPγS Binding Assay Procedures:

Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/μL ORL-1 membrane protein, 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (BetaScint; Wallac) was added and plates were counted in Packard Top-Count for 1 min/well. Data are analyzed using the sigmoidal dose-response curve fitting functions in Graph-Pad PRISM v. 3.0, or an in-house function for non-linear, sigmoidal dose-response curve-fitting.

ORL-1 Receptor Functional Data:

ORL-1 GTP $EQ_{50}$ is the concentration of a compound providing 50% of the maximal response for the compound at an ORL-1 receptor. Substituted-Quinoxaline-Type Bridged-Piperidine Compounds typically will have an ORL-1 GTP $EC_{50}$ (nM) of about 5000 or less to stimulate ORL-1 receptor function. In one embodiment, the Substituted-Quinoxaline-Type Bridged-Piperidine Compounds of the invention will have an ORL-1 GTP $EC_{50}$ (nM) of about 1000 or less. In another embodiment, the Substituted-Quinoxaline-Type Bridged-Piperidine Compounds of the invention will have an ORL-1 GTP $EC_{50}$ (nM) of about 100 or less. In another embodiment, the Substituted-Quinoxaline-Type Bridged-Piperidine Compounds of the invention will have an ORL-1 GTP $EC_{50}$ (nM) of about 80 or less. In another embodiment, the Substituted-Quinoxaline-Type Bridged-Piperidine Compounds of the invention will have an ORL-1 GTP $EC_{50}$ (nM) of about 50 or less. In another embodiment, the Substituted-Quinoxaline-Type Bridged-Piperidine Compounds of the invention will have an ORL-1 GTP $EC_{50}$ (nM) of about 35 or less. In another embodiment, the Substituted-Quinoxaline-Type Bridged-Piperidine Compounds of the invention will have an ORL-1 GTP $EC_{50}$ (nM) of about 15 or less. In another embodiment, the Substituted-Quinoxaline-Type Bridged-Piperidine Compounds of the invention will have an ORL-1 GTP $EC_{50}$ (nM) of about 10 or less. In another embodiment, the Substituted-Quinoxaline-Type Bridged-Piperidine Compounds will have an ORL-1 GTP $EC_{50}$ (nM) of about 4 or less. In another embodiment, the Substituted-Quinoxaline-Type Bridged-Piperidine Compounds will have an ORL-1 GTP $EC_{50}$ (nM) of about 1 or less. In another embodiment, the Substituted-Quinoxaline-Type Bridged-Piperidine Compounds will have an ORL-1 GTP $EC_{50}$ (nM) of about 0.4 or less. In another embodiment, the Substituted-Quinoxaline-Type Bridged-Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. Typically, the Substituted-Quinoxaline-Type Bridged-Piperidine Compounds of the invention will have an ORL-1 GTP Emax (%) of greater than about 50%. In one embodiment, the Substituted-Quinoxaline-Type Bridged-Piperidine Compound Substituted-Quinoxaline-Type Bridged-Piperidine Compounds will have an ORL-1 GTP Emax (%) of greater than about 75%. In another embodiment, the Substituted-Quinoxaline-Type Bridged-Piperidine Compounds will have an ORL-1 GTP Emax (%) of greater than about 85%. In another embodiment, the Substituted-Quinoxaline-Type Bridged-Piperidine Compounds will have an ORL-1 GTP Emax (%) of greater than about 95%. In another embodiment, the Substituted-Quinoxaline-Type Bridged-Piperidine Compounds will have an ORL-1 GTP Emax (%) of about 100% or greater. In another embodiment, the Substituted-Quinoxaline-Type Bridged-Piperidine Compounds will have an ORL-1 GTP Emax (%) of about 110% or greater. Typically, a Substituted-Quinoxaline-Type Bridged-Piperidine Compound of the invention acting as a partial agonist will have an ORL-1 GTP Emax (%) of less than about 10%. In one embodiment, partial agonist Substituted-Quinoxaline-Type Bridged-Piperidine Compounds will have an ORL-1 GTP Emax (%) of less than about 20%. In another embodiment, partial agonist Substituted-Quinoxaline-Type Bridged-Piperidine Compounds will have an ORL-1 GTP Emax (%) of less than about 30%. In another embodiment, partial agonist Substituted-Quinoxaline-Type Bridged-Piperidine Compounds will have an ORL-1 GTP Emax (%) of less than about 40%. In another embodiment, partial agonist Substituted-Quinoxaline-Type Bridged-Piperidine Compounds will have an ORL-1 GTP Emax (%) of less than about 50%.

5.12 Example 12

In vitro Mu-opioid Receptor Binding Assays

μ-Opioid Receptor Assay Procedures:

Radioligand dose-displacement binding assays for μ-opioid receptors used 0.2 nM[$^3$H]-diprenorphine (NEN, Boston, Mass.), with 5-20 mg membrane protein/well in a final volume of 500 μL binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at about 25° C. Binding reactions were terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 μL of ice-cold binding buffer. Filter plates were subsequently dried at 50° C. for 2-3 hours. BetaScint scintillation cocktail (Wallac, Turku, Finland) was added (50 µL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

µ-Opioid Receptor Binding Data:

Typically, the Substituted-Quinoxaline-Type Bridged-Piperidine Compounds will have a $K_i$ (nM) of about 3000 or less for binding to g-opioid receptors. In one embodiment, the Substituted-Quinoxaline-Type Bridged-Piperidine Compounds will have a $K_i$ (nM) of about 1000 or less. In another embodiment, the Substituted-Quinoxaline-Type Bridged-Piperidine Compounds of the invention will have a $K_i$ (nM) of about 650 or less. In another embodiment, the Substituted-Quinoxaline-Type Bridged-Piperidine Compounds of the invention will have a $K_i$ (nM) of about 525 or less. In another embodiment, the Substituted-Quinoxaline-Type Bridged-Piperidine Compounds of the invention will have a $K_i$ (nM) of about 250 or less. In another embodiment, the Substituted-Quinoxaline-Type Bridged-Piperidine Compounds of the invention will have a $K_i$ (nM) of about 100 or less. In another embodiment, the Substituted-Quinoxaline-Type Bridged-Piperidine Compounds of the invention will have a $K_i$ (nM) of about 10 or less. In another embodiment, the Substituted-Quinoxaline-Type Bridged-Piperidine Compounds of the invention will have a $K_i$ (nM) of about 1 or less. In another embodiment, the Substituted-Quinoxaline-Type Bridged-Piperidine Compounds of the invention will have a $K_i$ (nM) of about 0.1 or less.

5.13 Example 13

In vitro Mu-opioid Receptor Functional Assays

µ-Opioid Receptor Functional Assay Procedures:

[$^{35}$S]GTPγS functional assays were conducted using freshly thawed g-receptor membranes. Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 µL/well) was transferred to 96-shallow well polypropylene plates containing 10 µL of 20× concentrated stock solutions of the agonist DAMGO ([D-Ala2, N-methyl-Phe4 Gly-ol5]-enkephalin) prepared in DMSO. Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 µL of ice-cold wash buffer (10 mM NaH$_2$PO$_4$, 10 mM Na$_2$HPO$_4$, pH 7.4). Filter plates were subsequently dried at 50° C. for 2-3 hr. BetaScint scintillation cocktail (Wallac, Turku, Finland) was added (50 µL/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

µ-Opioid Receptor Functional Data:

µ GTP $EC_{50}$ is the concentration of a compound providing 50% of the maximal response for the compound at a µ-opioid receptor. Substituted-Quinoxaline-Type Bridged-Piperidine Compounds typically will have a µ GTP $EC_{50}$ (nM) of about 5000 or less to stimulate µ-opioid receptor function. In one embodiment, the Substituted-Quinoxaline-Type Bridged-Piperidine Compounds of the invention will have a µ GTP $EC_{50}$ (nM) of about 4100 or less. In one embodiment, the Substituted-Quinoxaline-Type Bridged-Piperidine Compounds of the invention will have a µ GTP $EC_{50}$ (nM) of about 3100 or less. In another embodiment, the Substituted-Quinoxaline-Type Bridged-Piperidine Compounds of the invention will have a µ GTP $EC_{50}$ (nM) of about 2000 or less. In another embodiment, the Substituted-Quinoxaline-Type Bridged-Piperidine Compounds of the invention will have a µ GTP $EC_{50}$ (nM) of about 1000 or less. In another embodiment, the Substituted-Quinoxaline-Type Bridged-Piperidine Compounds of the invention will have a µ GTP $EC_{50}$ (nM) of about 100 or less. In another embodiment, the Substituted-Quinoxaline-Type Bridged-Piperidine Compounds of the invention will have a µ GTP $EC_{50}$ (nM) of about 10 or less. In another embodiment, the Substituted-Quinoxaline-Type Bridged-Piperidine Compounds will have a µ GTP $EC_{50}$ (nM) of about 1 or less. In another embodiment, the Substituted-Quinoxaline-Type Bridged-Piperidine Compounds will have a µ GTP $EC_{50}$ (nM) of about 0.4 or less. In another embodiment, the Substituted-Quinoxaline-Type Bridged-Piperidine Compounds will have a µ GTP $EC_{50}$ (nM) of about 0.1 or less.

µ GTP Emax (%) is the maximal effect elicited by a compound relative to the effect elicited by DAMGO, a standard µ agonist. Typically, the Substituted-Quinoxaline-Type Bridged-Piperidine Compounds of the invention will have a µ GTP Emax (%) of greater than about 10%. In one embodiment, the Substituted-Quinoxaline-Type Bridged-Piperidine Compounds will have a µ GTP Emax (%) of greater than about 20%. In another embodiment, the Substituted-Quinoxaline-Type Bridged-Piperidine Compounds will have a µ GTP Emax (%) of greater than about 50%. In another embodiment, the Substituted-Quinoxaline-Type Bridged-Piperidine Compounds will have a µ GTP Emax (%) of greater than about 65%. In another embodiment, the Substituted-Quinoxaline-Type Bridged-Piperidine Compounds will have a µ GTP Emax (%) of greater than about 75%. In another embodiment, the Substituted-Quinoxaline-Type Bridged-Piperidine Compounds will have a µ GTP Emax (%) of greater than about 88%. In another embodiment, the Substituted-Quinoxaline-Type Bridged-Piperidine Compounds will have a µ GTP Emax (%) of about 100% or greater.

5.14 Example 14

In vitro Kappa-opioid Receptor Binding Assays

κ-Opioid Receptor Binding Assay Procedures:

Membranes from recombinant HEK-293 cells expressing the human kappa opioid receptor (kappa) (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80° C.

Radioligand dose displacement assays used 0.4-0.8 nM [$^3$H]-U69,593 (NEN; 40 Ci/mmole) with 10-20 µg membrane protein (recombinant kappa opioid receptor expressed in HEK 293 cells; in-house prep) in a final volume of 200 µL binding buffer (5% DMSO, 50 mM Trizma base, pH 7.4). Non-specific binding was determined in the presence of 10

µM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 2004 ice-cold binding buffer. Filter plates were subsequently dried at 50° C. for 1-2 hours. Fifty µL/well scintillation cocktail (MicroScint20, Packard) was added and plates were counted in a Packard Top-Count for 1 min/well.

κ-Opioid Receptor Binding Data:

Typically, the Substituted-Quinoxaline-Type Bridged-Piperidine Compounds will have a Ki (nM) of about 20,000 or less for κ receptors. In one embodiment, the Substituted-Quinoxaline-Type Bridged-Piperidine Compounds will have a Ki (nM) of about 10,000 or less. In another embodiment, the Substituted-Quinoxaline-Type Bridged-Piperidine Compounds will have a Ki (nM) of about 5000 or less. In another embodiment, the Substituted-Quinoxaline-Type Bridged-Piperidine Compounds will have a Ki (nM) of about 1000 or less. In another embodiment, the Substituted-Quinoxaline-Type Bridged-Piperidine Compounds will have a Ki (nM) of about 500 or less. In another embodiment, the Substituted-Quinoxaline-Type Bridged-Piperidine Compounds will have a Ki (nM) of about 300 or less. In another embodiment, the Substituted-Quinoxaline-Type Bridged-Piperidine Compounds will have a Ki (nM) of about 100 or less. In another embodiment, the Substituted-Quinoxaline-Type Bridged-Piperidine Compounds will have a Ki (nM) of about 50 or less. In another embodiment, the Substituted-Quinoxaline-Type Bridged-Piperidine Compounds will have a Ki (nM) of about 20 or less. In another embodiment, the Substituted-Quinoxaline-Type Bridged-Piperidine Compounds will have a Ki (nM) of about 15 or less. In another embodiment, the Substituted-Quinoxaline-Type Bridged-Piperidine Compounds will have a Ki (nM) of about 10 or less.

5.15 Example 15

In vitro Kappa-opioid Receptor Functional Assays

κ-Opioid Receptor Functional Assay Procedures:

Functional [$^{35}$S]GTPγS binding assays were conducted as follows. Kappa opioid receptor membrane solution was prepared by sequentially adding final concentrations of 0.026 µg/µL kappa membrane protein (in-house), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 2-3 hours. Fifty µL/well scintillation cocktail (MicroScint20, Packard) was added and plates were counted in a Packard Top-Count for 1 min/well.

κ-Opioid Receptor Functional Data:

κ GTP $EC_{50}$ is the concentration of a compound providing 50% of the maximal response for the compound at a κ receptor. Substituted-Quinoxaline-Type Bridged-Piperidine Compounds typically will have a κ GTP $EC_{50}$ (nM) of about 20,000 or less to stimulate κ opioid receptor function. In one embodiment, the Substituted-Quinoxaline-Type Bridged-Piperidine Compounds will have a κ GTP $EC_{50}$ (nM) of about 10,000 or less. In another embodiment, the Substituted-Quinoxaline-Type Bridged-Piperidine Compounds will have a κ GTP $EC_{50}$ (nM) of about 5000 or less. In another embodiment, the Substituted-Quinoxaline-Type Bridged-Piperidine Compounds will have a κ GTP $EC_{50}$ (nM) of about 2000 or less. In another embodiment, the Substituted-Quinoxaline-Type Bridged-Piperidine Compounds will have a κ GTP $EC_{50}$ (nM) of about 1500 or less. In another embodiment, the Substituted-Quinoxaline-Type Bridged-Piperidine Compounds will have a κ GTP $EC_{50}$ (nM) of about 800 or less. In another embodiment, the Substituted-Quinoxaline-Type Bridged-Piperidine Compounds will have a κ GTP $EC_{50}$ (nM) of about 500 or less. In another embodiment, the Substituted-Quinoxaline-Type Bridged-Piperidine Compounds will have a κ GTP $EC_{50}$ (nM) of about 300 or less. In another embodiment, the Substituted-Quinoxaline-Type Bridged-Piperidine Compounds will have a κ GTP $EC_{50}$ (nM) of about 100 or less. In another embodiment, the Substituted-Quinoxaline-Type Bridged-Piperidine Compounds will have a κ GTP $EC_{50}$ (nM) of about 50 or less. In another embodiment, the Substituted-Quinoxaline-Type Bridged-Piperidine Compounds will have a κ GTP $EC_{50}$ (nM) of about 25 or less. In another embodiment, the Substituted-Quinoxaline-Type Bridged-Piperidine Compounds will have a κ GTP $EC_{50}$ (nM) of about 10 or less.

κ GTP Emax (%) is the maximal effect elicited by a compound relative to the effect elicited by U69,593. Typically, the Substituted-Quinoxaline-Type Bridged-Piperidine Compounds of the invention will have a κ GTP Emax (%) of greater than about 10%. In one embodiment, the Substituted-Quinoxaline-Type Bridged-Piperidine Compounds will have a κ GTP Emax (%) of greater than about 15%. In another embodiment, the Substituted-Quinoxaline-Type Bridged-Piperidine Compounds will have a κ GTP Emax (%) of greater than about 30%. In another embodiment, the Substituted-Quinoxaline-Type Bridged-Piperidine Compounds will have a κ GTP Emax (%) of greater than about 40%. In another embodiment, the Substituted-Quinoxaline-Type Bridged-Piperidine Compounds will have a κ GTP Emax (%) of greater than about 45%. In another embodiment, the Substituted-Quinoxaline-Type Bridged-Piperidine Compounds will have a κ GTP Emax (%) of greater than about 75%. In another embodiment, the Substituted-Quinoxaline-Type Bridged-Piperidine Compounds will have a κ GTP Emax (%) of greater than about 90%. In another embodiment, the Substituted-Quinoxaline-Type Bridged-Piperidine Compounds will have a κ GTP Emax (%) of about 100% or greater.

5.16 Example 16

In vitro Delta-opioid Receptor Binding Assays

δ-Opioid Receptor Binding Assay Procedures:

Radioligand dose-displacement assays used 0.2 nM [$^3$H]-Naltrindole (NEN; 33.0 Ci/mmole) with 10-20 µg membrane protein (recombinant delta opioid receptor expressed in CHO-K1 cells; Perkin Elmer) in a final volume of 500 µL binding buffer (5 mM $MgCl_2$, 5% DMSO, 50 mM Trizma base, pH 7.4). Non-specific binding was determined in the presence of 25 µM unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 500 μL ice-cold binding buffer. Filter plates were subsequently dried at 50° C. for 1-2 hours. Fifty μL/well scintillation cocktail (MicroScint20, Packard) was added and plates were counted in a Packard Top-Count for 1 min/well.

δ-Opioid Receptor Binding Data:

Typically, the Substituted-Quinoxaline-Type Bridged-Piperidine Compounds will have a Ki (nM) of about 20,000 or less for S receptors. In one embodiment, the Substituted-Quinoxaline-Type Bridged-Piperidine Compounds will have a Ki (nM) of about 10,000 or less. In another embodiment, the Substituted-Quinoxaline-Type Bridged-Piperidine Compounds will have a Ki (nM) of about 7500 or less. In another embodiment, the Substituted-Quinoxaline-Type Bridged-Piperidine Compounds will have a Ki (nM) of about 6500 or less. In another embodiment, the Substituted-Quinoxaline-Type Bridged-Piperidine Compounds will have a Ki (nM) of about 5000 or less. In another embodiment, the Substituted-Quinoxaline-Type Bridged-Piperidine Compounds will have a Ki (nM) of about 3000 or less. In another embodiment, the Substituted-Quinoxaline-Type Bridged-Piperidine Compounds will have a Ki (nM) of about 2500 or less. In another embodiment, the Substituted-Quinoxaline-Type Bridged-Piperidine Compounds will have a Ki (nM) of about 1000 or less. In another embodiment, the Substituted-Quinoxaline-Type Bridged-Piperidine Compounds will have a Ki (nM) of about 500 or less. In another embodiment, the Substituted-Quinoxaline-Type Bridged-Piperidine Compounds will have a Ki (nM) of about 350 or less. In another embodiment, the Substituted-Quinoxaline-Type Bridged-Piperidine Compounds will have a Ki (nM) of about 250 or less. In another embodiment, the Substituted-Quinoxaline-Type Bridged-Piperidine Compounds will have a Ki (nM) of about 100 or less. In another embodiment, the Substituted-Quinoxaline-Type Bridged-Piperidine Compounds will have a Ki (nM) of about 10 or less.

5.17 Example 17

In vitro Delta-opioid Receptor Functional Assays

δ-Opioid Receptor Functional Assay Procedures:

Functional [$^{35}$S]GTPγS binding assays were conducted as follows. Delta opioid receptor membrane solution was prepared by sequentially adding final concentrations of 0.026 μg/μL delta membrane protein (Perkin Elmer), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μL/well) was transferred to 96-shallow well polypropylene plates containing 10 μL, of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 2041 ice-cold binding buffer (10 mM NaH$_2$PO$_4$, 10 mM Na$_2$HPO$_4$, pH 7.4). Filter plates were subsequently dried at 50° C. for 1-2 hours. Fifty μL/well scintillation cocktail (MicroScint20, Packard) was added and plates were counted in a Packard Top-count for 1 min/well.

δ-Opioid Receptor Functional Data:

δ GTP EC$_{50}$ is the concentration of a compound providing 50% of the maximal response for the compound at a S receptor. Substituted-Quinoxaline-Type Bridged-Piperidine Compounds typically will have a δ GTP EC$_{50}$ (nM) of about 20,000 or less to stimulate S opioid receptor function. In one embodiment, the Substituted-Quinoxaline-Type Bridged-Piperidine Compounds will have a δ GTP EC$_{50}$ (nM) of about 10,000 or less. In another embodiment, the Substituted-Quinoxaline-Type Bridged-Piperidine Compounds will have a δ GTP EC$_{50}$ (nM) of about 100 or less. In another embodiment, the Substituted-Quinoxaline-Type Bridged-Piperidine Compounds will have a δ GTP EC$_{50}$ (nM) of about 1000 or less. In another embodiment, the Substituted-Quinoxaline-Type Bridged-Piperidine Compounds will have a δ GTP EC$_{50}$ (nM) of about 90 or less. In another embodiment, the Substituted-Quinoxaline-Type Bridged-Piperidine Compounds will have a δ GTP EC$_{50}$ (nM) of about 50 or less. In another embodiment, the Substituted-Quinoxaline-Type Bridged-Piperidine Compounds will have a δ GTP EC$_{50}$ (nM) of about 25 or less. In another embodiment, the Substituted-Quinoxaline-Type Bridged-Piperidine Compounds will have a δ GTP EC$_{50}$ (nM) of about 10 or less.

δ GTP Emax (%) is the maximal effect elicited by a compound relative to the effect elicited by met-enkephalin. Typically, the Substituted-Quinoxaline-Type Bridged-Piperidine Compounds of the invention will have a δ GTP Emax (%) of greater than about 10%. In one embodiment, the Substituted-Quinoxaline-Type Bridged-Piperidine Compounds will have a δ GTP Emax (%) of greater than about 30%. In another embodiment, the Substituted-Quinoxaline-Type Bridged-Piperidine Compounds will have a δ GTP Emax (%) of greater than about 50%. In another embodiment, the Substituted-Quinoxaline-Type Bridged-Piperidine Compounds will have a δ GTP Emax (%) of greater than about 75%. In another embodiment, the Substituted-Quinoxaline-Type Bridged-Piperidine Compounds will have a δ GTP Emax (%) of greater than about 90%. In another embodiment, the Substituted-Quinoxaline-Type Bridged-Piperidine Compounds will have a δ GTP Emax (%) of about 100% or greater. In another embodiment, the Substituted-Quinoxaline-Type Bridged-Piperidine Compounds will have a δ GTP Emax (%) of about 110% or greater.

5.18 Example 18

Efficacy of Receptor Binding and Activity Response

The following Tables provide results on the efficacy of binding and activity response of several Substituted-Quinoxaline-Type Bridged-Piperidine Compounds to the ORL-1 receptor and, for certain Substituted-Quinoxaline-Type Bridged-Piperidine Compounds, the mu-opioid receptor, the kappa-opioid receptor, and/or the delta-opioid receptor.

In Table 1, binding efficacy to the ORL-1 receptor was determined by the procedure in Example 10. Binding efficacy to the mu-opioid receptor was determined by the procedure in Example 12. Binding efficacy to the kappa-opioid receptor was determined by the procedure in Example 14. Binding efficacy to the delta-opioid receptor was determined by the procedure in Example 16.

In Table 2, activity response to the ORL-1 receptor was determined by the procedure in Example 11. Activity response to the mu-opioid receptor was determined by the procedure in Example 13. Activity response to the kappa-opioid receptor was determined by the procedure in Example 15. Activity response to the delta-opioid receptor can be determined by the procedure in Example 17.

TABLE 1

Efficacy of Receptor Binding of Substituted-Quinoxaline-Type
Bridged-Piperidine Compounds $K_i$ [Average ± Std Deviation] (nM)

| Ref No. | Opioid Receptor | | | |
|---|---|---|---|---|
| | ORL-1 | Mu | Kappa | Delta |
| 356 | 43.1 ± 3.4 | 1436 ± 215 | 76 ± 21 | 18180 |
| 358 | 9.0 ± 1.1 | 1600 ± 55 | 640 ± 126 | 8900 ± 2390 |
| 360 | 202.8 ± 7.1 | 3825 ± 576 | 2691 ± 189 | >20,000 |
| 361 | 5.7 ± 0.4 | 4450 ± 1224 | 6143 ± 1617 | >20,000 |
| 362 | 2.4 ± 0.2 | 1631 ± 77 | 2280 ± 213 | 4763 ± 509 |
| 369 | 178 ± 17 | 4032 ± 1010 | 5345 ± 1725 | >20,000 |
| 405 | 1.1 ± 0.1 | 61.6 ± 8.7 | 75.4 ± 7.8 | 691 ± 57 |

TABLE 2

Activity Response of Substituted-Quinoxaline-Type
Bridged-Piperidine Compounds

GTPγS ($EC_{50}$: nM, Emax: %) [mean ± SEM]

| Ref No. | Opioid Receptor | | | | | |
|---|---|---|---|---|---|---|
| | ORL-1 | | Mu | | Kappa | |
| | $EC_{50}$ | $E_{max}$ | $EC_{50}$ | $E_{max}$ | $EC_{50}$ | $E_{max}$ |
| 356 | 686 ± 41 | 93.3 ± 8 | | | >20,000 | 3.3 ± 1.2 |
| 358 | 62.6 ± 14.1 | 101.3 ± 5.7 | 17,800 ± 14,600 | 9.7 ± 0.9 | 1960 ± 806 | 11.7 ± 2.3 |
| 360 | 1667.1 ± 18.4 | 57.3 ± 4.1 | | | | |
| 361 | 57.2 ± 3.1 | 58.7 ± 2.4 | >20,000 | 0 | >20,000 | 9.7 ± 5.6 |
| 362 | 4.03 ± 0.86 | 47.8 ± 1.3 | >20,000 | 0 | >20,000 | 3.0 ± 0.6 |
| 369 | 545 ± 85 | 37.7 ± 0.7 | | | | |
| 405 | 0.55 ± 0.1 | 47.5 ± 3.5 | >20,000 | 0 | >20,000 | 0 |

5.19 Example 19

In Vivo Assays for Prevention or Treatment of Pain

Test Animals:

Each experiment used rats weighing between 200-260 g at the start of the experiment. The rats were group-housed and had free access to food and water at all times, except prior to oral administration of a Substituted-Quinoxaline-Type Bridged-Piperidine Compound when food was removed for 16 hours before dosing. A control group acted as a comparison to rats treated with a Substituted-Quinoxaline-Type Bridged-Piperidine Compound. The control group was administered the carrier for the Substituted-Quinoxaline-Type Bridged-Piperidine Compound. The volume of carrier administered to the control group was the same as the volume of carrier and Substituted-Quinoxaline-Type Bridged-Piperidine Compound administered to the test group.

Acute Pain:

To assess the actions of a Substituted-Quinoxaline-Type Bridged-Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Substituted-Quinoxaline-Type Bridged-Piperidine Compound. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Inflammatory Pain:

To assess the actions of a Substituted-Quinoxaline-Type Bridged-Piperidine Compound for the treatment or prevention of inflammatory pain, the Freund's complete adjuvant ("FCA") model of inflammatory pain was used. FCA-induced inflammation of the rat hind paw is associated with the development of persistent inflammatory mechanical and thermal hyperalgesia and provides reliable prediction of the antihyperalgesic action of clinically useful analgesic drugs (L. Bartho et al., "Involvement of Substituted-Quinoxaline-Type Bridged-Piperidine Compound Inflammation," *Naunyn-Schmiedeberg's Archives of Pharmacol.* 342:666-670 (1990)). The left hind paw of each animal was administered a 50 µL intraplantar injection of 50% FCA. 24 hour post injection, the animal was assessed for response to noxious mechanical stimuli by determining the PWT, or to noxious thermal stimuli by determining the PWL, as described below. Rats were then administered a single injection of 0.1, 0.3, 1, 3, 10 or 30 mg/kg of either a Substituted-Quinoxaline-Type Bridged-Piperidine Compound; 30 mg/kg of a control selected from Celebrex, indomethacin or naproxen; or carrier. Responses to noxious mechanical stimuli were then determined 1, 3, 5 and 24 hours post administration. Percentage reversal of hyperalgesia for each animal was defined as:

$$\% \text{ Reversal} = \frac{\left[\begin{array}{c}(\text{post administration } PWT/PWL) - \\ (\text{pre-administration } PWT/PWL)\end{array}\right]}{[(\text{baseline } PWT) - (\text{pre-administration } PWT)]} \times 100$$

Assessments of the actions of the Substituted-Quinoxaline-Type Bridged-Piperidine Compounds that were tested revealed these compounds were efficacious, e.g., Substituted-Quinoxaline-Type Bridged-Piperidine Compounds significantly reduced FCA-induced thermal hyperalgesia, with $ED_{50}$ values of from about 0.1 mg/kg to about 20 mg/kg and maximum % reversal values of from about 20% to about 100%. For example, for the Substituted Quinoxaline-Type Bridged-Piperidine Compound 362, the $ED_{50}$ value for reversal of thermal hyperalgesia was 0.8 mg/kg at 1 hour after administration, 1.5 mg/kg at 3 hours after administration, and 3.0 mg/kg at 5 hours after administration of Substituted Quinoxaline-Type Bridged-Piperidine Compound 362. Additionally, the % reversal of thermal hyperalgesia after administration of a 3 mg/kg dose was 86% at 1 hour after administration, 51% at 3 hours after administration, and 27% at 5 hours after administration of Substituted Quinoxaline-Type Bridged-Piperidine Compound 362. And, for Substituted Quinoxaline-Type Bridged-Piperidine Compound 361, upon administration of a 5 mg/kg dose, the % reversal of thermal hyperalgesia was 36% reversal at 1 hour after administration, 90% reversal at 3 hours after administration, and 70% reversal at 5 hours after administration of Substituted Quinoxaline-Type Bridged-Piperidine Compound 361. And, for Substituted Quinoxaline-Type Bridged-Piperidine Compound 358, upon administration of 5 mg/kg dose, the % reversal of thermal hyperalgesia was 34% reversal at 1 hour after administration, 46% reversal at 3 hours after administration, and 79% reversal at 5 hours after administration of Substituted Quinoxaline-Type Bridged-Piperidine Compound 358.

Substituted Quinoxaline-Type Bridged-Piperidine Compounds 358, 361, and 362 also have surprisingly and desirably reduced abnormal behavioral side effects, such as reduced sedation, hyperactivity and/or hypoactivity. Additionally and surprisingly, Substituted Quinoxaline-Type Bridged-Piperidine Compound 362 has reduced cardiovascular side effects. These side effects were determined using known methods: an in vitro hERG (human ether a-go-go gene) assay as disclosed in Z. Zhou et al., "Properties of HERG Channels Stably Expressed in HEK 293 Cells Studied at Physiological Temperature," *Biophysical J.* 74:230-241 (1998); and APD (action potential duration) in guinea pig purkinje fibers as disclosed in J. A. Hey, "The Guinea Pig Model for Assessing Cardiotoxic Proclivities of Second Generation Antihistamines," *Arzneimittelforschung* 46(8):834-837 (1996).

Neuropathic Pain:

To assess the actions of a Substituted-Quinoxaline-Type Bridged-Piperidine Compound for the treatment or prevention of neuropathic pain, either the Seltzer model or the Chung model can be used.

In the Seltzer model, the partial sciatic nerve ligation model of neuropathic pain was used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve was performed under isoflurane/$O_2$ inhalation anesthesia. Following induction of anesthesia, the left thigh of the rat was shaved and the sciatic nerve exposed at high thigh level through a small incision and was carefully cleared of surrounding connective tissues at a site near the trocanther just distal to the point at which the posterior biceps semitendinosus nerve branches off of the common sciatic nerve. A 7-0 silk suture was inserted into the nerve with a ⅜ curved, reversed-cutting mini-needle and tightly ligated so that the dorsal ⅓ to ½ of the nerve thickness was held within the ligature. The wound was closed with a single muscle suture (4-0 nylon (Vicryl)) and vetbond tissue glue. Following surgery, the wound area was dusted with antibiotic powder. Sham-treated rats underwent an identical surgical procedure except that the sciatic nerve was not manipulated. Following surgery, animals were weighed and placed on a warm pad until they recovered from anesthesia. Animals were then returned to their home cages until behavioral testing began. The animals were assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia was defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Assessments of the actions of the Substituted-Quinoxaline-Type Bridged-Piperidine Compounds that were tested revealed that these compounds were efficacious, e.g. Substituted-Quinoxaline-Type Bridged-Piperidine Compounds significantly reduced nerve injury-induced mechanical hyperalgesia, with $ED_{50}$ values from about 0.3 mg/kg to about 20 mg/kg and maximum % reversal values of from about 20% to about 70%. For example, for the Substituted-Quinoxaline-Type Bridged-Piperidine 362, the % reversal of mechanical hyperalgesia after administration of 3 mg/kg was 60% at 1 and 3 hours after administration, 50% at 5 hours, and 40% at 7 hours. And, for Substituted-Quinoxaline-Type Bridged-Piperidine Compound 405, upon administration of a 3 mg/kg dose, the % reversal of mechanical hyperalgesia was 70% at 1, 3 and 5 hours after administration of the Substituted-Quinoxaline-Type Bridged-Piperidine Compound 405.

The Chung model may also be used to assess neuropathic hyperalgesia. In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Substituted-Quinoxaline-Type Bridged-Piperidine Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay was used to assess mechanical hyperalgesia. For this assay, hind paw withdrawal thresholds (PWT) to a noxious mechanical stimulus were determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that could be applied to the hind paw was set at 250 g and the end point is taken was complete withdrawal of the paw. PWT was determined once for each rat at each time point and either only the affected (ipsilateral) paw was tested, or both the ipsilateral and contralateral (non-injured) paw were tested.

Response to Thermal Stimuli as an Assessment of Thermal Hyperalgesia:

The plantar test can be used to assess thermal hyperalgesia. For this test, hind paw withdrawal latencies (PWL) to a noxious thermal stimulus were determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time was set at 32 seconds to avoid tissue damage and any directed paw withdrawal from the heat source was taken as the end point. Three latencies were determined at each time point and averaged. Either only the affected (ipsilateral) paw was tested, or both the ipsilateral and contralateral (non-injured) paw were tested.

Assessment of Tactile Allodynia:

To assess tactile allodynia, rats are placed in clear, Plexiglas compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference for all purposes.

What is claimed:

1. A compound having the formula:

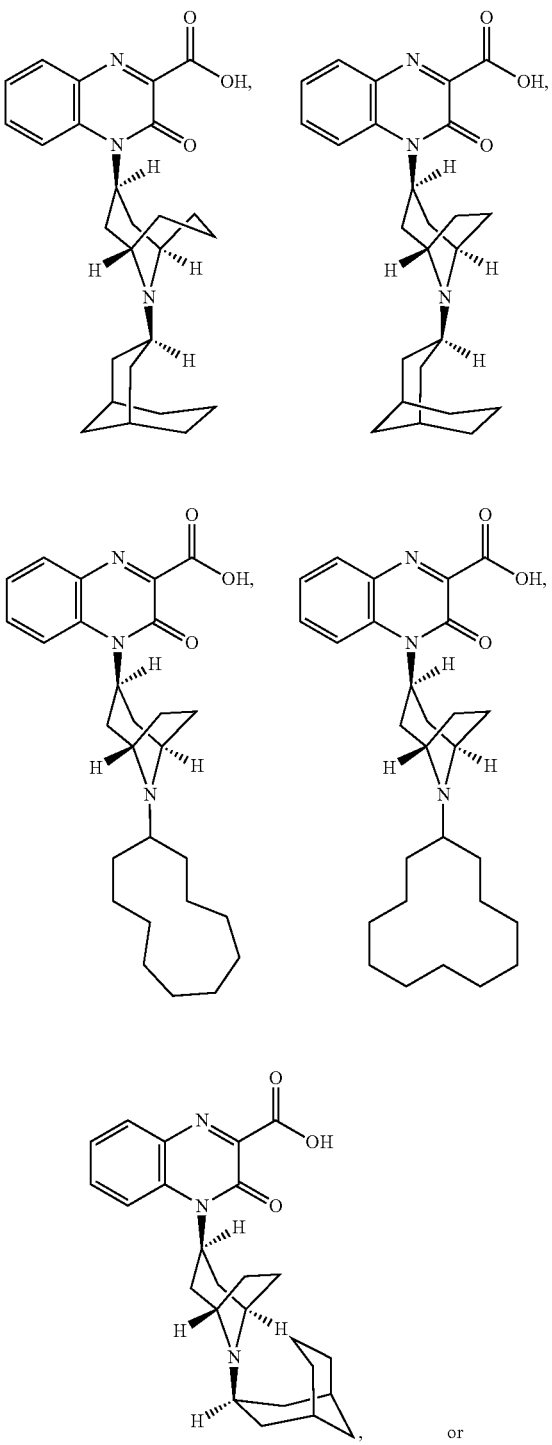

or

-continued

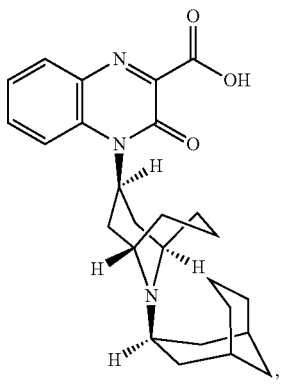

or a pharmaceutically acceptable salt thereof.

2. The compound of claim 1 having the formula:

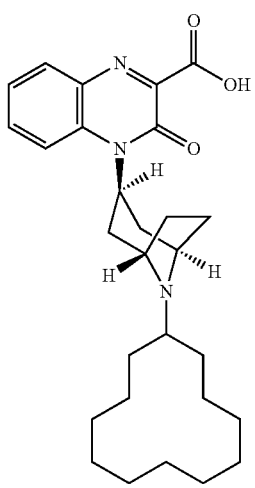 [SMILES: O=C(O)c1nc2ccccc2n([C@H]2C[C@H]3CC[C@@H](C2)N3C2CCCCCCCCCCC2)c1=O]

or a pharmaceutically acceptable salt thereof.

3. The compound of claim 1 having the formula:

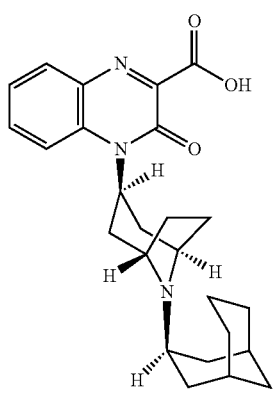

or a pharmaceutically acceptable salt thereof.

4. The compound of claim 1 having the formula:

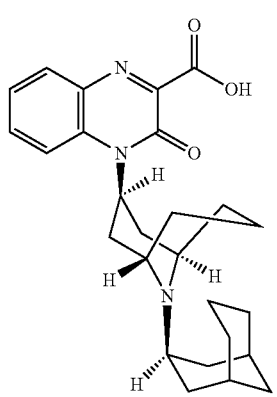

or a pharmaceutically acceptable salt thereof.

5. The compound of claim 1 having the formula:

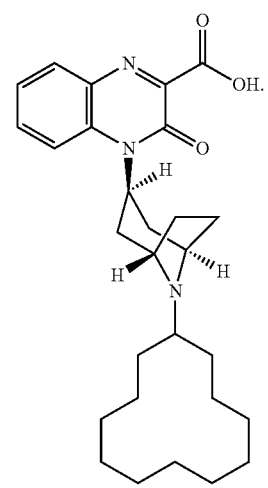 [SMILES: O=C(O)c1nc2ccccc2n([C@H]2C[C@H]3CC[C@@H](C2)N3C2CCCCCCCCCCC2)c1=O]

6. The compound of claim 1 having the formula:

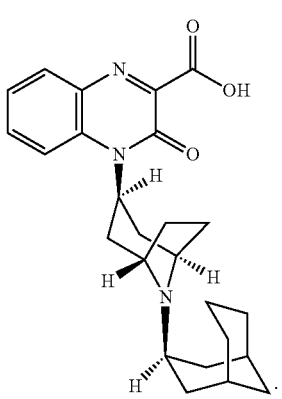

7. The compound of claim 1 having the formula:

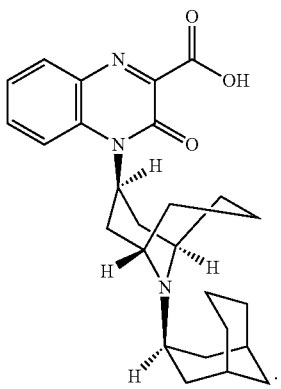

8. The compound of claim 1 having the formula:

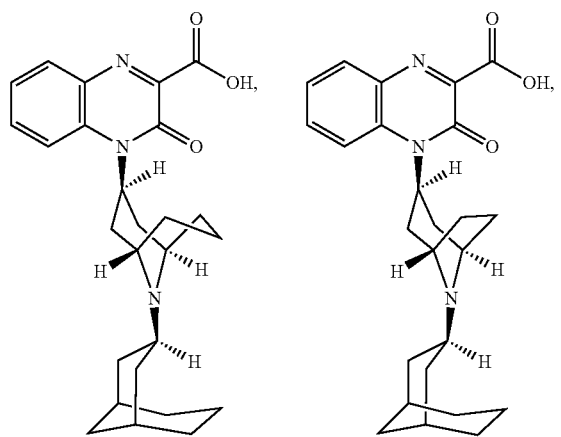

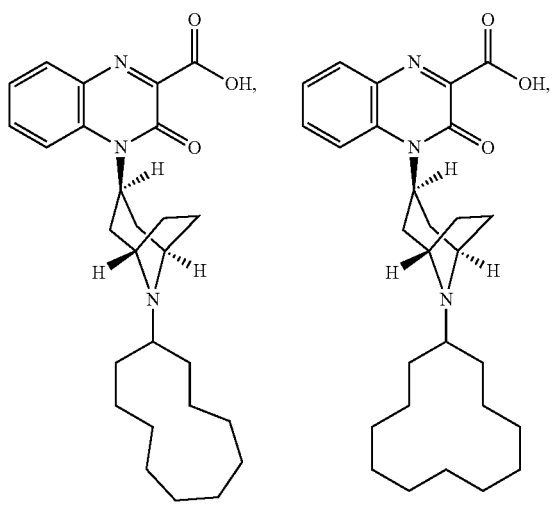

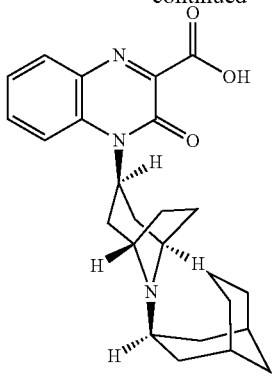, or

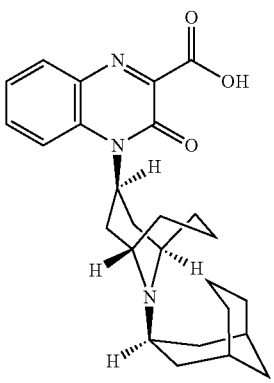,

9. A pharmaceutically acceptable salt of the compound of claim 1, wherein the pharmaceutically acceptable salt is a p-toluenesulfonic acid salt, a sulfate salt, a phosphoric acid salt, or a hydrochloride salt.

10. A pharmaceutically acceptable salt of the compound of claim 2, wherein the pharmaceutically acceptable salt is a p-toluenesulfonic acid salt, a sulfate salt, a phosphoric acid salt, or a hydrochloride salt.

11. A pharmaceutically acceptable salt of the compound of claim 3, wherein the pharmaceutically acceptable salt is a p-toluenesulfonic acid salt, a sulfate salt, a phosphoric acid salt, or a hydrochloride salt.

12. A pharmaceutically acceptable salt of the compound of claim 4, wherein the pharmaceutically acceptable salt is a p-toluenesulfonic acid salt, a sulfate salt, a phosphoric acid salt, or a hydrochloride salt.

13. A pharmaceutical composition comprising an effective amount of the compound or a pharmaceutically acceptable salt of the compound of claim 1 and a pharmaceutically acceptable carrier or excipient.

14. A pharmaceutical composition comprising an effective amount of the compound or a pharmaceutically acceptable salt of the compound of claim 2 and a pharmaceutically acceptable carrier or excipient.

15. A pharmaceutical composition comprising an effective amount of the compound or a pharmaceutically acceptable salt of the compound of claim 3 and a pharmaceutically acceptable carrier or excipient.

16. A pharmaceutical composition comprising an effective amount of the compound or a pharmaceutically acceptable salt of the compound of claim 4 and a pharmaceutically acceptable carrier or excipient.

17. A method for modulating ORL-1 receptor function in a cell, comprising contacting a cell capable of expressing the ORL-1 receptor with an effective amount of the compound or a pharmaceutically acceptable salt of the compound of claim 1.

18. A method for modulating ORL-1 receptor function in a cell, comprising contacting a cell capable of expressing the ORL-1 receptor with an effective amount of the compound or a pharmaceutically acceptable salt of the compound of claim 2.

19. A method for modulating ORL-1 receptor function in a cell, comprising contacting a cell capable of expressing the ORL-1 receptor with an effective amount of the compound or a pharmaceutically acceptable salt of the compound of claim 3.

20. A method for modulating ORL-1 receptor function in a cell, comprising contacting a cell capable of expressing the ORL-1 receptor with an effective amount of the compound or a pharmaceutically acceptable salt of the compound of claim 4.

21. A method for preparing a pharmaceutical composition, comprising the step of admixing a compound or a pharmaceutically acceptable salt of the compound of claim 1 and a pharmaceutically acceptable carrier or excipient.

22. A method for preparing a pharmaceutical composition, comprising the step of admixing a compound or a pharmaceutically acceptable salt of the compound of claim 2 and a pharmaceutically acceptable carrier or excipient.

23. A method for preparing a pharmaceutical composition, comprising the step of admixing a compound or a pharmaceutically acceptable salt of the compound of claim 3 and a pharmaceutically acceptable carrier or excipient.

24. A method for preparing a pharmaceutical composition, comprising the step of admixing a compound or a pharmaceutically acceptable salt of the compound of claim 4 and a pharmaceutically acceptable carrier or excipient.

25. A compound having the formula:

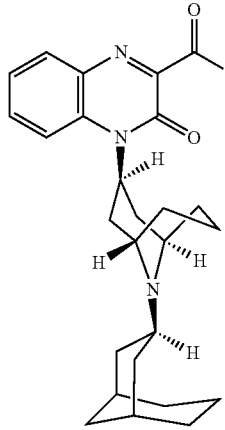 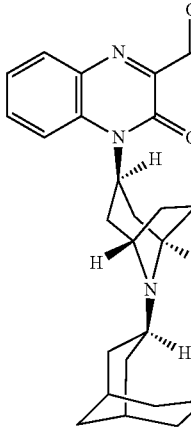 or

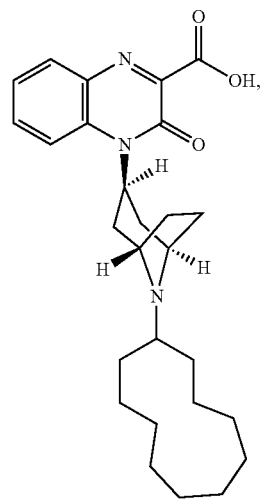

or a pharmaceutically acceptable salt thereof.

26. The compound of claim 25 having the formula:

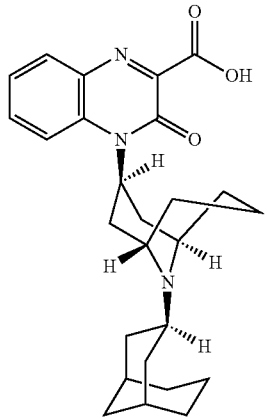

or a pharmaceutically acceptable salt thereof.

27. The compound of claim 25 having the formula:

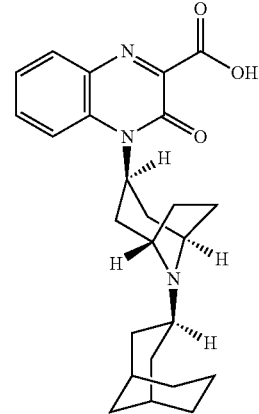

or a pharmaceutically acceptable salt thereof.

28. The compound of claim 25 having the formula:

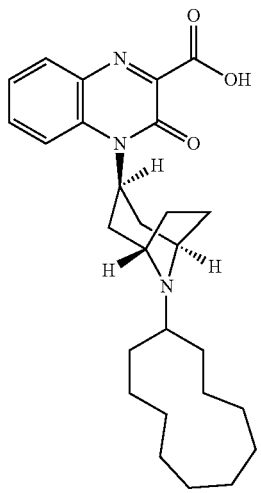 [SMILES: O=C(O)c1nc2ccccc2n([C@H]2C[C@H]3CC[C@@H](C2)N3C2CCCCCCCCCC2)c1=O]

or a pharmaceutically acceptable salt thereof.

29. The compound of claim 25 having the formula:

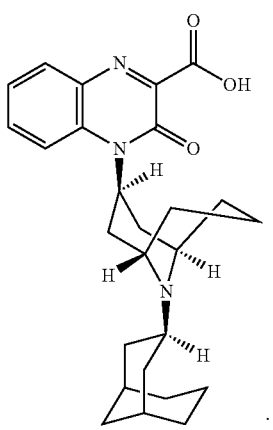

30. The compound of claim 25 having the formula:

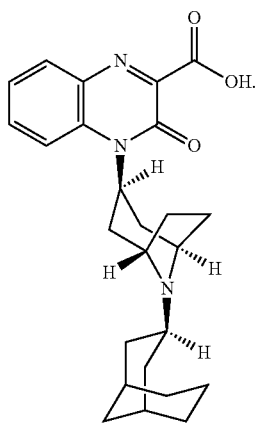

31. The compound of claim 25 having the formula:

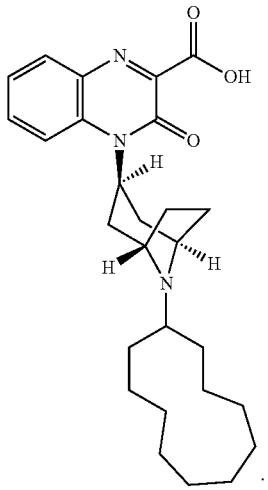 [SMILES: O=C(O)c1nc2ccccc2n([C@H]2C[C@H]3CC[C@@H](C2)N3C2CCCCCCCCCC2)c1=O]

32. The compound of claim 25 having the formula:

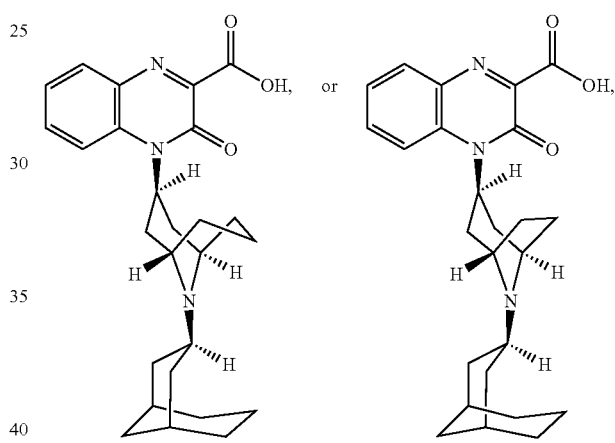

or a pharmaceutically acceptable salt thereof.

33. The compound of claim 25 having the formula:

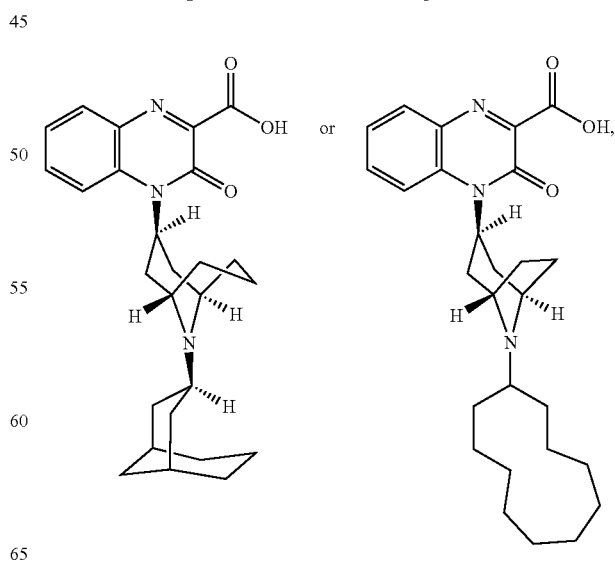

or a pharmaceutically acceptable salt thereof.

34. The compound of claim 25 having the formula:

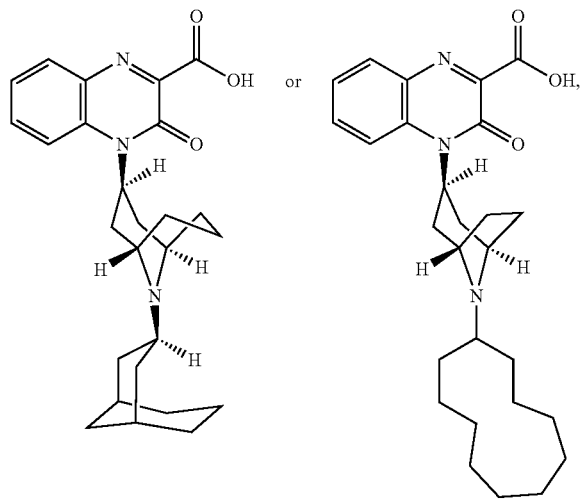

or a pharmaceutically acceptable salt thereof.

35. A pharmaceutically acceptable salt of the compound of claim 25, wherein the pharmaceutically acceptable salt is a p-toluenesulfonic acid salt, a sulfate salt, a phosphoric acid salt, or a hydrochloride salt.

36. A pharmaceutically acceptable salt of the compound of claim 26, wherein the pharmaceutically acceptable salt is a p-toluenesulfonic acid salt, a sulfate salt, a phosphoric acid salt, or a hydrochloride salt.

37. A pharmaceutically acceptable salt of the compound of claim 27, wherein the pharmaceutically acceptable salt is a p-toluenesulfonic acid salt, a sulfate salt, a phosphoric acid salt, or a hydrochloride salt.

38. A pharmaceutically acceptable salt of the compound of claim 28, wherein the pharmaceutically acceptable salt is a p-toluenesulfonic acid salt, a sulfate salt, a phosphoric acid salt, or a hydrochloride salt.

39. A pharmaceutical composition comprising an effective amount of the compound or a pharmaceutically acceptable salt of the compound of claim 25 and a pharmaceutically acceptable carrier or excipient.

40. A pharmaceutical composition comprising an effective amount of the compound or a pharmaceutically acceptable salt of the compound of claim 26 and a pharmaceutically acceptable carrier or excipient.

41. A pharmaceutical composition comprising an effective amount of the compound or a pharmaceutically acceptable salt of the compound of claim 27 and a pharmaceutically acceptable carrier or excipient.

42. A pharmaceutical composition comprising an effective amount of the compound or a pharmaceutically acceptable salt of the compound of claim 28 and a pharmaceutically acceptable carrier or excipient.

43. A method for modulating ORL-1 receptor function in a cell, comprising contacting a cell capable of expressing the ORL-1 receptor with an effective amount of the compound or a pharmaceutically acceptable salt of the compound of claim 25.

44. A method for modulating ORL-1 receptor function in a cell, comprising contacting a cell capable of expressing the ORL-1 receptor with an effective amount of the compound or a pharmaceutically acceptable salt of the compound of claim 26.

45. A method for modulating ORL-1 receptor function in a cell, comprising contacting a cell capable of expressing the ORL-1 receptor with an effective amount of the compound or a pharmaceutically acceptable salt of the compound of claim 27.

46. A method for modulating ORL-1 receptor function in a cell, comprising contacting a cell capable of expressing the ORL-1 receptor with an effective amount of the compound or a pharmaceutically acceptable salt of the compound of claim 28.

47. A method for preparing a pharmaceutical composition, comprising the step of admixing a compound or a pharmaceutically acceptable salt of the compound of claim 25 and a pharmaceutically acceptable carrier or excipient.

48. A method for preparing a pharmaceutical composition, comprising the step of admixing a compound or a pharmaceutically acceptable salt of the compound of claim 26 and a pharmaceutically acceptable carrier or excipient.

49. A method for preparing a pharmaceutical composition, comprising the step of admixing a compound or a pharmaceutically acceptable salt of the compound of claim 27 and a pharmaceutically acceptable carrier or excipient.

50. A method for preparing a pharmaceutical composition, comprising the step of admixing a compound or a pharmaceutically acceptable salt of the compound of claim 28 and a pharmaceutically acceptable carrier or excipient.

51. A compound having the formula:

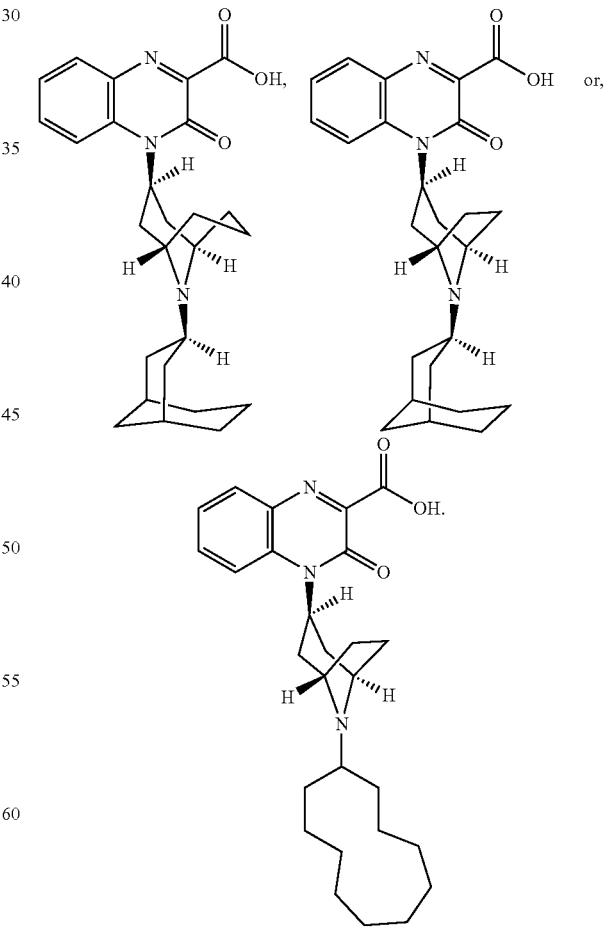

* * * * *

UNITED STATES PATENT AND TRADEMARK OFFICE
CERTIFICATE OF CORRECTION

PATENT NO. : 8,476,271 B2  
APPLICATION NO. : 13/010632  
DATED : July 2, 2013  
INVENTOR(S) : Naoki Tsuno et al.

It is certified that error appears in the above-identified patent and that said Letters Patent is hereby corrected as shown below:

In the claims

In column 126, line 32, claim 8, " 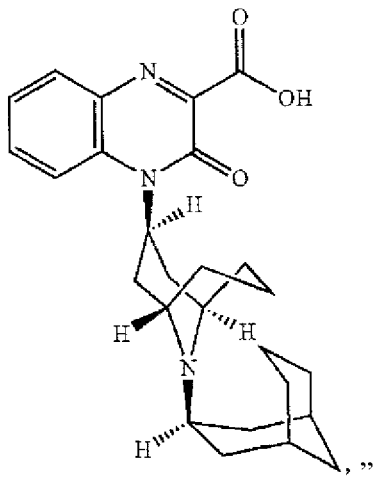 , "

should read -- 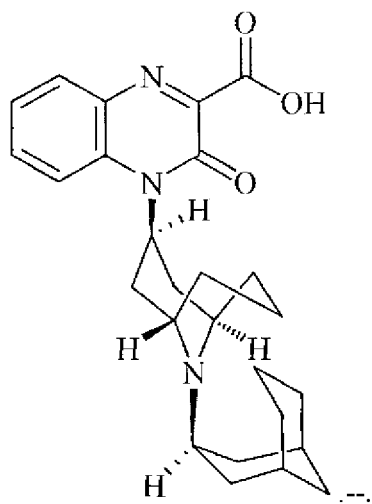 --.

Signed and Sealed this
Twenty-sixth Day of April, 2016

Michelle K. Lee
*Director of the United States Patent and Trademark Office*

CERTIFICATE OF CORRECTION (continued)
U.S. Pat. No. 8,476,271 B2

In the claims

In column 131, lines 3-20, claim 34, " 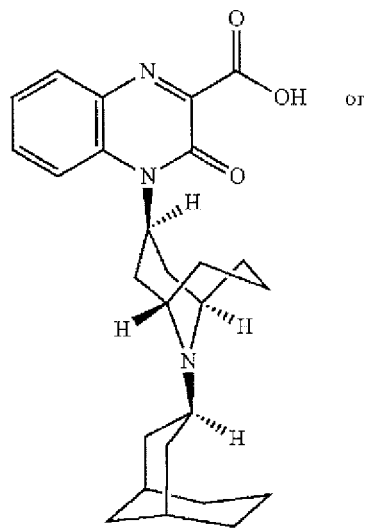 "

should read -- 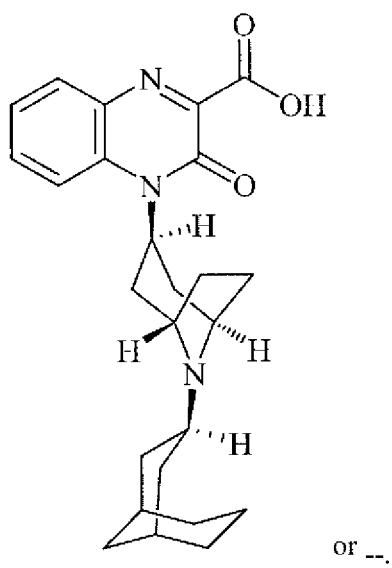 or --.